(12) United States Patent
Burton et al.

(10) Patent No.: US 7,939,641 B2
(45) Date of Patent: May 10, 2011

(54) MOTIF-GRAFTED HYBRID POLYPEPTIDES AND USES THEREOF

(75) Inventors: Dennis R. Burton, La Jolla, CA (US); Gianluca Moroncini, La Jolla, CA (US); R. Anthony Williamson, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 1127 days.

(21) Appl. No.: 10/410,907

(22) Filed: Apr. 8, 2003

(65) Prior Publication Data
US 2003/0215880 A1    Nov. 20, 2003

Related U.S. Application Data

(60) Provisional application No. 60/371,610, filed on Apr. 9, 2002.

(51) Int. Cl.
| C07K 16/00 | (2006.01) |
| C12P 21/08 | (2006.01) |
| A61K 38/395 | (2006.01) |
| A61K 39/395 | (2006.01) |
| A61K 39/42 | (2006.01) |
| G01N 33/53 | (2006.01) |

(52) U.S. Cl. ............... 530/387.3; 530/387.1; 530/387.9; 424/130.1; 424/133.1; 424/134.1; 424/159.1; 435/7.1

(58) Field of Classification Search .................. None
See application file for complete search history.

(56) References Cited

U.S. PATENT DOCUMENTS

| | | | |
|---|---|---|---|
| 3,843,443 A | 10/1974 | Fishman | 195/63 |
| 4,006,117 A | 2/1977 | Merrifield et al. | 260/45.9 |
| 4,244,721 A | 1/1981 | Gupta et al. | 65/31 |
| 4,507,230 A | 3/1985 | Tam et al. | 260/112.5 |
| 4,908,405 A | 3/1990 | Bayer et al. | 525/61 |
| 4,952,496 A | 8/1990 | Studier et al. | 435/91 |
| 5,231,167 A | 7/1993 | Zanetti et al. | 530/324 |
| 5,292,814 A | 3/1994 | Bayer et al. | 525/243 |
| 5,306,812 A | 4/1994 | Zanetti et al. | 530/413 |
| 5,389,449 A | 2/1995 | Afeyan et al. | 428/523 |
| 5,508,386 A | 4/1996 | Zanetti et al. | 530/387.3 |
| 5,583,202 A | 12/1996 | Zanetti | 530/387.3 |
| 5,639,581 A | 6/1997 | Iwasaki et al. | 430/59 |
| 5,652,138 A | 7/1997 | Burton et al. | 435/252.33 |
| 5,658,762 A | 8/1997 | Zanetti et al. | 435/69.6 |
| 5,693,478 A | 12/1997 | Vitek et al. | 435/7.1 |
| 5,750,361 A | 5/1998 | Prusiner et al. | 435/23 |
| 5,763,740 A | 6/1998 | Prusiner et al. | 800/2 |
| 5,773,572 A * | 6/1998 | Fishleigh et al. | 530/324 |
| 5,792,901 A | 8/1998 | Prusiner et al. | 800/2 |
| 5,846,533 A | 12/1998 | Prusiner et al. | 424/130.1 |
| 5,891,641 A | 4/1999 | Prusiner et al. | 435/7.1 |
| 5,908,969 A | 6/1999 | Prusiner et al. | 800/4 |
| 5,962,669 A | 10/1999 | Prusiner et al. | 536/23.5 |
| 6,114,175 A | 9/2000 | Klunk et al. | 436/63 |
| 6,172,043 B1 | 1/2001 | Ingram et al. | |
| 6,214,565 B1 | 4/2001 | Prusiner et al. | |
| 6,290,954 B1 | 9/2001 | Prusiner et al. | 424/130.1 |
| 6,372,214 B1 | 4/2002 | Prusiner et al. | 424/130.1 |
| 6,376,170 B1 | 4/2002 | Burton et al. | 435/5 |
| 6,537,548 B1 | 3/2003 | Prusiner et al. | 424/130.1 |
| 6,562,341 B2 | 5/2003 | Prusiner et al. | 424/130.1 |
| 6,677,125 B2 | 1/2004 | Prusiner et al. | 435/7.1 |
| 2001/0001061 A1 | 5/2001 | Prusiner et al. | 435/7.92 |
| 2001/0014455 A1 | 8/2001 | Prusiner et al. | 435/7.1 |
| 2002/0018674 A1 | 2/2002 | Miyamura | 399/302 |
| 2002/0087502 A1 | 7/2002 | Nagy et al. | 707/1 |
| 2003/0114360 A1 | 6/2003 | Cashman et al. | 514/2 |

FOREIGN PATENT DOCUMENTS

| | | |
|---|---|---|
| EP | 0 613 007 | 2/1994 |
| JP | A-7-501798 | 2/2007 |
| WO | 8603840 | 7/1986 |
| WO | WO 93/11155 | 6/1993 |
| WO | 9710505 | 3/1997 |
| WO | 97/16728 | 5/1997 |
| WO | 97/38011 | 10/1997 |
| WO | 9745746 | 12/1997 |
| WO | 99/15651 | 4/1999 |
| WO | 0068382 | 11/2000 |
| WO | 00/75324 | 12/2000 |
| WO | 0078344 | 12/2000 |
| WO | 0187911 | 11/2001 |
| WO | 0210335 | 2/2002 |
| WO | 03/085086 | 10/2003 |

OTHER PUBLICATIONS

Adams et al., "The c-*myc* oncogene driven by immunoglobulin enhancers induces lymphoid malignancy in transgenic mice", *Nature*, 318:533-5538 (1985).

Aguzzi, "Blood simple prion diagnostics", *Nature Medicine*, 7(3):289-290 (2001).

Alexander et al., "Expression of the c-*myc* Oncogene under Control of an Immunoglobulin Enhancer in Eμ-*myc* Transgenic Mice", *Molecular and Cellular Biology*, 7(4):1436-1444 (1987).

Arndt et al., "Helix-stabilized Fv (hsFv) Antibody Fragments: Substituting the Constant Domains of a Fab Fragment for a Heterodimeric Coiled-coil Domain", *J. Mol. Biol.*, 312:221-228 (2001).

Bajaj et al., "Ultra-Rare-Event Detection Performance of a Custom Scanning Cytometer on a Model Preparation of Fetal nRBCs", *Cytometry*, 39:285-294 (2000).

Baldwin et al., "Cloning of the Luciferase Structural Genes from *Vibrio harveyi* and Expression of Bioluminescence in *Escherichia coli*", *Biochemistry*, 23:3663-3667 (1984).

(Continued)

*Primary Examiner* — Olga N Chernyshev
(74) *Attorney, Agent, or Firm* — McKenna Long & Aldridge LLP; Stephanie Seidman

(57) ABSTRACT

Provided herein are hybrid polypeptides that specifically bind to a disease-associated isoform of a polypeptide involved in diseases of protein aggregation. The hybrid polypeptides can be used for diagnosis and treatment of such diseases. In a particular embodiment, a hybrid protein that specifically binds to the infectious form of a prion ($PrP^{Sc}$) is provided.

37 Claims, 4 Drawing Sheets

OTHER PUBLICATIONS

Figure 1A:
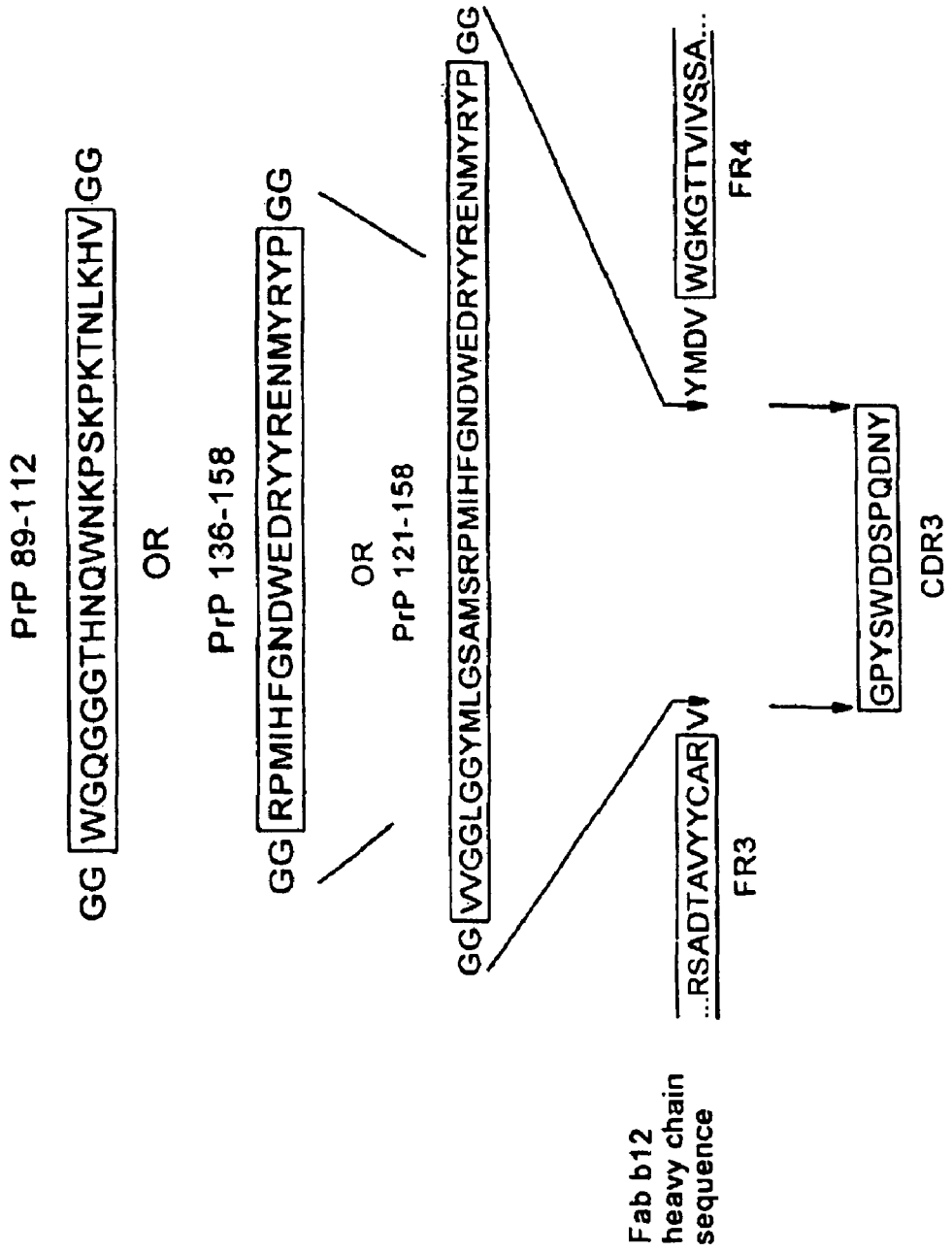

Barbas III and D.R. Burton, "Selection and evolution of high-affinity human anti-viral antibodies", *Trends in Biotechnology*, 14:230-234 (1996).

Barbas III and J. Wagner, "Synthetic Human Antibodies: Selecting and Evolving Functional Proteins", *Methods: A Companion to Methods in Enzymology*, 8:94-103 (1995).

Basler et al, "Scrapie and Cellular PrP Isoforms Are Encoded by the Same Chromosomal Gene", *Cell*, 46:417-428 (1986).

Benoist et al., "In vivo sequence requirements of the SV40 early promoter region", *Nature*, 290:304-310 (1981).

Berg et al., "Long-Chain Polystyrene-Grafted Polyethylene Film Matrix: A New Support for Solid-Phase Peptide Synthesis", *Berg*, 111:8024-8026 (1989).

Birkett et al., "Scrapie strains maintain biological phenotypes on propagation in a cell line in culture", *EMBO Journal*, 20(13):3351-3358 (2001).

Brinster et al., "Regulation of metallothionein-thymidine kinase fusion plasmids injected into mouse eggs", *Nature*, 296:39-42 (1982).

Bruce et al., "Transmissions to mice indicate that 'new variant' CJD is caused by the BSE agent", *Nature*, 389:498-501 (1997).

Bunin et al., "The combinatorial synthesis and chemical and biological evaluation of a 1,4-benzodiazepine library", *Proc. Natl. Acad. Sci. USA*, 91:4708-4712 (1994).

Burton et al., "Efficient Neutralization of Primary Isolates of HIV-1 by a Recombinant Human Monoclonal Antibody", *Science*, 266:1024-1027 (1994).

Butz et al., "Immunization and Affinity Purification of Antibodies Using Resin-Immobilized Lysine-Branched Synthetic Peptides", *Peptide Research*, 7(1):20-23 (1994).

Caughey, "Interactions between prion protein isoforms: the kiss of death?", *TRENDS in Biochemical Sciences*, 26(4):235-242 (2001).

Chandler, "Encephalopathy in Mice Produced by Inoculation with Scrapie Brain Material", *The Lancet*, ?:1378-1379 (1961).

Chen et al., "Analogous Organic Synthesis of Small-Compound Libraries: Validatino of Combinatorial Chemistry in Small-Molecule Synthesis", *J. Am. Chem. Soc.*, 116:2661-2662 (1994).

Clarke et al., "Evidence for the Multiplication of Scrapie Agent in Cell Culture", *Nature*, 225:100-101 (1970).

De Wet et al., "Firefly Luciferase Gene: Structure and Expression in Mammalian Cells", *Molecular and Cellular Biology*, 7(2):725-737 (1987).

De Boer et al., "The *tac* promoter: A functional hybrid derived from the *trp* and *lac* promoters", *Proc. Natl. Acad. Sci. USA*, 80:21-25 (1983).

Demart et al., "New Insight into Abnormal Prion Protein Using Monoclonal Antibodies", *Biochemical and Biophysical Research Communications*, 265:652-657 (1999).

DeWitt et al., ""Diversomers": An approach to nonpeptide, nonoligomeric chemical diversity", *Proc. Natl. Acad. Sci. USA*, 90:6909-6913 (1993).

Eck et al., "The Structure of Tumor Necrosis Factor-α at 2.6 Å Resolution", *The Journal of Biological Chemistry*, 264(29):17595-17605 (1989).

Engebrecht, J. and M. Silverman, "Identification of genes and gene products necessary for bacterial bioluminescence", *Proc. Natl. Acad. Sci. USA*, 81:4154-4158 (1984).

Fischer et al., "Binding of disease-associated prion protein to plasminogen", *Nature*, 408:479-483 (2000).

Gabriel et al., "Molecular cloning of a candidate chicken protein", *Proc. Natl. Acad. Sci. USA*, 89:9097-9101 (1992).

Gardner et al., "The complete nucleotide sequence of an infectious clone of cauliflower mosaic virus by M13mp7 shotgun sequencing", *Nucleic Acids Research*, 9(12):2871-2889 (1981).

Goldmann et al., "Different forms of the bovine PrP gene have five or six copies of a short, G-C-rich element within the protein-coding exon", *Journal of General Virology*, 72:201-204 (1991).

Goldmann et al., "Novel polymorphisms in the caprine PrP gene: a codon 142 mutation associated with scrapie incubation period", *Journal of General Virology*, 77:2885-2891 (1996).

Goldmann et al., "Corrigendum", *Journal of Gneral Virology*, 78(3):697 (1996).

Goldmann et al., "Two alleles of a neural protein gene linked to scrapie in sheep", *Proc. Natl. Acad. Sci. USA*, 87:2476-2480 (1990).

Grosschedl et al., "Introduction of a µ Immunoglobulin Gene into the Mouse Germ Line: Specific Expression in Lymphoid Cells and Synthesis of Functional Antibody", *Cell*, 38:647-658 (1984).

Hall et al., "Expression and Regulation of *Escherichia coli lacZ* Gene Fusions in Mammalian Cells", *Journal of Molecular and Applied Genetics*, 2:101-109 (1983).

Hall et al., "Stable chromosome fission associated with rDNA mobility", *Chromosome Research*, 3:417-422 (1995).

Hammer et al., "Diversity of Alpha-Fetoprotein Gene Expression in Mice Is Generated by a Combination of Separate Enhancer Elements", *Science*, 235:53-58 (1987).

Hanahan et al., "Heritable formation of pancreatic β-cell tumours in transgenic mice expressing recombinant insulin/simian virus 40 oncogenes", *Nature*, 315(9):115-122 (1985).

Harris et al., "A prion-like protein from chicken brain copurifies with an acetylcholine receptor-inducing activity", *Proc. Natl. Acad. Sci. USA*, 88:7664-7668 (1991).

Herrera-Estrella et al., "Light-inducible and chloroplast-associated expression of a chimaeric gene introduced into *Nicotiana tabacum* using a Ti plasmid vector", *Nature*, 310 :115-120 (1984).

Herrera-Estrella et al., "Expression of chimaeric genes transferred into plant cells using a Ti-plasmid-derived vector", *Nature*, 303(19):209-213 (1983).

Hill et al., "The same prion strain causes vCJD and BSE", *Nature*, 389:448-450 (1997).

Horiuchi, M. and B. Caughey, "Prion protein interconversions and the transmissible spongiform encephalopathies", *Structure Fold Des.*, 7(10):R231-R240 (1999).

Kaneko et al., "Evidence for protein X binding to a discontinuous epitope on the cellular prion during scrapie prion propagation", *Proc. Natl. Acad. Sci. USA*, 94:10069-10074 (1997).

Kanyo et al., "Antibody Binding Defines a Structure for an Epitope that Participates in the $PrP^c \to PrP^{Sc}$ Conformational Change", *J. Miol. Biol.*, 293:855-863 (1999).

Kascsak et al., "Mouse Polyclonal and Monoclonal Antibody to Scrapie-Associated Fibril Proteins", *Journal of Virology*, 61(12):3688-3693 (1987).

Kelsey et al., "Species- and tissue-specific expression of human α-antitrypsin in transgenic mice", *Genes & Development*, 1:161-171 (1987).

Kent et al., "Preparation and Properties of *tert*-Butyloxycarbonylaminoacyl-4-(oxymethyl)phenylacetamidomethyl-(Kel F-g-styrene) Resin, an Insoluble, Noncrosslinked Support for Solid Phase Peptide Synthesis", *Israel Journal of Chemistry*, 17:243-247 (1978).

Kleine et al., "Lipopeptide-Polyoxyethylene Conjugates as Mitogens and Adjuvants", *Immunobiol.*, 190:53-66 (1994).

Kollias et al., "Regulated Expression of Human $^A\gamma$-, β-, and Hybrid γβ-Globin Genes in Transgenic Mice: Manipulation of the Developmental Expression Patterns", *Cell*, 46:89-94 (1986).

Korth et al., "Prion ($PrP^{Sc}$)-specific epitope defined by a monoclonal antibody", *Nature*, 390 :74-77 (1997).

Kretzschmar et al., "Molecular Cloning of a Human Prion Protein cDNA", *DNA*, 5(4):315-324 (1986).

Kretzschmar et al., "Molecular cloning of a mink prion protein gene", *Journal of General Virology*, 73:2757-2761 (1992).

Krumlauf et al., "Developmental Regulation of α-Fetoprotein Genes in Transgenic Mice", *Molecular and Cellular Biology*, 5(17):1639-1648 (1985).

Leclerc et al., "Conformation of $PrP^C$ on the Cell Surface as Probed by Antibodies", *J. Mol. Biol.*, 326:475-483 (2003).

Leclerc et al., "Immobilized prion protein undergoes spontaneous rearrangement to a conformation having features in common with the infectious form", *The EMBO Journal*, 20(7):1547-1554 (2001).

Leder et al., "Consequences of Widespread Deregulation of the c-*myc* Gene in Transgenic Mice: Multiple Neoplasms and Normal Development", *Cell*, 45:485-495 (1986).

Locht et al., "Molecular cloning and complete sequence of prion protein cDNA from mouse brain infected with the scrapie agent", *PNAS*, 83:6372-6376 (1986).

MacDonald, "Expression of the pancreatic Elastase I Gene in Transgenic Mice", *Hepatology*, 7(1):42S-51S (1987).

Magram et al., "Developmental regulation of a cloned adult β-globin gene in transgenic mice", *Nature*, 315:338-340 (1985).

Maruyama et al., "Ebola Virus Can Be Effectively Neutralized by Antibody Produced in Natural Human Infection", *Journal of Virology*, 73(7):6024-6030 (1999).

Mason et al., "The Hypogonadal Mouse: Reproductive Functions Restored by Gene Therapy", *Science*, 234:1372-1378 (1986).

Matsunaga et al., "Cryptic Epitopes in N-Terminally Truncated Prion Protein Are Exposed in the Full-Length Molecule: Dependence of Conformation on pH", *Proteins: Structure, Function, and Genetics*, 44:110-118 (2001).

McLane et al., "Transplantation of a 17-amino acid α-helical DNA-binding domain into an antibody molecule confers sequence-dependent DNA recognition", *Proc. Natl. Acad. Sci. USA*, 92:5214-5218 (1995).

Merrifield, "Solid-Phase Peptide Synthesis. III. An Improved Synthesis of Bradykinin", *Biochemistry*, 3(9):1385-1390 (1964).

Mitchell et al., "Preparation of Aminomethyl-Polystyrene Resin by Direct Amidomethylation", *Tetrahedron Letters*, 42:3795-3798 (1976).

Mitchell et al., "A New Synthetic Route to tert-Butyloxycarbonylaminoacyl-4-(oxymethyl)phenylacetamidomethyl-resin, an Improved Support for Solid-Phase Peptide Synthesis", *J. Org. Chem.*, 43(14):2845-2852 (1978).

Mosbach et al., "Immobilization Techniques", *Section II, Methods in Enzymology*, 44:53-65 (1976).

Oesch et al., "A Cellular Gene Encodes Scrapie PrP 27-30 Protein", *Cell*, 40:735-746 (1985).

Ornitz et al., "Elastase I Promoter Directs Expression of Human Growth Hormone and SV40 T Antigen Genes to Pancreatic Acinar Cells in Transgenic Mice", *Cold Spring Harbor Symp. Quant. Biol.*, 50:399-409 (1986).

Padwa et el., "Photoelimination of a β-Keto with a Low-Lying π-πTriplet State", *J. Org. Chem.*, 36(23):3550-33552 (1971).

Peretz et al., "Antibodies inhibit prion propagation and clear cell cultures of prion infectivity", *Nature*, 412:739-743 (2001).

Peretz et al., "A Change in the Conformation of Prions Accompanies the Emergence of a New Prion Strain", *Neuron*, 34:921-932 (2002).

Peretz et al., "A Conformational Transition at the N Terminus of the Prion Protein Features in Formation of the Scrapie Isoform", *J. Mol. Biol.*, 273:614-622 (1997).

Peretz et al., "Strain-specified relative conformational stability of the scrapie prion protein", *Protein Science*, 10:854-863 (2001).

Petersen et al., "Mapping of linear epitopes recognized by monoclonal antibodies with gene-fragment phage display libraries", *Mol Gen Genet*, 249:425-431 (1995).

Pinkert et al., "An albumin enhancer located 10 kb upstream functions along with its promoter to direct efficient, liver-specific expression in transgenic mice", *Genes & Development*, 1:268-276 (1987).

Powers et al., "Protein Purification by Affinity Binding to Unilamellar Vesicles", *Biotechnology and Bioengineering 33*, 33:173-182 (1989).

Priola et al., A Single Hamster PrP Amino Acid Blocks Conversion to Protease-Resistant PrP in Scrapie-Infected Mouse Neuroblastoma Cells, *Journal of Virology*, 69(12).:7754-7758 (1995).

Prusiner, "Prions", *Proc. Natl. Acad. Sci. USA*, 95:13363-13383 (1998).

Readhead et al., "Expression of a Myelin Basic Protein Gene in Transgenic Shiverer Mice: Correction of the Dysmyelinating Phenotype", *Cell*, 48:703-712 (1987).

Riek et al., "NMR characterization of the full-length recombinant murine prion protein, mPrP(23-231)", *FEBS Letters*, 413:282-288 (1997).

Safar et al., "Measuring prisons causing bovine spongiform encephalopathy or chronic wasting disease by immunoassays and transgenic mice", *Nature Biotechnology*, 20:1147-1149 (2002).

Safer et al., "Eight prion strains have $PrP^{Sc}$", *Nature Medicine*, 4(10):1157-1150 (1998).

Saphire et al., "Crystal Structure of a Neutralizing Human IgG Against HIV-1: A Template for Vaccine Design", *Science*, 293:1155-1159 (2001).

Scott et al., "Compelling transgenetic evidence for transmission of bovine spongiform encephalopathy prions to humans", *PNAS*, 96(26):15137-15142 (1999).

Scott et al., "Identification of a prion protein epitope modulating transmission of bovine spongiform encephalopathy prions to transgenic mice", *Proc. Natl. Acad. Sci. USA*, 94:14279-14284 (1997).

Shaked et al., "The binding of prion proteins to serum components is affected by detergent extraction conditions", *Journal of Neurochemistry*, 82:1-5 (2002).

Shani, "Tissue-specific expression of rat myosin light-chain 2 gene in transgenic mice", *Nature*, 314:283-286 (1985).

Smith et al., "Single-step purification of polypeptides expressed in *Escherichia coli* as fusions with glutathione S-transferase", *Gene*, 67:31-40 (1988).

Sucholeiki, "Solid-Phase Photochemical C-S Bond Cleavage of Thioethers—A New Approach to the Solid-Phase Production of Non-Peptide Molecules", *Tetrahedron Lttrs.*, 35:7307-7310 (1994).

Supattapone et al., "Prion Protein of 106 Residues Creates an Artificial Transmission Barrier for Prion Replication in Transgenic Mice", *Cell*, 96:869-878 (1999).

Swift et al., "Tissue-Specific Expression of the Rat Pancreatic Elastase I Gene in Transgenic Mice", *Cell*, 38:639-646 (1984).

Toh et al., "Isolation and characterization of a rat liver alkaline phosphatese gene", *Eur. J. Biochem.*, 182:231-237 (1989).

Vedejas et al., "A Method for Mild Photochemical Oxidation; Conversion of Phenacyl Sulfides into Carbonyl Compounds", *J. Org. Chem.*, 49:573-575 (1984).

Villa-Komaroff et al., "A bacterial clone synthesizing proinsulin", *Biochemistry*, 75(8):3727-3731 (1978).

Wagner et al., "Nucleotide sequence of the thymidine kinase gene of herpes simplex virus type 1", *Proc. Natl. Acad. Sci. USA*, 78(3):1441-1445 (1981).

Wang et al., "Solid Synthesis of Protected Peptides via Photolytic Cleavage of the α-Methylphenacyl Ester Anchoring Linkage", *J. Org. Chem.*, 41:3258-3260 (1976).

Williamson et al., "Circumventing tolerance to generate autologous monoclonal antibodies to the prion protein", *Proc. Natl. Acad. Sci. USA*, 93:7279-7282 (1996).

Williamson et al., "Human monoclonal antibodies against a plethora of viral pathogens from single combinatorial libraries", *Proc. Natl. Acad. Sci. USA*, 90:4141-4145 (1993).

Williamson et al., "Mapping the Prion Using Recombinant Antibodies", *Journal of Virology*, 72(11):9413-9418 (1998).

Yamamoto et al., "Identification of a Functional Promoter in the Long Terminal Repeat of Rous Sarcoma Virus", *Cell*, 22:787-797 (1980).

Zanusso et al., "Prion protein expression in different species: Analysis with a panel of new mAbs", *Proc. Natl. Acad. Sci. USA*, 95:8812-8816 (1998).

Zuckermann et al., "Efficient Method for the Preparation of Peptoids [Oligo(N-substituted glycines)] by Submonomer Solid-Phase Synthesis", *J. Am. Chem. Soc.*, 114:10646-10647 (1992).

Zulianello et al., "Dominant-Negative Inhibition of Prion Formation Diminished by Deletion Mutagenesis of the Prion Protein", *Journal of Virology*, 74(9):4351-4360 (2000).

Aguzzi, A., "Neuro-immune connection in spread of prions in the body?", *Lancet 349*:742-743 (1997).

Aguzzi et al., "The prion's perplexing persistence", *Nature 392*:763-770 (1998).

Blattler et al., "PrP-expressing tissue required for transfer of scrapie infectivity from spleen to brain", *Nature 389*:69-73 (1997).

Bolton et al., "Identification of a protein that purifies with the scrapie prion", *Science 218*:1309-1311 (1982).

Bolton et al., "Molecular location of a species-specific epitope on the hamster scrapie agent protein", *J. Virol. 65*:3667-3675 (1991).

Brown et al., "Friendly fire in medicine: hormones, homografts, and Creutzfeldt-Jakob disease", *Lancet 340*:24-27 (1992).

Brown et al., "The distribution of infectivity in blood components and plasma derivatives in experimental models of transmissible spongiform encephalopathy", *Transfusion 38*:810-816 (1998).

Casaccia et al., "Levels of infectivity in the blood throughout the incubation period of hamster peripherally injected with scrapie", *Arch. Virol.* 108:145-149 (1989).

Cohen et al., "Structural clues to prion replication", *Science* 264:530-531 (1994).

Crameri et al., "Construction and evolution of antibody-phage libraries by DNA shuffling", *Nature Med.* 2:100-102 (1996).

Crameri et al., "DNA shuffling of a family of genes from diverse species accelerates directed evolution", *Nature* 391:288-291 (1998).

Donne et al., "Structure of the recombinant full-length hamster prion protein PrP(290231): The N-terminus is highly flexible", *Proc. Natl. Acad. Sci. U.S.A.* 94:13452-13457 (1997).

Hill et al., "Diagnosis of new variant Creutzfeldt-Jakob disease by tonsil biopsy", *Lancet* 349:99 (1997).

Hilton et al., "Prion immunoreactivity in appendix before clinical onset of variant Creutzfeldt-Jakob disease", *Lancet* 352:703-704 (1998).

James et al., "Solution structure of a 142-residue recombinant prion protein corresponding to the infectious fragment of the scrapie isoform", *Proc. Natl. Acad. Sci. U.S.A.* 94:10086-10091 (1997).

Mehlhorn et al., "High-level expression and characterization of a purified 142-residue polypeptide of the prion protein", *Biochemistry* 35:5528-5537 (1996).

Muramoto et al., "Recombinant scrapie-like prion protein of 106 amino acids is soluble", *Proc. Natl. Acad. Sci. U.S.A.* 93:15457-15462 (1997).

Pan et al., "Conversion of $\alpha$-helices into $\beta$-sheets features in the formation of the scrapie prion protein", *Proc. Natl. Acad. Sci. U.S.A.* 90:10962-10966 (1993).

Prusiner et al., "Biology and genetics of prion diseases", *Annu. Rev. Microbiol.* 48:655-686 (1994).

Riek et al., "NMR structure of the mouse prion protein domain PrP (121-131)", *Nature* 383:180-182 (1996).

Safar et al., "Conformational transitions, dissociation and unfolding of scrapie amyloid (prion) protein", *J. Biol. Chem.* 268:20276-20284 (1993).

Yang et al., "CDR walking mutagenesis for the affinity maturation of a potent human anti-HIV-1 antibody into the picomolar range", *J. Mol. Biol.* 254:392-403 (1995).

Yelton et al., "Affinity maturation of the BR96 anti-carcinoma antibody by codon-based mutagenesis", *J. Immunol.* 155:1994-2004 (1995).

Zhang et al., "Conformational transitions in peptides containing two putative $\alpha$-helices of the prion protein", *J. Mol. Biol.* 250:514-526 (1995).

Zhang et al., "Physical studies of conformational plasticity in a recombinant prion protein", *Biochemistry* 36:3543-3553 (1997).

Hanan et al., "Immunomodulation of the human prion peptide 106-126 aggregation," Biochemical and Biophysical Research Communications, 280:115-120 (2001).

Certified English Translation for International PCT Application No. WO 99/15651, Jun. 6, 2007.

Williamson, Department of Health and Human Services Grant Application, "Ultra-high affinity antibodies to detect single infectious prions," funding period from Sep. 30, 1999 to Sep. 29, 2003; pp. 1, 2, 11-35.

Examination Report, issued Jun. 4, 2008, in connection with New Zealand Patent Application No. 536054.

Examination Report, issued Mar. 9, 2009, in connection with New Zealand Patent Application No. 536054.

Examination Report, issued Jul. 29, 2008, in connection with Japanese Patent Application No. 2003-582265.

Examination Report, issued Mar. 10, 2009, in connection with Japanese Patent Application No. 2003-582265.

Examination Report, issued Mar. 10, 2009, in connection with Japanese Patent Application No. 2009-018209.

Examination Report, issued Sep. 10, 2009, in connection with European Patent Application No. 03746148.0.

\* cited by examiner

FIG. 2

MOTIF-GRAFTED HYBRID POLYPEPTIDES AND USES THEREOF

RELATED APPLICATIONS

Benefit of priority is claimed under 35 U.S.C. §119(e) to U.S. provisional application Serial No. 60/371,610, filed Apr. 9, 2002, entitled "MOTIF-GRAFTED HYBRID POLYPEPTIDES CONTAINING THE REPLICATIVE INTERFACE OF CELLULAR PRION POLYPEPTIDE AND FROM OTHER DISEASES OF PROTEIN AGGREGATION AND USES THEREOF" to R. Anthony Williamson, Dennis R. Burton and Gianiuca Moroncini.

Subject matter herein is related to subject matter in International PCT application No. PCT/US03/01856, filed the same day herewith, entitled "MOTIF-GRAFTED HYBRID POLYPEPTIDES AND USES THEREOF." The subject matter of each of these applications is incorporated herein by reference in its entirety.

GRANTS

Subject matter provided herein was made with government support under grant Nos. HL63817, AG02132 and NS14069, awarded by the National Institutes of Health. The government may have certain rights in such subject matter.

Transmissible spongiform encephalopathies, including Creutzfeldt-Jakob disease (CJD) of humans and bovine spongiform encephalopathy (BSE; also known as Mad Cow Disease) and scrapie of animals, are closely related dementia diseases of cows, sheep, humans and other animals. Bovine spongiform encephalopathy (BSE), scrapie of sheep, Kuru and Creutzfeldt-Jakob disease (CJD) of humans are only a few examples of a group of neurodegenerative disorders named transmissible spongiform encephalopathies (TSE); they are characterized by loss of motor control, dementia, paralysis, blindness, wasting and eventually death. These diseases can be inherited or sporadic. A risk of contracting TSE for humans is through food products derived from BSE-infected cattle. Another transmission risk is possible infection through human blood and blood products that originated from TSE-infected donors. This family of invariably fatal neurodegenerative diseases and chronic wasting disease (CWD) of deer and elk are caused by prions (Prusiner et al. (1998) *Proc. Natl. Acad. Sci U.S.A.* 95:13363-13383).

Prion protein corresponds to the product of a gene naturally found in the genome of all vertebrates from human to fish. The gene typically is encoded by about 771 nucleotides that encode 257 amino acids. It is expressed in many, but not all, tissues of animals, always on the outside surface of the cell membrane. The genes from more than 89 species have been sequenced; mutations, including those with insertions and deletions and other alterations also have been identified and sequenced. PrP related nucleic acid has been detected in organisms such as Drosophila, the nematode *Caenorhabditis elegans* and yeast.

Prion protein precursor (PrP or $PrP^c$) is the normal cellular isoform of the prion protein. The infectious prion protein is referred to as $PrP^{Sc}$ and the normal prion protein is $PrP^c$ (the "sc" is for scrapie and the "c" for cellular). Truncated and recombinant forms also are known. There are therefore two different isoforms of the prion protein, one is expressed normally and one is present aberrantly. $PrP^{Sc}$ is the principal component of amyloid plaques sometimes found in the brains of sheep infected with scrapie and in brains of humans and other animals infected with prion diseases. Conversion of $PrP^c$ into $PrP^{Sc}$ is thought to involve conversion of alpha-helical regions of the protein into beta sheets. Mutations associated with familial prion disease increase the likelihood of conversion; different mutations result in different disease symptoms. CJD is a dementia, GSS (Gerstmann-Strassler-Scheinker Disease) ataxia, and FFI (fatal familial insomnia).

Inherited forms of the prion disease constitute about 25% of all cases of prion diseases in humans notably GSS, familial CJD and FFI. In each of the inherited forms, mutations have been found in the ORF (open reading frame) of the PRNP gene. The first half of the PRNP ORF contains about 170 bp with a high content (about 80%) of the nucleotides guanidine (G) and cytidine (C), most of this sequence is organized in 24 bp (or 27 bp) repeats. Few differences are observed between these sequences, and between those in other species suggesting that they are highly conserved through evolution. The gene is predominantly expressed in neuronal cells as well as ganglia and nerves of the peripheral nervous system. It is not exclusively expressed in the central nervous system (CNS) and neurons, but also is expressed in other tissues, including, kidney, heart, lung and spleen. There are many mutations that have been identified with the PRNP ORF and are often genetically linked to hereditary prion disease. The $PrP^c$ protein is expressed as a glycosylphosphatidyl inositol-anchored glycoprotein found on the outer cell membrane of neurons and to a lesser extent of lymphocytes and other cells.

Transmission between species is characterized by low transmission rates or a long incubation time. BSE has been transmitted to mice, sheep, pigs and marmoset. Transmission is characterized by the induction of an altered form of the host gene product through its interaction with the homologous component of the infectious material. Mice are not infected by human prions, nor are transgenic mice bearing a copy of human PrP; however, transgenic mice bearing a hybrid mouse/human PrP are infected by human prions. This suggests that an interaction between a host factor and PrP is necessary for transmission and that the mouse factor is not sufficiently similar to the human factor to interact with the human PrP. Including some mouse sequences in the otherwise human PrP restored the interaction.

The only known component of the infectious prion is an abnormal, disease-causing isoform of the prion protein, designated $PrP^{Sc}$. To distinguish the normal, cellular isoform ($PrP^c$) from $PrP^{Sc}$ in infected tissues, standard immunoassays have relied on the proteolytic degradation of $PrP^r$, followed by detection of the protease-resistant core of $PrP^{Sc}$ (designated PrP 23-30) that is antigenically indistinguishable from $PrP^c$ (see, e.g., Oesch et al. (1985) *Cell* 40:735-746; Prusiner (1999) in *Prion Biology and Diseases* (ed. S. B. Prusiner), Cold Spring harbor Laboratory Press).

The emergence in Europe of a new variant form of CJD (vCJD) is closely associated with the ingestion of BSE prion tainted meat, and has elevated concern over the threat prions pose to the safety of food and blood products (Bruce et al. (1997) *Nature* 389:498-501; Hill et al. (1997) *Nature* 389: 448-450). Studies in transgenic mice that harbor human and bovine PrP provide evidence that prions from BSE-infected cattle cause vCJD (Scott et al. (1999) *Proc. Natl. Acad. Sci. U.S.A.* 96:15137-15142; Scott et al. (1997) *Proc. Natl. Acad. Sci. U.S.A.* 94: 14279-14284; and Hill et al. (1997) *Nature* 389:448-450). Whether CWD and BSE prions have similar strain characteristics and whether CWD can traverse the species barrier to humans are major public health concerns (Horiuchi et al. (1999) *Structure* 7:R231-R240; Raymond et al. (1997) *Nature* 388:285-288). The absence of a sensitive diagnostic test for prion infection has prevented an accurate assessment of how many of the millions of individuals exposed to BSE prions are currently incubating disease (Aguzzi et al. (2001) *Nat. Med.* 7:289-290).

Prototypic assays of potential use in prion diagnostics have been developed (see, e.g., Safer et al. (1998) *Nat. Med.* 4:1157-1165). For example, a conformation-dependent immunoassay has been developed that quantifies PrP$^{Sc}$ by following antibody binding to the denatured and native forms of PrP simultaneously. The assay (see, Safar et al. (2002) *Nature Biotechnology* Mar. 20, 2002 issue; see also, copending U.S. application Ser. No. 09/627,218) uses a recombinant antibody fragment (recFab) that reacts with residues 95-105 of bovine PrP for detection and a second recFab that reacts with residues 132-156 for capture.

Antibodies distinguishing between PrP$^c$ and PrP$^{Sc}$ are of value in studying the specific machinery of prion replication and in the diagnosis of prion infection. Although monoclonal antibodies recognizing PrP$^c$ are available (Williamson et al. (1996) *Proc. Natl. Acad. Sci. U.S.A.* 93:7279-7282; Williamson et al. (1998) *J. Virol.* 72:9413-9418; Zanusso et al. (1998) *Proc. Natl. Acad. Sci. U.S.A.* 95:8812-8816; Demart et al. (1999) *Biochem. Biophys. Res. Commun.* 265:652-657), antibodies that specifically recognize non-Denatured PrP$^{Sc}$ or PrP 27-30 are not available. Immunization of normal or PrP-null animals with a wide range of PrP antigens including infectious prions, PrP$^c$, and recombinant and synthetic PrP molecules refolded into α-helical or β-sheet-rich conformations, has repeatedly failed to elicit high-affinity antibodies that exclusively recognize disease-associated forms of PrP (Williamson et al. (1996) *Proc. Natl. Acad. Sci. U.S.A.* 93:7279-7282; Williamson et al. (1998) *J. Virol.* 72:9413-9418; and Peretz et al. (1997) *J. Mol. Biol.* 273:614-622). Reports (see, e.g., Korth et al. (1997) *Nature* 390:74-77) of such an antibody have proven premature (Fischer et al. (2000) *Nature* 408:479-483; see also Heppner et al. (2001) *Science* 294:178-182; see, also, pending U.S. application Ser. No. 09/627,218). Attempts to circumvent immunization by using purified infectious prions to select specific binders from large naive single-chain antibody phage display libraries have been similarly unproductive.

The emergence of variant forms of prions, the long incubation time for prion-caused diseases and the possibility of interspecies transmission point out the need to develop assays for detection of contaminated foods and body tissues and fluids as well as the need to develop therapeutics that specifically target infectious forms of prions. Therefore, it is an object herein, among other objects, to provide reagents that specifically react with infectious prions, diagnostic assays using such reagents, and methods for preparing reagents for identifying infectious and disease causing forms of other amyloid proteins and other disease-associated conformation dependent proteins.

SUMMARY

Provided herein are reagents that specifically react with a target polypeptide, which is the infectious form of a polypeptide associated with a disease of protein aggregation (a disease involving a conformationally altered protein), such as amyloid diseases. Hybrid molecules, such as hybrid polypeptides, with such specificity are provided. The hybrid polypeptides include a polypeptide motif that specifically interacts with the target polypeptide and that is inserted into a scaffold, such as a portion of an antibody or an enzyme or other suitable recipient, such that the resulting hybrid molecule specifically binds to conformation of the protein and not to another conformation of the protein. Typically, the targeted conformation is the conformation involved in a disease. The polypeptide motif is inserted into the scaffold such that any desired function of the scaffold is retained and the inserted motif as presented retains it ability to specifically bind to the target. The selected scaffold can be exploited for its activities or binding sites to aid or permit detection of complexes between the motif and the target polypeptide. Also provided is a method for preparing polypeptides with conformation specificity.

Methods for producing reagents for detection or diagnosis of conformationally altered protein diseases and for screening for reagents for treatment thereof are provided. Such diseases include, but are not limited to, prion diseases, such as but not limited to, Creutzfeldt-Jakob disease, including variant, sporadic and iatrogenic, scrapie and bovine spongiform encephalopathy; Alzheimer's Disease; Type II Diabetes (islet amyloid peptide); Huntington's Disease; immunoglobulin amyloidosis; reactive amyloidosis associated with chronic inflammatory disease, e.g., inflammatory arthritis, granulomatous bowel disease, tuberculosis and leprosy; hereditary systemic amyloidosis associated with autosomal dominant inheritance of variant transthyretin (a.k.a., prealbumin) gene; ALS; Pick's Disease; Parkinson's disease; Frontotemporal dementia; Diabetes Type II; Multiple myeloma; Plasma cell dyscrasias; Familial amyloidotic polynueuropathy; Medullary carcinoma of thyroid; chronic renal failure; congestive heart failure; senile cardiac and systemic amyloidosis; chronic inflammation; atherosclerosis; familial amyloidosis and other such diseases.

The hybrid polypeptides can be used as reagents to detect the presence of the target polypeptide in a sample, such as a body fluid, tissue or organ or a preparation derived therefrom, and in drug screening assays to identify compounds that antagonize or agonize (i.e., modulate) the activity of a target polypeptide or that competitively inhibit interaction thereof with an infectious or disease-causing form of a target polypeptide, such as PrP$^{Sc}$. The hybrid molecules also can be used as therapeutics. Since they specifically bind to a target polypeptide, they can be used to inhibit its activity, such as preventing or reducing infectivity or the activity that results in protein aggregation or the conformation change leading to a deleterious effect. For example, as a therapeutic for treatment of diseases of protein aggregation a hybrid polypeptide can interrupt the polymerization or aggregation characteristic of disease pathogenesis.

In an exemplary embodiment, hybrid polypeptides that specifically react with the infections form of a prion (PrP$^{Sc}$) are provided. Motif-grafted polypeptides that bind specifically to disease-associated conformations of PrP are provided. In exemplary embodiments, a series of polypeptides containing PrP sequence between residues 119-158 (using Syrian hamster nomenclature) were used to replace the extended heavy-chain-complementarity-determining region 3 (HCDR3) of an IgG antibody Fab specific for the envelope glycoprotein of HIV-1 (see, U.S. Pat. No. 5,652,138, which provides the antibody). The resulting engineered PrP-Fab fragments (or PrP-IgG molecules) specifically bind to PrP$^{Sc}$ and its protease-resistant core, but not to PrP$^c$, other cellular components or to HIV-1 envelope. Residues within the 119-158 segment, such as residues 89-112 and 136-158, of PrP$^c$ are a key component of one face of the PrP$^c$-PrP$^{Sc}$ complex. It was observed that scrambling of residues 136-158 abolishes reactivity.

Grafted molecules, such as the PrP$^{Sc}$-specific polypeptides exemplified herein, and other molecules produced by the approach provided herein can be used in to study the biology of such molecules as well as for development of diagnostics and therapeutics. For example, polypeptides that are specific for non-denatured PrP$^{Sc}$-prions that are described and provided herein can be used in the study of biology and replication and in the detection of infectious prions in human and animal materials.

Methods for identifying disease-related or causative polypeptides or to test for infection or contamination by such particles or complexes of such particles are provided. The methods are effected by contacting a reagent hybrid polypeptide provided herein with a sample to be tested and detecting or identifying complexes formed between the reagent hybrid polypeptide and the particle or complex in sample that is indicative of the presence of an infectious agent. The methods can be performed as homogeneous or heterogeneous assays. In the heterogeneous assays, the reagents can be linked or attached directly or indirectly to a solid support and contacted with sample. Alternatively, the sample or components of the sample can be linked to a support and contacted with the reagents. Complexes between the reagents and molecules of interest in the sample are identified. The reagents can be designed to further include a second binding site to permit convenient identification, such as by binding a second detectable moiety.

In an exemplary embodiment, methods for detection of $PrP^{Sc}$ in a sample, such as a body fluid, tissue or organ from an animal, are provided. The methods are effected in solution phase or by providing the reagents or sample bound directly or indirectly to a solid support. Complexes between the reagents provided herein and the target polypeptides in the sample are detected.

Also provided are methods for identifying individual cells that contain or express a disease-causing or infectious conformer of a polypeptide involved in a disease of protein aggregation, such as prion-infected cells in a background of non-infected cells. This method is effected by contacting cells, such as blood cells, with a detectably labeled polypeptide provided herein that specifically binds to the disease-causing or infectious conformer, and detecting labeled cells. For example, a method for detecting prion-infected cells, even cells present in low amounts (at frequency typically less than 1:10,000) using a hybrid polypeptide, or a plurality thereof, provided herein that binds to non-denatured $PrP^{Sc}$ and that is detectably labeled, such as fluorescently labeled, and detecting cells that contain the labeled polypeptide, such as by scanning cytometry methods for detection of rare events. This method can be effected by known cytometry methods (see, e.g., Bajaj et al. (2000) *Cytometry* 39:285-294) and instrumentation therefor (see, e.g., U.S. application Ser. No. 09/123,564, published as US2002018674 and commercialized by Q3DM, LLC, San Diego). Very low concentrations of infected cells can be detected by such methods.

Combinations of the hybrid polypeptides provided herein and solid supports also are provided. The combinations can be provided as kits that optionally include instructions for performing assays for detection of target polypeptides.

Also provided are anti-idiotype antibodies (monoclonal or polyclonal) that are produced by immunizing a suitable animal with a polypeptide or antibody or fragment thereof that recognizes the about 89-112 and/or 136-158 region of PrP, such as D13 (see, e.g., Matsunaga et al. (2001) *Proteins* 44:110-118; see, Williamson et al. (1998) *J. Virol.* 72:9413-9418; D13 light chain, see, SEQ ID NO:29 and SEQ ID NO:30; D13 heavy chain, see, SEQ ID NO:31 and SEQ ID NO:32); or D18 (see, e.g., Peretz et al. (2001) *Nature* 412:739-743; Williamson et al. (1998) *J. Virol.* 72:9413-9418; D18 light chain see, SEQ ID NO:33 and SEQ ID NO:34; D18 heavy chain see, SEQ ID NO:35 and SEQ ID NO:36) monoclonal antibody Fab fragments or other inhibitory antibodies.

Anti-idiotype antibodies raised against the combining sites of inhibitory antibodies or Fabs, such as D18 or D13, can generate antibodies that recognize native $PrP^{Sc}$. Such anti-idiotype antibodies can be used in all of the diagnostic, prognostic, therapeutic and screening methods that the hybrid polypeptides also provided herein are used. Methods for preparing such anti-idiotype antibodies by immunizing with a polypeptide or antibody or fragment thereof that recognizes the about 89-112 and/or 136-158 region of PrP, such D13 or D18 monoclonal antibody Fab fragments (for D13 light chain see, SEQ ID NO:29 and SEQ ID NO:30; for D13 heavy chain, see, SEQ ID NO:31 and SEQ ID NO:32; for D18 light chain see, SEQ ID NO:33 and SEQ ID NO:34, for D18 heavy chain see, SEQ ID NO:35 and SEQ ID NO:36), also are provided.

DESCRIPTION OF THE DRAWINGS

FIG. 1 present A) a schematic illustration of mouse Prp 89-112, Prp 136-258 and PrP 121-158 peptide replacing Fab b12 HCDR3 sequence to yield PrP-Fab 121-158. The N-terminal Val residue corresponding to amino acid residue 118 of SEQ ID NO:4 and 4 C-terminal residues (Tyr-Met-Asp-Val) corresponding to amino acid residues 132 to 135 of SEQ ID NO:4 of the original b12 HCDR3 are retained; two Gly residues are added to each flank of the grafted PrP sequence; and B) a modeled structure of Fab 121-158 generated by grafting the NMR structure of mouse PrP 124-158 (Rieket (1997) FEBS Lett. 413:282-288) into the crystal structure of IgG1 b12 (Ollmann Saphire et al. (2001) Science 293:1155). Coordinates for PrP residues 121-123 and GG linkers were modeled and refined using TOM/FRODO (Jones (1982) In Computational Crystallography (Sayre, D., ed.), pp. 303 Oxford University Press)). To alleviate possible steric conflict with b12 heavy chain, small variations in the torsion angles of PrP residues 130-134 were introduced. An antibody, designated Fab D18 (described by Williamson et al. (1998) J. Virol. 72:9413-9418; see, SEQ ID NOS:33-36), that recognizes the 133-157 region of PrP only in the presence of the α-helix (residues 145-155), binds well to PrP-Fab 121-158, indicating that the displayed PrP peptide assumes a PrPc-like conformation in at least a fraction of purified Fab 121-158 molecules. As noted, the numbering of residues corresponds to Syrian hamster PrP (SEQ ID NO:5); mouse PrP is set forth in SEQ ID NO:9; 89-112 corresponds to 88-111 of SEQ ID NO:9 from mouse; 136-158 corresponds to 135-157 of SEQ ID NO:9 and 121-158 corresponds to 120-157 of SEQ ID NO:9.

FIG. 2 presents the alignment of exemplary sequences with Syrian golden hamster (top); references to amino acid positions refer to the Syrian hamster residue numbers. The numbering is sequential from top to bottom. The SEQ ID NOS. are as follows:

| | |
|---|---|
| SEQ ID NO: 5 | Syrian hamster |
| SEQ ID NO: 6 | Armenian hamster |
| SEQ ID NO: 7 | Chinese hamster |
| SEQ ID NO: 8 | *Homo sapiens* |
| SEQ ID NO: 9 | Mouse type A |
| SEQ ID NO: 10 | Mouse type B |
| SEQ ID NO: 11 | Sheep |
| SEQ ID NO: 12, | which is not depicted in the FIGURE is sheep R171Q variant; and |
| SEQ ID NO: 13 | bovine. |

FIG. 3 shows densitometric measurement of PrPSc and PrP 27 30 bands identified in an immunoblot showing as a function of concentration demonstrating the high affinity of the polypeptides provided herein for PrPSc and PrP 27-30 (Kd on the order of about 10-9 mol/l; Ka on the order of 109 mol/l); values are given as densitometric units (DU), where 100% is equivalent to the intensity of the bands immunoprecipitated at an antibody concentration of 10 µg/ml.

DETAILED DESCRIPTION

A. Definitions
B. Hybrid molecules
  1. Disease-related polypeptides
    a. Prions
      1) Prions and prion diseases
      2) Hybrid polypeptides containing prions
      3) Sources of prions
      4) Mutations
    b. Other polypeptides
    c. Preparation of hybrid polypeptides
  2. Scaffolds
    a. Antibodies
    b. Other molecules
  3. Exemplary hybrids
C. Nucleic acid molecules, vectors, plasmids, cells and methods for preparation of the hybrid polypeptides
   Plasmids, Vectors and Cells
D. Peptide mimetics
E. Diagnostics, therapeutics, assays and other uses of the hybrid polypeptides
  1. Diagnostics and therapeutics
  2. Drug screening assays
  3. Immobilization and supports or substrates therefor
  4. Standardized Prion Preparation
F. Combinations and kits
G. Examples

A. Definitions

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Figure 2:
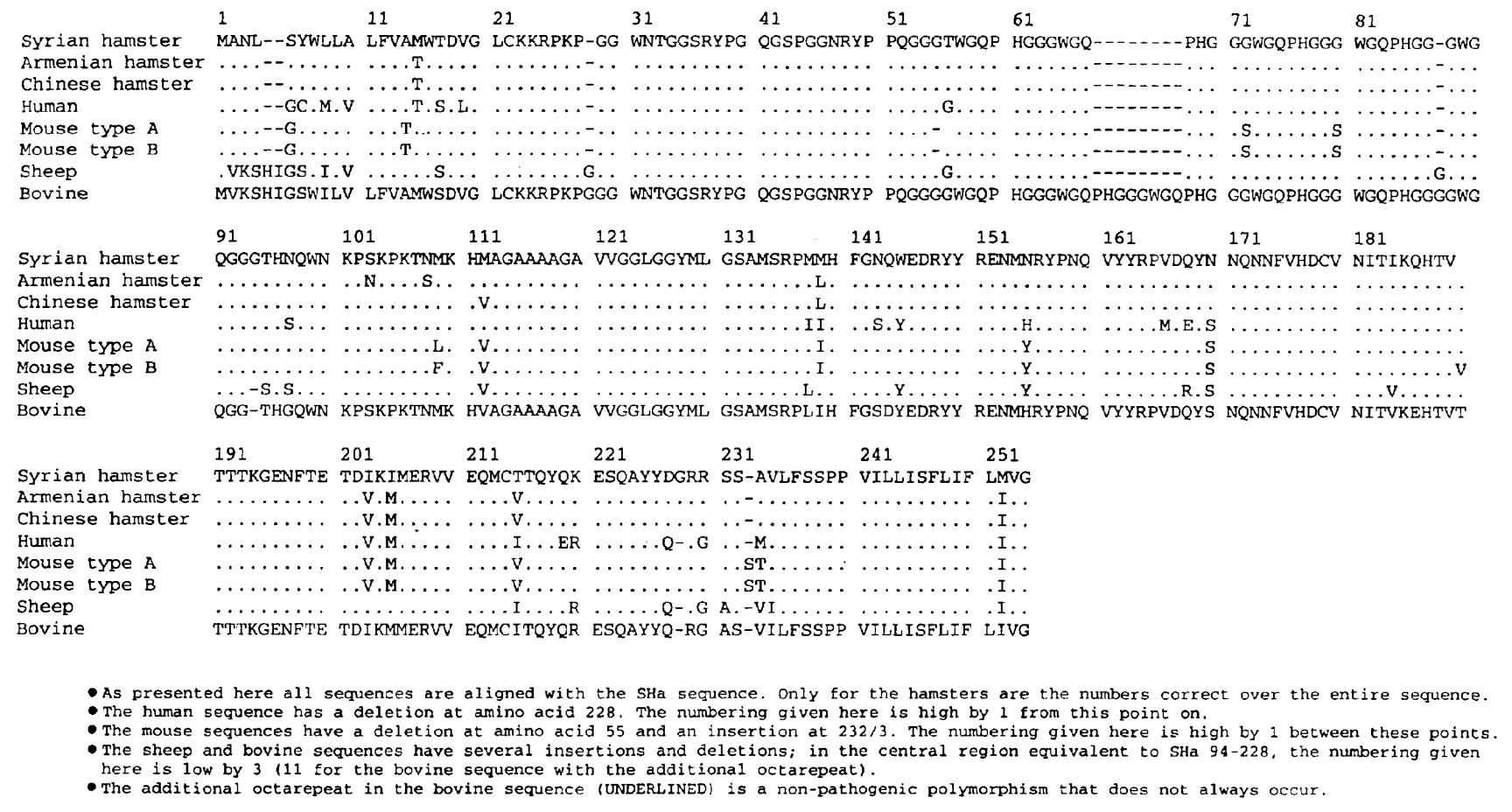

As used herein, reference to amino acid residues in PrP are made with reference to the Syrian hamster sequence (see FIG. 2). The sequence of interest in another species can then be identified by aligning the sequence (see, e.g., FIG. 2) and identifying the corresponding residues. FIG. 2 provides an exemplary alignment. This nomenclature is commonly understood by those of skill in the art.

As used herein, prion gene is any gene of any species that encodes any form of a prion protein ($PrP^c$).

As used herein, reference to PrP 90-231 refers to the portion of PrP remaining after $PrP^{Sc}$ (composed of residues 23-231) is partially digested with proteinase K, which yields PrP 27-30 (approximately corresponding to residues 90-231). Since PrP 27-30 preparations retain prion infectivity, the 90-231 sequence in the $PrP^{Sc}$ conformation is considered the infectious core of PrP. The major component of purified infectious prions, designated PrP 27-30, is the proteinase K resistant core of a larger native protein $PrP^{Sc}$, which is the disease causing form of the ubiquitous cellular protein $PrP^c$. $PrP^{Sc}$ is found only in scrapie infected cells; whereas $PrP^c$ is present in infected and uninfected cells implicating $PrP^{Sc}$ as the major, if not the sole, component of infectious prion particles. Properties distinguishing $PrP^{Sc}$ from $PrP^c$ include low solubility, poor antigenicity, protease resistance and polymerization of PrP 27-30 into rod-shaped aggregates that are very similar, on the ultrastructural and histochemical levels, to the PrP amyloid plaques seen in scrapie diseased brains. By using proteinase K it is possible to denature $PrP^c$ but not $PrP^{Sc}$. $PrP^c$ and $PrP^{Sc}$ are conformational isomers of the same molecule.

As used herein, prion replication refers to the process in which $PrP^c$ is converted to $PrP^{Sc}$. The binding of $PrP^c$ to $PrP^{Sc}$ is a prerequisite in the pathway whereby $PrP^c$ is conformationally rearranged into a molecule of $PrP^{Sc}$.

As used herein, a prion replicative interface is the region of $PrP^c$ that is bound to $PrP^{Sc}$ in the course prion replication.

As used herein, the term "PrP peptide" is any peptide that, when contacted with naturally occurring or recombinant $PrP^{Sc}$ or PrP variant, results in the induction of a conformational change that is identified by the presence of enhanced β-sheet formation, increased insolubility, and/or increased protease resistance, i.e., properties and characteristics of $PrP^{Sc}$. Thus, reference to PrP peptide shall mean a naturally occurring, recombinant, or synthetic polypeptide having a sequence substantially similar (e.g., 70%, 80%, 85%, 90% or greater homology) to a portion of a naturally occurring prion protein sequence including residues that corresponding to 90-231 (SEQ ID NO:5), or a portion thereof, such as 90-145, 121-158, or other portion, and able to bind $PrP^{Sc}$ such that a prion protein complex to produce a polypeptide having one or more of the characteristics of $PrP^{Sc}$. A PrP peptide has at least one α-helical domain and/or has a random coil conformation in a aqueous solution. Further, the PrP peptide can be characterized as having a conformation in aqueous solution which is substantially devoid of β-sheet conformation. The conformation of a PrP peptide can be determined by any method known in the art, including circular dichroism (CD).

A PrP peptide typically has between 1-4α helical domains and binds to $PrP^{Sc}$ to form a prion protein complex. The PrP peptide has the amino acid sequence of any species, such as those set forth in any of SEQ ID NOS:5-13. The PrP peptide can include modifications of the amino acid sequence, such as e.g., but are not limited to, one or more amino acid changes, one or more amino acid deletions, and/or one or more amino acid insertions, so long as it retains the characteristics of having at least one α-helical domain and/or a random coil conformation in an aqueous solution, and, more importantly, binds to $PrP^{Sc}$ to form a prion protein complex. As shown herein, one α-helical domain, however, is not required. The changes, deletions, insertions and other modifications are generally in the sequence between amino acids 90-145, but also includes 89-112. For example, PrP peptide 90-145 (A117V) contains the pathogenic mutation at amino acid residue 117 (alanine to valine) which causes the telencephalic and ataxic forms of GSS disease.

As used herein, conformationally altered protein disease (or a disease of protein aggregation or a disease of protein conformation) refers to diseases associated with a protein or polypeptide that has a disease-associated conformation. Abnormal protein conformation, including, for example, misfolding and aggregation, can lead to a loss or alteration of biological activity. Abnormal protein conformation, including misfolding and aggregation is a causative agent (or contributory agent) in a number of mammalian diseases, including, but are not limited to, cystic fibrosis, Alzheimer's disease, prion spongiform encephalopathies, such as bovine spongiform encephalopathy, scrapie of sheep, Kuru and Creutzfeldt-Jakob disease of humans, including variant, sporadic and iatrogenic, and amyotrophic lateral sclerosis (ALS) (see Table below). Such diseases and associated proteins that assemble two or more different conformations in which at least one conformation is a conformationally altered protein, include those set forth in the following Table 1:

TABLE 1

| Disease | Insoluble protein |
|---|---|
| Alzheimer's Disease (AD) | APP, Aβ, α1-antichymotrypsin, tau, non-Aβ component, presenilin 1, presenilin 2, apoE |
| Prion diseases, including but are not limited to, Creutzfeldt-Jakob disease, scrapie, bovine spongiform encephalopathy | $PrP^{Sc}$ |
| amyotrophic lateral sclerosis (ALS) | superoxide dismutase (SOD) and neurofilament |
| Pick's Disease | Pick body |
| Parkinson's disease | α-synuclein in Lewy bodies |
| Frontotemporal dementia | tau in fibrils |
| Diabetes Type II | amylin |
| Multiple myeloma Plasma cell dyscrasias | IgGL-chain |
| Familial amyloidotic polynueuropathy | Transthyretin |
| Medullary carcinoma of thyroid | Procalcitonin |
| Chronic renal failure | β$_2$-microglobulin |
| Congestive heart failure | Atrial natriuretic factor |
| Senile Cardiac and systemic amyloidosis | transthyretin |
| Chronic inflammation | Serum Amyloid A |
| Atherosclerosis | ApoAl |
| Familial amyloidosis | Gelsolin |
| Huntington's disease | Huntington |

The methods exemplified herein for preparation of a hybrid molecule that specifically binds to the disease-associated conformation of a prion polypeptide can be used to prepare hybrid molecules specific for disease-associated conformations of polypeptides associated with other conformationally altered protein diseases, such as other amyloid diseases.

As used herein, a benign conformer refers to a form of a protein of a disease of protein aggregation or conformation that is not involved with the disease, i.e., does not cause the disease or symptoms thereof.

As used herein, an array refers to a collection of elements, such as antibodies, containing three or more members. An addressable array is one in which the members of the array are identifiable, typically by position on a solid phase support. Hence, in general the members of the array are immobilized on discrete identifiable loci on the surface of a solid phase.

As used herein, a target protein refers to a protein that has a plurality of conformers and is involved or associated with a disease of protein aggregation or conformation.

As used herein, a support (also referred to as a matrix support, a matrix, an insoluble support or solid support) refers to any solid or semisolid or insoluble support to which a molecule of interest, such as hybrid molecules provided herein, is linked or contacted. Such materials include any materials that are used as affinity matrices or supports for chemical and biological molecule syntheses and analyses, such as, but are not limited to: polystyrene, polycarbonate, polypropylene, nylon, glass, dextran, chitin, sand, pumice, agarose, polysaccharides, dendrimers, buckyballs, polyacrylamide, silicon, rubber, and other materials used as supports for solid phase syntheses, affinity separations and purifications, hybridization reactions, immunoassays and other such applications. The matrix herein can be particulate or can be in the form of a continuous surface, such as a microtiter dish or well, a glass slide, a silicon chip, a nitrocellulose sheet, nylon mesh, or other such materials. When particulate, typically the particles have at least one dimension in the 5-10 mm range or smaller. Such particles, referred collectively herein as "beads", are often, but not necessarily, spherical. Such reference, however, does not constrain the geometry of the matrix, which can be any shape, including random shapes, needles, fibers, and elongated. Roughly spherical "beads", particularly microspheres that can be used in the liquid phase, also are contemplated. The "beads" can include additional components, such as magnetic or paramagnetic particles (see, e.g., Dyna beads (Dynal, Oslo, Norway)) for separation using magnets, as long as the additional components do not interfere with the methods and analyses herein.

As used herein, matrix or support particles refers to matrix materials that are in the form of discrete particles. The particles have any shape and dimensions, but typically have at least one dimension that is 100 mm or less, 50 mm or less, 10 mm or less, 1 mm or less, 100 μm or less, 50 μm or less and typically have a size that is 100 $mm^3$ or less, 50 $mm^3$ or less, 10 $mm^3$ or less, and 1 $mm^3$ or less, 100 $\mu m^3$ or less and can be on the order of cubic microns. Such particles are collectively called "beads."

As used herein, an array refers to a collection of elements, such as the hybrid polypeptides, containing three or more members. An addressable array is one in which the members of the array are identifiable, typically by position on a solid phase support or by virtue of an identifiable or detectable label, such as by color, fluorescence, electronic signal (i.e. RF, microwave or other frequency that does not substantially alter the interaction of the molecules or biological particles), bar code or other symbology, chemical or other such label. Hence, in general the members of the array are immobilized to discrete identifiable loci on the surface of a solid phase or directly or indirectly linked to or otherwise associated with the identifiable label, such as affixed to a microsphere or other particulate support (herein referred to as beads) and suspended in solution or spread out on a surface. Thus, for example, positionally addressable arrays can be arrayed on a substrate, such as glass, including microscope slides, paper, nylon or any other type of membrane, filter, chip, glass slide, or any other suitable solid support. If needed the substrate surface is functionalized, derivatized or otherwise rendered capable of binding to a binding partner. In some instances, those of skill in the art refer to microarrays. A microarray is a positionally addressable array, such as an array on a solid support, in which the loci of the array are at high density. For example, a typical array formed on a surface the size of a standard 96 microwell plate with a density of more than about 1550 loci per plate are considered microarrays. In assays provided herein in which molecules are linked to a solid support, they can provided as arrays, including addressable arrays, particularly for high throughput screening protocols.

As used herein, a molecule that specifically binds to a polypeptide typically has a binding affinity ($K_a$) of at least about $10^7$ l/mol, $10^8$ l/mol, $10^9$ l/mol, $10^{10}$ l/mol or greater and binds to a particular conformer of a polypeptide compared to another conformer with a $K_a$ that is at least about 0.5, 1, 5, 10-fold, generally 100-fold or more greater. Thus, for example, exemplified hybrid molecules that bind to $PrP^{Sc}$ interact with an affinity of at least about $10^8$ l/mol or with sufficient affinity to permit detection of bound $PrP^{Sc}$ in an assay therefor; and generally interact with PrP$^{Sc}$ with at least 10-fold, 100-fold or more affinity than with PrP$^c$.

As used herein, animals include any animal, such as, but are not limited to, goats, cows, deer, elk, kudu, horses, camels, llamas, sheep, rodents, pigs and humans. Non-human animals, exclude humans as the contemplated animal.

As used herein, antibody refers to an immunoglobulin, whether natural or partially or wholly synthetically produced, including any derivative thereof that retains the specific binding ability of the antibody. Hence antibody includes any protein having a binding domain that is homologous or substantially homologous to an immunoglobulin binding domain. Antibodies include members of any immunoglobulin class, including IgG, IgM, IgA, IgD and IgE.

As used herein, a hybrid polypeptide refers to a polypeptide that includes regions from at least two sources, such as from an antibody or enzyme or other scaffold that can be a recipient, and a binding motif, such as a polypeptide from a prion protein. The resulting hybrid polypeptides provided herein bind to the infectious conformation or conformation indicative of disease of a polypeptide that exists in more than one isoform, where at least one isoform is involved in a disease or disease process. The recipient scaffold is selected to constrain or permit the motif polypeptide to retain its ability to bind to the targeted polypeptide. The recipient scaffold also can confer additional properties on the hybrid polypeptide, such as the ability to act as a reporter or to capture a reporter moiety. Binding to infectious prions in embodiments herein results from inclusion of a motif, a polypeptide that contains a least residues, generally 10 to 50 or more residues up to substantially a full length prion, from a prion and that is capable of binding to a PrP$^{Sc}$ or PrP$^{Sc}$ complexed to a PrP$^c$.

As used herein, a polypeptide motif refers to a sequence of amino acids that are derived from a protein that recognizes an altered, generally abnormal (i.e. disease-causing), conformation and retains the specificity, although the affinity can be reduced, of the whole protein. The protein with the altered conformation can be transmissible, such as the PrP$^{Sc}$ form of the prion. The polypeptide motif is grafted (i.e., inserted) into a scaffold (typically a polypeptide). As shown herein, the motif can be derived from residues from the target polypeptide that are involved in the aggregation reaction or that induce or are involved in the change in conformation. Upon insertion, additional amino acids, such as neutral amino acids, including Gly and/or Ser can be included, typically one to a few residues at either end. The motif can be inserted into another polypeptide or can replace a portion thereof that is larger, smaller or about the same size as the motif.

As used herein, a scaffold refers to a recipient molecule for receiving the grafted motif. The scaffold is selected so that the grafted motif retains is desired activity. The scaffold can possess activity, such as binding affinity or enzymatic activity or can have no activity or be modified to eliminate an activity. Scaffolds include, but are not limited to, enzymes or portions thereof that retain binding and/or catalytic activity, fluorescent proteins or portions thereof that retain activity and/or that permit the grafted portion to retain activity and/or that permit the grafted portion to retain activity, antibodies or portions thereof that retain binding activity and/or that permit the grafted portion to retain the desired activity. The scaffold is provided to graft in a polypeptide motif that binds to an epitope on an infectious or disease-causing form of an agent of a disease of protein aggregation to produce a hybrid molecule that binds with greater affinity to an infectious or disease-causing form of an agent of a disease of protein aggregation than to a benign form (or vice versa).

As used herein, "reporter" or "reporter moiety" refers to any moiety that allows for the detection of a molecule of interest, such as a protein or the hybrid polypeptides provided herein. A reporter molecule refers to a molecule, such as an enzyme or indicator, which is capable of generating a detectable signal (e.g., by colorimetric, chemiluminescent, bioluminescent, fluorescent, or potentiometric means) when contacted with a suitable substrate or detection means under appropriate conditions. Exemplary reporter enzymes include, but are not limited to, alkaline phosphatase, luciferase and photoproteins, such as aequora and renilla species luciferases/photoproteins, firefly luciferase (deWet et al. (1987) *Mol. Cell. Biol.* 7:725-737); bacterial luciferase (Engebrecht and Silverman (1984) *Proc. Natl. Acad. Sci. U.S.A.* 81:4154-4158; Baldwin et al. (1984) *Biochemistry* 23:3663-3667); other enzymes such as beta-galactosidase; alkaline phosphatase (Toh et al. (1989) *Eur. J. Biochem.* 182:231-238, Hall et al. (1983) *J. Mol. App/Gen.* 2:101); chemiluminescence generators, such as horseradish peroxidase, aryl esterase, sulfatase and urease. Other reporter moieties include, for example, luminescent moieties, such as fluorescent proteins (FPs), including, but are not limited to, red, blue and green fluorescent proteins and variants thereof.

As used herein, a luminescent label is a label that emits or absorbs EM radiation. Exemplary luminescence labels include, but are not limited to, fluorophores, including fluorescent proteins, quenchers of fluorescence and bioluminescence and other chemiluminescence generating systems.

As used herein, "fluorescence" refers to luminescence (emission of light) that is caused by the absorption of radiation at one wavelength ("excitation"), followed by nearly immediate re-radiation ("emission"), usually at a different wavelength, that ceases almost at once when the incident radiation stops. At a molecular level, fluorescence occurs as certain compounds, known as fluorophores, are taken from a ground state to a higher state of excitation by light energy; as the molecules return to their ground state, they emit light, typically at a different wavelength (Lakowicz, J. R., Principles of Fluorescence Spectroscopy, New York:Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.) "Phosphorescence," in contrast, refers to luminescence that is caused by the absorption of radiation at one wavelength followed by a delayed re-radiation that occurs at a different wavelength and continues for a noticeable time after the incident radiation stops.

As used herein, chemiluminescence refers to luminescence resulting from a chemical reaction.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen and transforms the substrate to an excited state, which upon return to a lower energy level releases the energy in the form of light.

As used herein, the biomolecules for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, luciferase refers to oxygenases that catalyze a light emitting reaction. For instance, bacterial luciferases catalyze the oxidation of flavin mononucleotide (FMN) and aliphatic aldehydes, which reaction produces light. Another class of luciferases, found among marine arthropods, catalyzes the oxidation of *Cypridina* (*Vargula*) luciferin, and another class of luciferases catalyzes the oxidation of Coleoptera luciferin.

Thus, luciferase refers to an enzyme or photoprotein that catalyzes a bioluminescent reaction (a reaction that produces bioluminescence). The luciferases, such as firefly and *Gaussia* and *Renilla* luciferases, that are enzymes which act catalytically and are unchanged during the bioluminescence generating reaction. The luciferase photoproteins, such as the aequorin photoprotein to which luciferin is non-covalently bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases. Luciferases can serve as scaffolds for grafting a polypeptide that binds to an epitope on an infectious or disease-causing form of an agent of a disease of protein aggregation to produce a hybrid molecule that binds with greater affinity to an infectious or disease-causing form of an agent of a disease of protein aggregation than to a benign form (or vice versa).

The luciferases and luciferin and activators thereof are referred to as bioluminescence generating reagents or components. Thus, as used herein, the component luciferases, luciferins, and other factors, such as $O_2$, $Mg^{2+}$, $Ca^{2+}$ are also referred to as bioluminescence generating reagents (or agents or components). The combination of all such components is a bioluminescence generating system. Similarly, all components of a system for generating chemiluminescence is a chemiluminescence generating system.

As used herein, a hybrid antibody refers to an antibody or fragment thereof that includes a non-immunoglobulin-derived portion or portions, such as the hybrid polypeptides provided herein in which a portion of an immunoglobulin or Fab is replaced with another polypeptide that binds to a targeted polypeptide involved in a disease of protein aggregation. For convenience herein the hybrid molecules are referred to as Fab's or as immunoglobulin, such as an IgG, but it is understood that such hybrid molecules are not Fab's or Igs per se, but include grafted portions that confer specificity.

As used herein, antibody fragment refers to any derivative of an antibody that is less then full-length, retaining at least a portion of the full-length antibody's specific binding ability. Examples of antibody fragments include, but are not limited to, Fab, Fab', $F(ab)_2$, single-chain Fvs (scFV), FV, dsFV diabody and Fd fragments. The fragment can include multiple chains linked together, such as by disulfide bridges. An antibody fragment generally contains at least about 50 amino acids and typically at least 200 amino acids.

As used herein, an Fv antibody fragment is composed of one variable heavy domain ($V_H$) and one variable light domain linked by noncovalent interactions.

As used herein, a dsFV refers to an Fv with an engineered intermolecular disulfide bond, which stabilizes the $V_H$-$V_L$ pair.

As used herein, an $F(ab)_2$ fragment is an antibody fragment that results from digestion of an immunoglobulin with pepsin at pH 4.0-4.5; it can be recombinantly expressed to produce the equivalent fragment.

As used herein, Fab fragments are antibody fragments that result from digestion of an immunoglobulin with papain; they can be recombinantly expressed to produce the equivalent fragment.

As used herein, scFVs refer to antibody fragments that contain a variable light chain ($V_L$) and variable heavy chain ($V_H$) covalently connected by a polypeptide linker in any order. The linker is of a length such that the two variable domains are bridged without substantial interference. Included linkers are (Gly-Ser)$_n$ residues with some Glu or Lys residues dispersed throughout to increase solubility.

As used herein, humanized antibodies refer to antibodies that are modified to include human sequences of amino acids so that administration to a human does not provoke an immune response. Methods for preparation of such antibodies are known. For example, to produce such antibodies, the hybridoma or other prokaryotic or eukaryotic cell, such as an *E. coli* or a CHO cell, that expresses the monoclonal antibody are altered by recombinant DNA techniques to express an antibody in which the amino acid composition of the non-variable region is based on human antibodies. Computer programs have been designed to identify such regions.

As used herein, diabodies are dimeric scFV; diabodies typically have shorter peptide linkers than scFvs, and they generally dimerize.

As used herein, hsFv refers to antibody fragments in which the constant domains normally present in an Fab fragment have been substituted with a heterodimeric coiled-coil domain (see, e.g., Arndt et al. (2001) *J Mol Biol.* 7:312:221-228).

As used herein, sample refers to anything which can contain an analyte for which an analyte assay is desired. The sample can be a biological sample, such as a biological fluid or a biological tissue. Examples of biological fluids include urine, blood, plasma, serum, saliva, semen, stool, sputum, cerebral spinal fluid, tears, mucus, sperm, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include, for example, organs, tumors, lymph nodes, arteries and individual cell(s).

As used herein, biological sample refers to any sample obtained from a living or viral source and includes any cell type or tissue of a subject from which nucleic acid or protein or other macromolecule can be obtained. Biological samples include, but are not limited to, body fluids, such as blood, plasma, serum, cerebrospinal fluid, synovial fluid, urine and sweat, tissue and organ samples from animals and plants. Also included are soil and water samples and other environmental samples, viruses, bacteria, fungi, algae, protozoa and components thereof. Hence bacterial and viral and other contamination of food products and environments can be assessed. The methods herein are practiced using biological samples and in some embodiments, such as for profiling, also can be used for testing any sample.

As used herein, a drug identified by the screening methods provided herein refers to any compound that is a candidate for use as a therapeutic or as a lead compound for the design of a therapeutic. Such compounds can be small molecules, including small organic molecules, peptides, peptide mimetics, antisense molecules or dsRNA, such as RNAi, antibodies, fragments of antibodies, recombinant antibodies and other such compounds that can serve as drug candidates or lead compounds.

As used herein, a peptidomimetic is a compound that mimics the conformation and certain stereochemical features of the biologically active form of a particular peptide. In general, peptidomimetics are designed to mimic certain desirable properties of a compound, but not the undesirable properties, such as flexibility, that lead to a loss of a biologically active conformation and bond breakdown. Peptidomimetics can be prepared from biologically active compounds by replacing certain groups or bonds that contribute to the undesirable properties with bioisosteres. Bioisosteres are known to those of skill in the art. For example the methylene bioisostere $CH_2S$ has been used as an amide replacement in enkephalin analogs (see, e.g., Spatola (1983) pp. 267-357 in *Chemistry and Biochemistry of Amino Acids, Peptides, and Proteins*, Weistein, Ed. volume 7, Marcel Dekker, New York). Morphine, which can be administered orally, is a compound that is a peptidomimetic of the peptide endorphin. For purposes herein, cyclic peptides are included among peptidomimetics.

As used herein, macromolecule refers to any molecule having a molecular weight from the hundreds up to the millions. Macromolecules include peptides, proteins, nucleotides, nucleic acids, and other such molecules that are generally synthesized by biological organisms, but can be prepared synthetically or using recombinant molecular biology methods.

As used herein, the term "biopolymer" is used to mean a biological molecule, including macromolecules, composed of two or more monomeric subunits, or derivatives thereof, which are linked by a bond or a macromolecule. A biopolymer can be, for example, a polynucleotide, a polypeptide, a carbohydrate, or a lipid, or derivatives or combinations thereof, for example, a nucleic acid molecule containing a peptide nucleic acid portion or a glycoprotein, respectively. Biopolymer includes, but are not limited to, nucleic acid, proteins, polysaccharides, lipids and other macromolecules. Nucleic acids include DNA, RNA, and fragments thereof. Nucleic acids can be derived from genomic DNA, RNA, mitochondrial nucleic acid, chloroplast nucleic acid and other organelles with separate genetic material.

As used herein, a biomolecule is any compound found in nature, or derivatives thereof. Biomolecules include but are not limited to: oligonucleotides, oligonucleosides, proteins, peptides, amino acids, peptide nucleic acids (PNAs), oligosaccharides and monosaccharides.

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and other such analogs and derivatives or combinations thereof. The term should be understood to include, as equivalents, derivatives, variants and analogs of either RNA or DNA made from nucleotide analogs, single (sense or antisense) and double-stranded polynucleotides. Deoxyribonucleotides include deoxyadenosine, deoxycytidine, deoxyguanosine and deoxythymidine. For RNA, the uracil base is uridine.

Nucleotide analogs contained in a polynucleotide can be, for example, mass modified nucleotides, which allows for mass differentiation of polynucleotides; nucleotides containing a detectable label such as a fluorescent, radioactive, luminescent or chemiluminescent label, which allows for detection of a polynucleotide; or nucleotides containing a reactive group such as biotin or a thiol group, which facilitates immobilization of a polynucleotide to a solid support. A polynucleotide also can contain one or more backbone bonds that are selectively cleavable, for example, chemically, enzymatically or photolytically. For example, a polynucleotide can include one or more deoxyribonucleotides, followed by one or more ribonucleotides, which can be followed by one or more deoxyribonucleotides, such a sequence being cleavable at the ribonucleotide sequence by base hydrolysis. A polynucleotide also can contain one or more bonds that are relatively resistant to cleavage, for example, a chimeric oligonucleotide primer, which can include nucleotides linked by peptide nucleic acid bonds and at least one nucleotide at the 3' end, which is linked by a phosphodiester bond or other suitable bond, and is capable of being extended by a polymerase. Peptide nucleic acid sequences can be prepared using well known methods (see, for example, Weiler et al., *Nucleic acids Res.* 25:2792-2799 (1997)).

As used herein, oligonucleotides refer to polymers that include DNA, RNA, nucleic acid analogs, such as PNA, and combinations thereof. For purposes herein, primers and probes are single-stranded oligonucleotides or are partially single-stranded oligonucleotides. The term "polynucleotide" refers to an oligomer or polymer containing at least two linked nucleotides or nucleotide derivatives, including a deoxyribonucleic acid (DNA), a ribonucleic acid (RNA), and a DNA or RNA derivative containing, for example, a nucleotide analog or a "backbone" bond other than a phosphodiester bond, for example, a phosphotriester bond, a phosphoramidate bond, a phosphorothioate bond, a thioester bond, or a peptide bond (peptide nucleic acid). The term "oligonucleotide" also is used herein essentially synonymously with "polynucleotide," although those in the art recognize that oligonucleotides, for example, PCR primers, generally are less than about fifty to one hundred nucleotides in length.

As used herein, test substance (or test compound) refers to a chemically defined compound (e.g., organic molecules, inorganic molecules, organic/inorganic molecules, proteins, peptides, nucleic acids, oligonucleotides, lipids, polysaccharides, saccharides, or hybrids among these molecules such as glycoproteins, etc.) or mixtures of compounds (e.g., a library of test compounds, natural extracts or culture supernatants, etc.) whose effect on an SP, particularly a single chain form that includes the protease domain or a sufficient portion thereof for activity, as determined by an in vitro method, such as the assays provided herein, is tested. Test compounds can be provided as libraries (collections) of such compounds.

As used herein, high-throughput screening (HTS) is a process of testing a large number of diverse chemical structures (libraries of compounds) against targets to identify "hits" (Sittampalam et al., *Curr. Opin. Chem. Biol.*, 1:384-91 (1997)). HTS operations can be automated and computerized to handle sample preparation, assay procedures and the subsequent processing of large volumes of data.

As used herein, production by recombinant means by using recombinant DNA methods means the use of the well known methods of molecular biology for expressing proteins encoded by cloned DNA.

As used herein, substantially identical to a product means sufficiently similar so that the property of interest is sufficiently unchanged so that the substantially identical product can be used in place of the product.

As used herein, equivalent, when referring to two sequences of nucleic acids, means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions (see, e.g., Table 1, above) that do not substantially alter the activity or function of the protein or peptide. When "equivalent" refers to a property, the property does not need to be present to the same extent but the activities are generally substantially the same. "Complementary," when referring to two nucleotide sequences, means that the two sequences of nucleotides are capable of hybridizing, generally with less than 25%, with less than 15%, and even with less than 5% or with no mismatches between opposed nucleotides. Generally to be considered complementary herein the two molecules hybridize under conditions of high stringency.

The term "substantially" identical or homologous or similar varies with the context as understood by those skilled in the relevant art and means at least 70%, typically means at least 80%, 90%, and most generally at least 95% identity. Where necessary the percentage identity will be specified.

As used herein, by homologous means about greater than 25% nucleic acid sequence identity, such as 25% 40%, 60%, 70%, 80%, 90% or 95%. If necessary the percentage homology will be specified. The terms "homology" and "identity" are often used interchangeably. In general, sequences are aligned so that the highest order match is obtained (see, e.g.: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part I*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; Carillo et al. (1988) *SIAM J Applied Math* 48:1073). By sequence identity, the number of conserved amino acids are determined by standard alignment algorithms programs, and are used with default gap penalties established by each supplier. Substantially homologous nucleic acid molecules would hybridize typically at moderate stringency or at high stringency all along the length of the nucleic acid or along at least about 70%, 80% or 90% of the full-length nucleic acid molecule of interest. Also contemplated are nucleic acid molecules that contain degenerate codons in place of codons in the hybridizing nucleic acid molecule.

Whether any two nucleic acid molecules have nucleotide sequences that are at least, for example, 80%, 85%, 90%, 95%, 96%, 97%, 98% or 99% "identical" can be determined using known computer algorithms such as the "FAST A" program, using for example, the default parameters as in Pearson et al. (1988) *Proc. Natl. Acad. Sci. USA* 85:2444 (other programs include the GCG program package (Devereux, J., et al., *Nucleic Acids Research* 12(I):387 (1984)), BLASTP, BLASTN, FASTA (Atschul, S.F., et al., *J Molec Biol* 215:403 (1990); Guide to Huge Computers, Martin J. Bishop, ed., Academic Press, San Diego, 1994, and Carillo et al. (1988) *SIAM J Applied Math* 48:1073). For example, the BLAST function of the National Center for Biotechnology Information database can be used to determine identity. Other commercially or publicly available programs include, DNAStar "MegAlign" program (Madison, Wis.) and the University of Wisconsin Genetics Computer Group (UWG) "Gap" program (Madison Wis.)). Percent homology or identity of proteins and/or nucleic acid molecules can be determined, for example, by comparing sequence information using a GAP computer program (e.g., Needleman et al. (1970) *J. Mol. Biol.* 48:443, as revised by Smith and Waterman ((1981) *Adv. Appl. Math.* 2:482). Briefly, the GAP program defines similarity as the number of aligned symbols (i.e., nucleotides or amino acids) which are similar, divided by the total number of symbols in the shorter of the two sequences. Default parameters for the GAP program can include: (1) a unary comparison matrix (containing a value of 1 for identities and O for non-identities) and the weighted comparison matrix of Gribskov et al. (1986) *Nucl. Acids Res.* 14:6745, as described by Schwartz and Dayhoff, eds., *ATLAS OF PROTEIN SEQUENCE AND STRUCTURE*, National Biomedical Research Foundation, pp. 353-358 (1979); (2) a penalty of 3.0 for each gap and an additional 0.10 penalty for each symbol in each gap; and (3) no penalty for end gaps. Therefore, as used herein, the term "identity" represents a comparison between a test and a reference polypeptide or polynucleotide.

As used herein, the term at least "90% identical to" refers to percent identities from 90 to 99.99 relative to the reference polypeptides. Identity at a level of 90% or more is indicative of the fact that, assuming for exemplification purposes a test and reference polynucleotide length of 100 amino acids are compared. No more than 10% (i.e., 10 out of 100) amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g. 10/100 amino acid difference (approximately 90% identity). Differences are defined as nucleic acid or amino acid substitutions, or deletions. At the level of homologies or identities above about 85-90%, the result should be independent of the program and gap parameters set; such high levels of identity can be assessed readily, often without relying on software.

As used herein, to hybridize under conditions of a specified stringency is used to describe the stability of hybrids formed between two single-stranded DNA fragments and refers to the conditions of ionic strength and temperature at which such hybrids are washed, following annealing under conditions of stringency less than or equal to that of the washing step. Typically high, medium and low stringency encompass the following conditions or equivalent conditions thereto:

1) high stringency: 0.1×SSPE or SSC, 0.1% SDS, 65° C.
2) medium stringency: 0.2×SSPE or SSC, 0.1% SDS, 50° C.
3) low stringency: 1.0×SSPE or SSC, 0.1% SDS, 50° C.

Equivalent conditions refer to conditions that select for substantially the same percentage of mismatch in the resulting hybrids. Additions of ingredients, such as formamide, Ficoll, and Denhardt's solution affect parameters such as the temperature under which the hybridization should be conducted and the rate of the reaction. Thus, hybridization in 5×SSC, in 20% formamide at 42° C. is substantially the same as the conditions recited above hybridization under conditions of low stringency. The recipes for SSPE, SSC and Denhardt's and the preparation of deionized formamide are described, for example, in Sambrook et al. (1989) *Molecular Cloning, A Laboratory Manual*, Cold Spring Harbor Laboratory Press, Chapter 8; see, Sambrook et al., vol. 3, p. B.13, see, also, numerous catalogs that describe commonly used laboratory solutions). It is understood that equivalent stringencies can be achieved using alternative buffers, salts and temperatures.

As used herein, a composition refers to any mixture. It can be a solution, a suspension, liquid, powder, a paste, aqueous, non-aqueous or any combination thereof.

As used herein, a combination refers to any association between among two or more items. The combination can be two or more separate items, such as two compositions or two collections, can be a mixture thereof, such as a single mixture of the two or more items, or any variation thereof.

As used herein, kit refers to a packaged combination, optionally including instructions and/or reagents for their use.

As used herein, "package" refers to a solid material such as glass, plastic (e.g., polyethylene, polypropylene and polycarbonate), paper, foil for holding within fixed limits a reagent. Thus, for example, a package can be a bottle, vial, plastic and plastic-foil laminated envelope or the like container used to contain a contemplated diagnostic reagent or it can be a microtiter plate well to which microgram quantities of a contemplated diagnostic reagent have been operatively affixed, i.e., linked so as to be capable of being immunologically bound by a hybrid polypeptide or target polypeptide.

As used herein, fluid refers to any composition that can flow. Fluids thus encompass compositions that are in the form of semi-solids, pastes, solutions, aqueous mixtures, gels, lotions, creams and other such compositions.

As used herein, suitable conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224).

Such substitutions can be made in accordance with those set forth in TABLE 2 as follows:

TABLE 2

| | |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu |

Other substitutions also are permissible and can be determined empirically or in accord with known conservative substitutions.

As used herein, the amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

Other abbreviations used herein include, but are not limited to: CNS for central nervous system; BSE for bovine spongiform encephalopathy; CJD for Creutzfeldt-Jakob Disease; FFI for fatal familial insomnia; GSS for Gerstmann-Straussler-Scheinker Disease; Hu for human; HuPrP for a human prion protein (SEQ ID NO:8) Mo for mouse; MoPrP for a mouse prion protein (SEQ ID NO:9 and SEQ ID NO:10); SHa for a Syrian hamster; SHaPrP for a Syrian hamster prion protein (SEQ ID NO:5); Tg for transgenic; Tg(SHaPrP) for a transgenic mouse containing the PrP gene of a Syrian hamster; Tg(HuPrP) for transgenic mice containing a human PrP gene; Tg(ShePrP) for transgenic mice containing the complete sheep PrP gene (SEQ ID NO:11); Tg(BovPrP) for transgenic mice containing the complete cow PrP gene (SEQ ID NO:13); PrP$^{Sc}$ for the scrapie isoform of the prion protein; PrP$^c$ for the cellular normal isoform of the prion protein; and MoPrP$^{Sc}$ for the scrapie isoform of the mouse prion protein.

B. Hybrid Molecules

For disease of protein conformation the same protein (or a portion thereof) exhibits more than one isoform (conformer) such that at least one form is causative of a disease, such as the prion protein or an amyloid protein, or is involved in the disease. For purposes of diagnosis, prognosis, therapy and or drug screening it is advantageous to have molecules that specifically interact (i.e. react with greater affinity, typically at least, 2-, 5-10-fold, generally at least about 100-fold) with a disease-associated conformer than with a benign (non-disease involved) conformer (or vice versa). Hence provided herein are molecules that specifically react with one conformer of a protein that has a plurality of conformers. Typically the molecules interact with a disease-associated conformer.

In particular, provided herein are hybrid molecules, such as hybrid polypeptides, that include a polypeptide motif or polypeptide that includes such motif, and additional amino acid residues (typically, 5, 10, 15, 20, 30, 40, 50, 100 or more) such that the resulting hybrid molecule specifically interacts with one conformer. The polypeptide generally includes a contiguous sequence of amino acids (a motif) from the protein that exhibits the conformations. The motif can be modified, such as by replacing certain amino acids or by directed and random evolution methods, to produce motifs with greater affinity.

Thus, among the hybrid molecules provided herein are hybrid molecules, particularly hybrid polypeptides, that are produced by grafting a binding motif from one molecule into a scaffold, such as an antibody or fragment thereof or an enzyme or other reporter molecule. The hybrid polypeptides provided herein, even the hybrid immunoglobulins, are not antibodies per se, but are polypeptides that are hybrid molecules containing a selected motif inserted into another polypeptide such that the motif retains or obtains the ability to bind to a protein involved in disease of protein aggregation. The hybrid polypeptides can include portions of antibodies or other scaffolds, but they also include a non-immunoglobulin or non-scaffold portion grafted therein. The non-immunoglobulin portion is identified by its ability to specifically bind to a targeted polypeptide isoform. The hybrid polypeptide can specifically bind to the targeted infectious or disease-related or a selected isoform of a polypeptide as monomer with sufficient affinity to detect the resulting complex or to precipitate the targeted polypeptide.

The scaffold is selected so that insertion of the motif therein does not substantially alter (i.e., retains) the desired binding specificity of the motif. The scaffold additionally can be selected for its properties, such as its ability to act as a reporter. It also can be modified by elimination of portions thereof to eliminate an activity or binding specificity thereof.

The scaffold also can serve to constrain the polypeptide into its proper 3-D structure for reactivity with a target polypeptide.

Methods for production of hybrid molecules that specifically interact with a one form of a conformer of a protein associated with a disease of protein conformation or involving protein aggregation are provided. In these methods a polypeptide motif from the protein is inserted into a scaffold such that the resulting molecule exhibits specific binding to one conformer compared to other conformers. In particular, the hybrid molecule can exhibit specific binding to a disease associated conformer or an aggregating conformer compared to a benign conformer.

Methods for production of the hybrid molecules, such as hybrid polypeptides, and the resulting hybrid molecules are exemplified using the infectious form of the prion as a target and epitopes and regions thereof as motifs. Specifically exemplified are several hybrid polypeptides that interact with substantially greater affinity (at least 10-fold greater) with the native infectious form (or infectious core thereof) of a prion polypeptide than the non-infectious form. It is shown herein that at least two distinct epitopes on the PrP polypeptide are recognized by the hybrid polypeptides (also referred to herein as grafted antibodies).

1. Disease-Related Proteins or Polypeptides

As noted above, the methods and hybrid molecules herein employ proteins that are involved in or are associated with diseases of protein aggregation or conformation. In such diseases, at least one form of a protein is benign and another is involved in the disease, such as, as an infectious agent of the disease and/or in an aggregation reaction. Such diseases and associated proteins that assemble two or more different conformations in which at least one conformation is a conformationally altered protein, include those set forth in the Table 1 above.

a. Prions $PrP^{Sc}$, an abnormal conformer of the ubiquitous cellular prion protein ($PrP^c$), is the only identified constituent of infectious prion particles. During prion propagation, the formation of nascent prion infectivity is thought to proceed via a template-dependent process in which $PrP^{Sc}$ self-replicates by driving the conformational rearrangement of $PrP^c$. Exactly how the distinct $PrP^c$ and $PrP^{Sc}$ conformers interact with one another, and possibly other auxiliary molecules (Kaneko et al. (1998) *Proc. Natl. Acad. Sci. U.S.A.* 94:10069-10074; Zulianello et al. (2000) *J. Virol.* 74:4351-4360) in the prion replicative complex is unknown. The observation that different prion strains retain their characteristic properties over multiple passages indicates that prion propagation is a high fidelity process, and suggests molecular interactions between $PrP^c$ and $PrP^{Sc}$ are extremely specific (Prusiner et al. (1998) *Proc. Natl. Acad. Sci. U.S.A.* 95:13363-13383; Caughey (2001) *T.I.B.S.* 26:235-242).

1) Prions and Prion Diseases

Prion diseases such as scrapie and bovine spongiform encephalopathy are intimately linked with $PrP^{Sc}$, an abnormal conformer of the cellular prion protein ($PrP^C$). Monoclonal antibodies that bind to the first α-helix of $PrP^c$, such as monoclonal antibody D13 or D18, inhibit prion propagation by preventing heterodimeric association of $PrP^c$ and $PrP^{Sc}$ (see, Williamson et al. (1998) *J. Virol.* 72:9413-9418; see, also copending U.S. application Ser. No. 09/627, 218; see, SEQ ID NOS:29-36, which set forth the nucleic acid and encoded protein sequences of the heavy and light chains of each of these Fabs). Antibodies or other specific binding molecules that distinguish between $PrP^c$ and $PrP^{Sc}$ can be of value in resolving this problem. Immunization of normal or PrP-null animals with a wide range of PrP antigens including infectious prions, $PrP^c$, and recombinant and synthetic PrP molecules refolded into α-helical or β-sheet-rich conformations, however, has repeatedly failed to elicit high-affinity antibodies that exclusively recognize disease-associated forms of PrP (Williamson et al. *Proc. Natl. Acad. Sci. U.S.A.* 93:7279; Peretz et al. (1997) *J. Mol. Biol.* 273:614; Williamson et al. (1998) *J. Virol.* 72:9413). An earlier report (Korth et al. (1997) Nature 390:74) of such an antibody has proven premature (Fischer (2000) *Nature* 408:479).

Prion propagation is a template-dependent process in which $PrP^{Sc}$ drives the conformational rearrangement of $PrP^c$ (Prusiner et al. (1998) *Proc. Natl. Acad. Sci. U.S.A.* 95:13363-13383). Exactly how these two distinct PrP conformers interact in the prion replicative complex is unknown.

Monoclonal antibodies reacting with different epitopes of $PrP^c$ are reported to efficiently inhibit prion propagation in a scrapie prion-infected neuroblastoma line (Peretz et al. (2001) *Nature* 412:739-743). The observed inhibitory effect appears to result from antibody binding to cell surface $PrP^c$ that hinders docking of $PrP^{Sc}$ template or a cofactor critical for conversion of $PrP^c$ to $PrP^{Sc}$. One of the antibodies used in these experiments, Fab D18, possesses a particularly potent inhibitory effect (Williamson et al. (1998) *J. Virol.* 72:9413-941'8). As indicated herein, its discontinuous $PrP^c$ epitope, which spans residues 133-157 plays an important role in binding directly to $PrP^{Sc}$. D13 Fab also has a potent inhibitory effect.

2) Hybrid Polypeptides Containing Prion Polypeptides or Motifs Therefrom

Provided herein are polypeptides that specifically bind to $PrP^{Sc}$ and methods of preparing such polypeptides and other hybrid polypeptides that bind to infectious or disease-causing conformers of conformationally altered protein diseases (diseases involving protein aggregation). Hence provided are polypeptides that preferentially (specifically) bind to one conformer (generally the disease-associated conformer) with greater affinity, typically at least 0.5, 1, 2, 3, 5, 10-fold or greater, than to the other conformer. Also contemplated are peptides containing deletions of one or more amino acids that result in the modification of the structure of the resultant molecule but do not significantly altering its ability to bind to one conformer, such as $PrP^{Sc}$ to form a prion protein complex or to induce a conformational change in one conformer, such as induction of a conformational change in $PrP^{Sc}$.

Provided herein are regions of $PrP^c$ that are critical components of the $PrP^c$-$PrP^{Sc}$ replicative interface. In accord with the methods provided herein, the PrP polypeptide that corresponds to this region is grafted into a suitable carrier molecule or scaffold, such as an antibody or fragment thereof, to produce a molecule with specific recognition of disease-associated forms of PrP. The molecules provided herein are hybrid molecules, such as an immunoglobulin or Fab or other antibody fragment with a region replaced by prion sequence. The resulting molecule is a multivalent, such as divalent, or monovalent molecule that specifically binds to the $PrP^{Sc}$. In embodiments herein, the binding molecules have non-immunoglobulin polypeptide grafted into regions, particularly regions such as the CD3R region, that retain the appropriate PrP conformation of the grafted PrP. The methods for making the hybrid molecules and the resulting hybrid molecules can be used to specifically bind to the complexed or conformationally altered form of a polypeptide that participates in diseases of aggregation. The hybrid molecules can be used, for example, for diagnosis and screening.

Provided herein are molecules that specifically bind to or interact with $PrP^{Sc}$. PrP sequence motifs were grafted into recipient antibody scaffolds (IgG and Fabs) and shown (see EXAMPLES) to bind to non-denatured $PrP^{Sc}$ and to PrP 27-30. The hybrid polypeptides are specific for the infectious form and not the normal form. The molecules interact as divalent or monomeric molecules and are capable of specifically binding as a monomeric binding site. They generally are hybrid polypeptides that contain a prion-derived portion and a scaffold, such as an antibody or fragment thereof.

Any prion or portion thereof is grafted into a selected recipient scaffold. The selected portion can be empirically determined by systematically grafting the entire molecule and portions thereof and testing for the ability to specifically bind to $PrP^{Sc}$. Smaller and smaller regions can be selected until the binding affinity diminishes to an unacceptable level (typically less than $10^6$-$10^7$ l/mol).

The methods provided herein can be used to produce a large variety of hybrid polypeptides with specificity for a targeted protein, particularly one involved in diseases and disorders involving protein aggregation, such as amyloid disorders. Regions of a polypeptide that bind to the disease-related form of the targeted polypeptide are systematically grafted into a suitable scaffold, and the resulting hybrid polypeptides that bind specifically (i.e., with an affinity of at least about $10^7$ l/mol and/or 10-fold, 100-fold or more-fold greater than to a non-disease related isoform of the protein) are identified.

For example, hybrid polypeptides that bind only to a prion protein naturally occurring within a single species and not to a prion protein naturally occurring within other species can be produced. Further, the hybrid polypeptide can be designed to bind only to an infectious form of a prion protein (e.g., $PrP^{Sc}$) and not bind to a non-infectious form (e.g., $PrP^c$). A single one or a plurality can then be used in assays to identify or detect a particular target protein.

The hybrid polypeptide can be purified and isolated using known techniques and bound to a support using known procedures. The resulting surface can be used to assay samples, such as blood or other body fluid or samples from organs and tissues, in vitro to determine if the sample contains one or more types of target proteins. For example, hybrid polypeptides that specifically bind only to human $PrP^{Sc}$ can be attached to the surface of a support and a sample contacted with the hybrid polypeptides bound to the surface of material. If no binding occurs it can be deduced that the sample does not contain human $Prp^{Sc}$ The hybrid polypeptides also can have ability to neutralize prions (i.e., eliminate their infectivity). Thus, compositions containing the hybrid polypeptides can be added to a product, such as blood or food, in order to neutralize any infectious prion protein within the product. Thus, if a product is produced from a natural source that might contain infectious prion proteins, the hybrid polypeptides can be added as a precaution thereby eliminating any potential infection resulting from infectious prion proteins. For example, it can be used as a therapeutic for interrupting the prion replication and/or propagation.

The hybrid polypeptides can be used in connection with immunoaffinity chromatography technology. More specifically, the hybrid polypeptides can be placed on the surface of a material within a chromatography column. Thereafter, a composition to be purified can be passed through the column. If the sample to be purified includes any proteins, such as $PrP^{Sc}$ in the exemplified embodiment, that bind to the hybrid polypeptides, such proteins will be removed from the sample and thereby purified or eliminated from a sample.

The hybrid polypeptides can be used to treat a mammal. They can be administered prophylactically or be administered to an infected animal. The exact amount of antibody to be administered will vary depending on a number of factors such as the age, sex, weight and condition of the subject animal. Those skilled in the art can determine the precise amount empirically, such as by administering hybrid polypeptides in small amounts and determining the effect and thereafter adjusting the dosage. It is suggested that the dosage can vary from 0.01 mg/kg to about 300 mg/kg, preferably about 0.1 mg/kg to about 200 mg/kg, typically about 0.2 mg/kg to about 20 mg/kg in one or more dose administrations daily, for one or several days. Generally administration of the antibody for 2 to 5 to 10 or more consecutive days in order to avoid "rebound" of the targeted protein.

3) Sources of Prions

Prions from many animals have been identified and sequenced; exemplary prions are set forth in SEQ ID NOS: 5-13. Any known prion protein is contemplated herein; sequences for such prions are available in public databases and in publications. For example, chicken, bovine, sheep, rat and mouse PrP genes are disclosed and published in Gabriel et al. (1992) *Proc. Natl. Acad. Sci. U.S.A.* 89:9097-9101; a sequence for the Syrian hamster is published in Basler et al. (1986) *Cell* 46:417-4281; the PrP gene of sheep is published in Goldmann et al. (1990) *Proc. Natl. Acad. Sci. U.S.A.* 0.87: 2476-2480; the bovine PrP gene sequence is published in Goldmann et al. (1991) *J. Gen. Virol.* 72:201-204; a chicken PrP gene is published in Harris et al. (1991) *Proc. Natl. Acad. Sci. USA* 88:7664-7668; a PrP gene sequence for mouse is published in Locht et al. (1986) *Proc. Natl. Acad. Sci. U.S.A.* 83:6372-6376; a PrP gene sequence for mink is published in Kretzschmar et al. (1992) *J. Gen. Virol.* 73:2757-2761, and a human PrP gene sequence is published in Kretzschmar et al. (1986) *DNA* 5:315-324. Mutations and variant forms of the genes and encoded proteins also are known (see, e.g., U.S. Pat. No. 5,908,969).

4) Mutations

In addition to animal prions, mutated forms thereof also are contemplated as a source of the polypeptide motif. Numerous mutant forms are known and have been characterized in humans. These include a proline (P) to leucine (L) mutation at codon 102 that was shown to be linked genetically to development of GSS with a LOD score exceeding three. This mutation can be due to the deamination of a methylated deoxycytosine (C) coupled to deoxyguanosine (G) through a phosphodiester bond (CpG) in the germline DNA encoding PrP resulting in the substitution of deoxythymine (T) for deoxycytosine. At codon 178 a mutation involving the substitution of aspartic acid (D) to asparagine (N) has been identified in many families with CJD. The D178N mutation has been linked with a number of Italian families with cases of insomnia, although the mutation appeared to be incompletely penetrant. The same mutation was also reported in several families affected by a disease phenotypically different from FFI and similar to CJD, except for the longer duration and the lack of sharp-wave electroencephalographic activity in most of the cases. This finding that the same mutation gives two different phenotypes prompted a series of studies to discover the molecular basis of this phenotypic heterogeneity. A detailed analysis of the PRNP genotype in 15 FFI and 15 CJD patients showed that in addition to the D178N mutation, all of the FFI subjects had a methionine at position 129 of the mutant allele while all CJD subjects had valine at this same position. These results have been confirmed in all of the FFI and CJD cases. Therefore this gives two distinct haplotypes, the 129M, D178N haplotype in FFI, and the 129V, D178N haplotype in CJD. As one of the FFI kindreds has an octapeptide repeat deletion in the mutant allele, it is very unlikely that all of the known FFI kindreds originated from a common founder. This finding strongly argues against the possibility that the phenotypic differences are caused by genetic influences other than PRNP codon 129. Although the methionine or valine at codon 129 on the mutant allele is obligatory in FFI and CJD178 patients respectively, the codon 129 on the normal allele can be either methionine or valine. Therefore, the FFI and CJD phenotypes are determined by the codon 129 of the mutant allele, which in association with the D178N mutation, results in the expression of two different types of PrPres. Also, as FFI is usually expressed in the phenotype earlier than CJD, the codon 129 also modulates the duration of the phenotype.

Studies on the PrPres fragments associated with the two proteins differ both in size and in the ratio of the three differently glycosylated PrPres isoforms. The size variation is the result of the differential N-terminal digestion by proteases and the difference indicates that PrPres has different conformations, or specific-ligand interactions. The ratio difference however indicates a different post-translational processing of PrP in the two diseases to ultimately give two different phenotypes. Also noted in these cases were the different incubation times in relation to the heterozygosity and homozygosity of the mutant allele. The homozygote duration of the disease was significantly shorter than that of the heterozygotes. The mean age of onset of CJD in homozygotes was 39+/−8 years and in the heterozygotes it was 49+/−4 years.

A valine (V) to isoleucine (I) substitution at codon 210 produces CJD with classic symptoms and signs, and like the D178N mutation appears to show incomplete penetrance. GSS has been associated with mutations in codons 105 and 114. Other point mutations have been shown at codons 145, 198, 217 and possibly 232 that segregate with inherited prion diseases. Interestingly, synthetic peptides adjacent to and including residues 109 to 122 respectively have readily polymerized into the rod-shaped structures, which have the tinctorial properties of amyloid.

Other than base substitutions, octapeptide inserts also can cause mutations. An insert of 144 bp at codon 53 containing 6 octarepeats was initially described in patients with CJD from four families all residing in southern England. As the human PrP gene only contains 5 octarepeats a single genetic recombination event could not have created this extra insert. Although as the four families were distantly related, a single person born more than two centuries ago may be the founder (LOD score greater than 11). Studies from several laboratories have demonstrated that two, four, five, six, seven, eight or nine octarepeats in addition to the normal five are shown in individuals with inherited CJD. Deletion of one octarepeat also has been identified but without any neurological disease.

Mutation of three K residues (residues 101, 104 and 106 using Syrina Hamster nomenclature, corresponding to 100, 103 and 105 in SEQ ID NO:9) present in 89-112 graft abolishes the PrP$^{Sc}$-reactivity of the hybrid polypeptides provided herein. Hence, these residues are among those that are key residues in the PrPC-PrPSc interaction.

b. Other Exemplary Proteins Involved in Diseases of Protein Aggregation or Conformation Methods for producing hybrid polypeptides that specifically interact with disease-related isoforms of target polypeptides from any disease of protein aggregation, particularly amyloid diseases, are provided herein. The target polypeptides are the disease-related or disease causing isoforms of the polypeptide that converts from a benign form to a malignant or disease-producing or aggregating isoform.

Target polypeptides include, but are not limited to, APP, Aβ, α1-antichymotrypsin, tau, non-Aβ component, presenilin 1, presenilin 2, apoE, superoxide dismutase (SOD) and neurofilament, Pick body, α-synuclein, tau in fibrils, amylin, IgGL-chain, transthyretin, procalcitonin, β$_2$-microglobulin, atrial natriuretic factor, serum amyloid A, ApoAl, gelsolin, Huntington protein and other such target proteins. Portions, motifs, of a benign (or disease-producing) form of the target polypeptide are included in the hybrid polypeptide.

c. Preparation of Hybrid Polypeptides

To prepare hybrid molecules specific for the disease, a portion of a conformation of the polypeptide that interacts with the disease-associated conformation is identified, such as by systematically testing fragments of the polypeptide for the ability to participate in a conformational change, such as by testing the ability of the fragment to interact with abnormal (i.e., disease-producing) conformers. Fragments of polypeptides with the desired ability can be employed as a specific reagent or introduced into a scaffold, such as an Fab or enzyme or other molecule such that it retains ability to specifically interact with the disease conformer.

A portion or region responsible for interaction with other isoforms of each of the proteins is identified empirically by systematically testing each protein, starting with the entire molecule and systematically removing portions and/or scanning along the length by selecting polypeptides. The identified regions are then inserted into a selected scaffold and the resulting molecule tested for the ability to bind to the target protein of interest. The resulting hybrid polypeptides serve as diagnostic reagents, reagents for use in drug screening assays and as potential therapeutics.

2. Scaffolds

Any molecule, such as a polypeptide, into which the selected polypeptide motif is inserted (or linked) such that the resulting hybrid polypeptide has the desired binding specificity, is contemplated for use as part of the hybrid molecules herein. The polypeptides can be inserted into any sequence of amino acids that at least contains a sufficient number (10, 20, 30, 50, 100 or more amino acids) to properly present the motif for binding to the targeted polypeptide. The purpose of the scaffold is to present the motif to the targeted polypeptide in a form that binds thereto. The scaffold can be designed or chosen to have additional properties, such as the ability to serve as a detectable marker or label or to have additional binding specificity to permit or aid in its use in assays to detect particular isoforms of a target protein or for screening for therapeutics or other assays and methods.

The scaffolds include reporter molecules, such as fluorescent proteins and enzymes or fragments thereof, and binding molecules, such as antibodies or fragments thereof. The scaffold serves the function of restraining or constraining or presenting a selected polypeptide motif, such as a PrP polypeptide portion, to retain or confer the specific binding properties. Selected scaffolds include all or portions of antibodies, enzymes, such as luciferases, alkaline phosphatases, β-galactosidase and other signal-generating enzymes, chemiluminescence generators, such as horseradish peroxidase;

fluorescent proteins, such as red, green and blue fluorescent proteins, which are well known; and chromogenic proteins.

The polypeptide motif is inserted into the scaffold in a region that does not disturb any desired activity. The scaffolds can include other functional domains, such as an additional binding site, such as one specific for a second moiety for detection.

a. Antibodies

Antibodies are exemplary of scaffolds or recipient polypeptides contemplated herein. Antibodies and fragments thereof can serve as scaffolds to produce hybrid polypeptides that contain a polypeptide motif of interest. The polypeptide motif can be inserted into any suitable region, such as the CDR3 loop (see, e.g., U.S. Pat. No. 5,583,202 and U.S. Pat. No. 5,568,762), which permits retention of the conformation of the polypeptide motif and presents it on the surface of the resulting hybrid polypeptide. The polypeptide motif is inserted into a heavy or light chain variable domain of an immunoglobulin molecule to produce hybrid immunoglobulins with specificity for a target polypeptide.

The basic immunoglobulin or antibody structural unit is well understood. The molecule contains heavy and light chains held together covalently through disulfide bonds. The heavy chains also are covalently linked in a base portion via disulfide bonds and this portion, referred to as the constant region, permits mutual recognition with cell surface molecules. There are five known major classes of constant regions which determine the class of the immunoglobulin molecule and are referred to as IgG, IgM, IgA, IgD and IgE. The N-terminal regions of the heavy chains branch outwardly, which is schematically represented as a Y-shaped structure. The light chains covalently bind to the Y branches of the two heavy chains. In the regions of the Y branches of the heavy chains lies a domain of approximately 100 amino acids in length which is variable, and therefore, specific for particular antigenic epitopes incidental to that particular immunoglobulin molecule. It is that region, for example, that can be replaced completely or in part with a polypeptide motif for binding to a target polypeptide such as the infectious or disease-involved isoform of a polypeptide involved in diseases of protein aggregation, such as amyloid diseases. In some embodiments, the polypeptide motif is introduced into an N-terminus or N-termini of the variable region (see, e.g., U.S. Pat. No. 5,583,202 for methods for preparing molecules with such alterations). The region, called the CDR3, is responsible for binding contact between a heavy chain and antigen. As such it is a good region to replace when producing the hybrid polypeptide reagents provided herein for detection of target polypeptides for use in the methods herein. The resulting molecules are generally mono- or di-valent with respect to the target polypeptide. They can be engineered to include different specificities to aid, for example, in detection in assays provided herein.

b. Other Molecules

As noted, other molecules, such as enzymes and luminescent molecules, can be used as scaffolds. These include all or portions of enzymes sufficient for catalytic and/or binding activity or of luminescent molecules sufficient to provide luminescence. Molecules for use as scaffolds, include, but are not limited to, luciferases (including photoproteins), alkaline phosphatases, β-galactosidase and other signal-generating enzymes, chemiluminescence generators, such as horseradish peroxidase; fluorescent proteins, such as red, green and blue fluorescent proteins, which are well known; and chromogenic molecules, including chromogenic proteins.

3. Exemplary Hybrids

As noted, prion proteins and hybrid molecules containing motifs therefrom are exemplary of hybrid molecules provided herein. Any motif from prion protein that includes at least one sequence of amino acids sufficient to confer specific binding on a hybrid molecules is contemplated. The motif includes at least five amino acids up to the entire molecule, and also include variants thereof that retain binding properties.

As shown herein, prion proteins include at least two distinct motifs, one from the about 89-112 region (using Syrian hamster nomenclature) of a prion polypeptide and the other from the about 136-141 region. Hybrid polypeptides including one or both of these regions are exemplified. For example, residues 89-112, 136-158 and 121-158 (see, FIG. 1, SEQ ID NO:5; and the corresponding residues in other prion polypeptides, e.g., SEQ ID NOS:5-13) have been grafted into scaffolds. In particular Fab, F(ab')$_2$ and IgG hybrids (also referred to as grafted antibodies), are exemplified. Also provided are hybrid polypeptides that include at least residues 101-106 or residues about 136-150. Any suitable scaffold or sequences of amino acids or other molecules that present the grafted motif for interaction with a PrP$^{Sc}$ at high affinity (Ka typically greater than about $10^6$-$10^7$ mol/l, generally greater than $10^7$ mol/l). Included among the scaffolds are enzymes, reporter molecules, antibodies, immunoglobulins, and fragments thereof.

For example, relatively long recognition sequences have been grafted previously into the HCDR3 region of antibody molecules to generate desired binding properties (McLane et al (1995) *Proc. Natl. Acad. Sci. U.S.A.* 92:5214-5218). Mouse PrP sequences corresponding to amino acids 89-112, 119-136, 136-158, 121-144 and 121-158 were grafted into the HCDR3 of IgG Fab b12 (Burton et al. (1994) *Science* 266: 1024-1027; see U.S. Pat. No. 5,652,138; b12 is derived from an antibody produced by the cell line designated MT12 having A.T.C.C. Accession Number 69079), a human recombinant antibody specific for HIV-1 gp120, by use of overlap polymerase chain reaction (PCR). The deposited cells designated MT12 *E. coli* cells contain the expression vector pComb2-3 for the expression of the Fabs designated b12 (clone b12) (see, U.S. Pat. No. 5,639,581, which provides the complete sequences of the heavy and light chain of this clone; see also SEQ ID Nos. 1-4 herein).

Fab b12 was chosen as an exemplary scaffold (recipient molecule) for grafted PrP sequence because the parental antibody possesses a relatively long HCDR3 (18 amino acids) that projects vertically from the surface of the antigen binding site (Ollmann Saphire et al. (2001) *Science* 293:1155). To maximally distance PrP sequence from the antibody surface, each graft was placed between the first N-terminal residue and four C-terminal residues of the parental HCDR3 (FIG. 1). In addition, two glycine residues were incorporated at each flank of the PrP sequence. The resulting PrP-Fabs (119-136, 121-144 and 121-158) were expressed in *E. coli* and purified to homogeneity (Williamson et al. (1993) *Proc. Natl. Acad. Sci. U.S.A.* 90:4141-4145).

In the exemplified embodiments, herein, a portion of the CDR3 loop of an antibody designated b12 (produced by a cell line designated MT12 having A.T.C.C. Accession Number 69079) is replaced with the grafted polypeptide motif. The resulting hybrid polypeptide, a hybrid immunoglobulin, retains the three-dimensional structure of the inserted motif, which is a PrP polypeptide motif in the exemplified embodiment. The hybrid immunoglobulin does not have the antigen-binding specificity of the parental immunoglobulin.

The Examples below describe preparation of a mouse hybrid polypeptides (see, FIG. 1). To prepare an exemplary hybrid polypeptide for bovine PrP, the CDR3 region of b12 antibody (see U.S. Pat. No. 5,652,138 for the complete amino acid sequence and description thereof; see, also SEQ ID NOS:1-4) set forth as amino acids 119-131 (Gly Pro Tyr Ser Trp Asp Asp Ser Pro Gln Asp Asn Tyr of SEQ ID NO:4), was removed and a portion of a target PrP that specifically binds to PrP$^{Sc}$, such as amino acid residues 121-158, 89-112 or 136-158 using Syrian Hamster nomenclature (see e.g., amino acids 132-169 of SEQ ID NO:13 for the corresponding bovine sequences; see, also FIG. 1), including Gly Gly at either end was inserted in to the IgG and/or Fab. As noted herein all nomenclature here correspond to the Syrian hamster PrP sequence that is commonly used for reference. The sequences were inserted in place of Gly Pro Tyr Ser Trp Asp Asp Ser Pro Gln Asp Asn Tyr (see SEQ ID NO:4 and FIG. 1).

Also prepared were a series of 15-35 mer PrP inserts that scan along the length of a PrP primary sequence, moving sequentially 10 amino acids from the N terminus to C terminus to further identify portions of PrP required for interaction with PrP$^{Sc}$-like conformations of the protein.

Evaluating the relative importance of individual PrP$^c$ residues in the PrP$^c$-PrP$^{Sc}$ interaction involved the production of additional Fabs containing truncated and mutated PrP sequence. In situ randomization of scaffold-grafted PrP sequences, followed by selection against infectious prion particles, can be used to evolve Fab molecules to produce molecules that possess ultra-high affinity for PrP$^{Sc}$. The resulting data are used experimentally to directly determine, through the use of novel PrP transgenes, how the kinetic properties of PrP$^c$-PrP$^{Sc}$ interactions modulate prion pathogenesis in vivo. Finally, screening for small molecules competing with hybrid polypeptides, such as hybrid IgGs or Fabs 121-158, 136-158 or 89-112, for binding to PrP$^{Sc}$ will yield candidate drugs capable of inhibiting prion replication, and/or for neutralizing a prion inoculum or fluid or tissue (including meat) containing prions. Such candidate drugs are potential therapeutics and/or prophylactics.

To study the reactivity of the PrP-Fab molecules against PrP$^c$, PrP$^{Sc}$ and PrP27-30, immunoprecipitation experiments using brain homogenate prepared from normal mice and from mice infected with the 79A strain of scrapie prions were performed. Precipitated PrP was detected by western blot. As positive controls, the 6H4 antibody (Korth et al. (1997) Nature 390:74-77) and D13 antibody to precipitate PrP$^c$ from normal mouse brain homogenates and plasminogen (Fischer et al. (2000) Nature 408:479-483)) to precipitate PrP$^{Sc}$ from prion-infected brain samples were used. Reaction of PrP Fabs with PrP$^c$ in normal mouse brain was either absent or extremely weak.

Each of these Fabs immunoprecipitated three PrP bands from pK-digested prion-infected brain homogenate. These bands correspond in size to the di-, mono-, and unglycosylated forms of PrP27-30, the proteinase resistant core of PrP$^{Sc}$ in which the N-terminal portion of the protein between residues 23-90 has been enzymatically degraded.

Fab 121-158 (FIG. 1b), which precipitated PrP27-30 with good efficiency, was next evaluated for reactivity with full-length PrP$^{Sc}$. Also evaluated were IgGs and Fabs 89-112 and 136-158. Using the Fab 121-158, for example, three bands of molecular weight 33-35 kDa, corresponding to full-length PrP$^s$, were precipitated from undigested homogenate of prion-infected brain tissue. Under identical experimental conditions, the parental b12 Fab did not react with either PrP$^c$, PrP$^{Sc}$ or PrP27-30.

Similar results were obtained with IgGs and Fabs 89-112 and 136-158. Moreover, Fabs containing a PrP sequence no longer recognized gp120, the target antigen of the parental b12 antibody, did not bind to any other protein when used to probe western blots of mouse brain homogenate, and were completely unreactive with PrP$^{Sc}$ following its denaturation to a PrP$^c$-like conformation by heating in the presence of SDS (data not shown). Thus, grafted PrP sequence composed of residues 121-158, 136-158 or 89-112 endows specific antibody recognition of PrP$^{Sc}$ and this disease-associated epitope is retained in PrP27-30. Grafted residues 136-158 retain these binding and recognition properties.

Next a series of immunoprecipitation experiments in which Fab or IgG 121-158 was used to immunoprecipitate PrP from lysates of scrapie prion-infected SMB cells (Chandler (1961) Lancet i:1378-1379; Clarke et al. (1970) Nature 225:100-101) were performed. Once again, Fab 121-158 did not bind to PrP$^c$ in untreated SMB lysate but was able to recognize PrP27-30 in these samples following pK digestion. Unlike the foregoing experiments in which Fab 121-158 efficiently precipitated PrP$^{Sc}$ from prion-infected brain homogenates, no full-length PrP$^{Sc}$ was immunoprecipitated from SMB cells using this antibody. Since the ratio of PrP$^c$:PrP$^{Sc}$ is approximately 4:1 in SMB cells, but can be considerably less than 1 in the brains of prion-infected mice with advanced disease (Safar et al. (1998) Nature Med. 4:1157-1165), it appears, that in the SMB lysates, PrP$^{Sc}$ is complexed with PrP$^c$ prior to addition of antibody. Under these circumstances, binding of Fab-IgG 121-158, which was originally designed to recognize the PrP$^{Sc}$ epitope bound by PrP$^c$, would be precluded. Conversely, in diseased brain tissues a proportion of PrP$^{Sc}$ molecules would remain uncomplexed because of the stoichiometric excess of PrP$^{Sc}$ over PrP$^c$ found in these preparations. Similar experiments (see, EXAMPLES) were performed with the IgG or Fab 136-158 or 89-112 hybrid polypeptides. In these experiments, IgG, Fab 121-158, IgG or Fab 136-158 or 89-112 possess the high affinity for disease-associated PrP conformers.

Figure 1B:
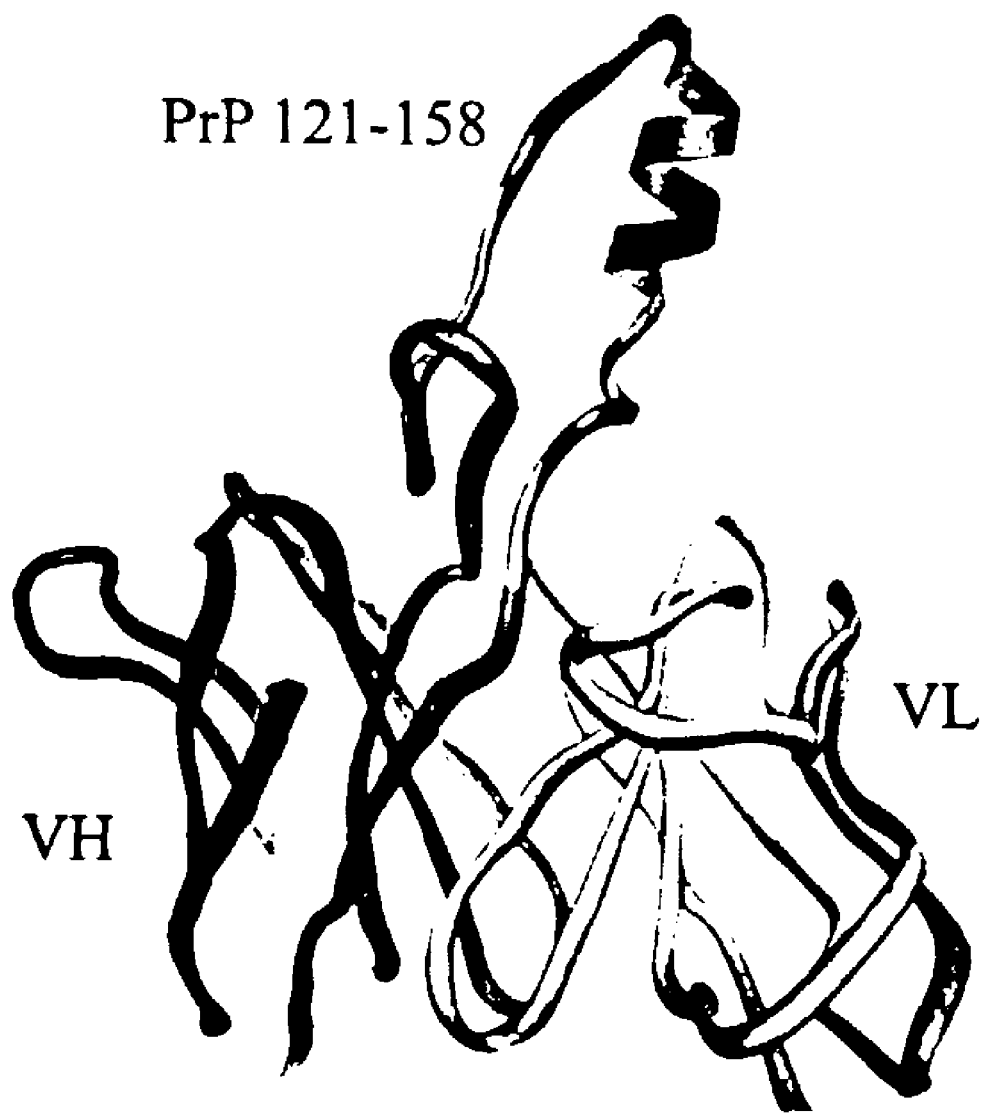

The IgG or Fab 121-158 or 136-158 polypeptide contain sequences composed of the first α-helix of PrP$^c$ (residues 145-155) (FIG. 1b). Fab19-136 and to a lesser extent Fab121-144, also bound to disease-associated forms of PrP, indicating that α-helix is not needed for specific recognition of PrP$^{Sc}$ or PrP27-30. Additional results indicate that 89-112 binds to disease-associated forms of PrP. Other results indicate that the about 100-106 residue portion of 89-112 region is important. Similarly, experiments indicate that the 136-141 are important for binding. Regions 89-112 and 136-158 (and the portions thereof) bind to distinct epitopes.

The above data are consistent with studies in which transgenic mice lacking PrP sequence between residues 140 and 175 are susceptible to infection with native mouse prions, albeit with significantly prolonged incubation times (Supattapone et al. (1999) Cell 96:869-878). In vivo, the intrinsic affinity of PrP$^{Sc}$ template for endogenous PrP$^c$ 'substrate' can be a parameter governing the efficiency of prion replication and by implication, the pathological course of prion disease.

Evaluating the relative importance of individual PrP$^c$ residues in the PrP$^c$-PrP$^{Sc}$ interaction requires the production of additional Fabs or Igs containing truncated and mutated PrP sequence. Moreover, in situ randomization of antibody-grafted PrP sequences, followed by selection against infectious prion particles, can be used to produce hybrid polypeptides that possess even higher affinity ($K_a > 10^9$ mol/l for PrP$^{Sc}$. In addition, data from studies of the importance of the particular residues can be used experimentally to directly determine, through the use of PrP transgenes, how the kinetic properties of PrP$^c$-PrP$^{Sc}$ interactions modulate prion pathogenesis in vivo. Also, screening for small molecules competing with IgG or Fab 121-158, 89-112 or 136-158 for binding to PrP$^{Sc}$ yields candidate drugs capable of potently inhibiting prion replication and/or neutralizing prion inocula.

Similar results are obtained with corresponding Igs, such as IgGs (discussed below and in the EXAMPLES). As discussed below, hybrid PrP IgGs also were prepared. Included among these are IgG 121-158, IgG 89-112 and IgG 136-158 and fragments thereof. IgG 121-158, IgG 89-112 and IgG 136-158 and certain fragments thereof, possess high affinity for PrP conformers. These results similarly indicate that the α-helix is not imperative for specific recognition of PrP$^{Sc}$ or PrP27-30.

Additional hybrid polypeptides have been prepared using the b12 scaffold. Amino acids 86-111 (based on Syrian hamster numbering; see SEQ ID NO:9) N-Terminal . . . GGWGQGGGTHNQWNKPSKPKTNLKHV . . . C-Terminal, and positions 86-117 N-Terminal . . . GGWGQGGGTH-NQWNKPSKPKTNLKHVAGAAAA . . . C-Terminal (see SEQ ID NO:9) of the mouse prion have been inserted and resulted in a hybrid molecule that specifically binds to the infectious form of the prion. Others include amino acids 89-112. As shown in the examples, hybrid polypeptides (also referred to herein as "antibodies" because they are inserted into an antibody scaffold) recognizing residues 133-157, particularly 136-158, and 96-104, particularly 89-112 are particularly potent.

Hybrid IgGs

Mouse PrP sequences corresponding to amino acids 89-112 and 136-158 were grafted into the HCDR3 of IgG1b12 (Burton et al. (1994) Science 266:1024-1207; see SEQ ID NOS:1-4), a human recombinant antibody specific for HIV-1 gp120, by use of overlap polymerase chain reaction (PCR). Antibody b12 was chosen as the recipient molecule for transplanted PrP sequence because the parental antibody possesses a relatively long HCDR3 (18 amino acids) that projects vertically from the surface of the antigen binding site (Ollmann et al. (2001) Science 293:1155-1159). To maximally distance PrP sequence from the antibody surface, each graft was placed between the first N-terminal residue and four C-terminal residues of the parental HCDR3 (see, FIG. 1). In addition, two glycine residues were incorporated at each flank of the PrP sequence. The resulting PrP-IgGs (89-112 and 136-158) were expressed in CHO cells and purified to homogeneity (Maruyama et al. (1999) J. Virol. 73:6024-6030).

To study the reactivity of the PrP-IgG molecules against PrP$^C$ and PrP$^{Sc}$ and PrP 27-30, experiments (described in EXAMPLE 4) were performed using brain homogenates prepared from normal mice and from mice infected with the RML or 79A strains of scrapie prions. Precipitated PrP was detected by western blot. As positive controls, Fab D13 and IgG 6H4 (Korth et al. (1997) Nature 390:74-77) were used to precipitate PrP$^C$ from normal mouse brain homogenates and plasminogen was used to precipitate PrP$^{Sc}$ from prion-infected brain samples. Reaction of PrP-IgG 89-112 or 136-158 with PrP$^C$ in normal mouse brain was not detected when the antibodies were used at a final concentration of 10 μg/ml. At the same or lower concentrations, each of these IgGs immunoprecipitated three PrP bands from undigested and pK-digested prion-infected brain homogenates. These bands correspond in size to the di-, mono-, and unglycosylated forms of PrP$^{Sc}$ and PrP 27-30, the proteinase resistant core of PrP$^{Sc}$ in which the N-terminal portion of the protein between residues 23-90 has been enzymatically degraded.

Under identical experimental conditions, the parental b12 IgG did not react with either PrP$^C$, PrP$^{Sc}$ or PrP 27-30. Moreover, IgGs containing PrP sequence no longer recognized gp120, the target antigen of the parental b12 antibody, did not bind to any other protein when used to probe western blots of mouse brain homogenate, and were completely unreactive with PrP$^{Sc}$ following its denaturation to a PrP$^C$-like conformation by heating in the presence of SDS (data not shown). Thus, the grafted PrP sequence composed of residues 89-112 or 136-158 endows specific antibody recognition of PrP$^{Sc}$ and that these disease-associated epitopes are retained in PrP 27-30.

To further demonstrate that the PrP grafts imparted specificity for disease-associated PrP conformations, a molecule was constructed in which the amino acids comprising the 136-158 graft were scrambled. The resulting antibody, termed PrP 136-158 random, showed only trace reactivity with PrP$^{Sc}$ and PrP 27-30 when used in an immunoprecipitation assay at a final concentration of 10 μg/ml, and no reactivity when employed at a concentration of 3 μg/ml. Specificity for PrP$^{Sc}$ and PrP 27-30 was lost when the PrP 136-158 graft was N-terminally truncated to residues 141-158k, indicating that PrP sequence between residues 136 and 140 (inclusive) is of importance in PrP$^C$-PrP$^{Sc}$ interactions. In fact, a single Syrian hamster-specific substitution at position 138 of mouse PrP has previously been shown to significantly inhibit production of proteinase K resistant PrP (Priola et al. (1995) J. Virol. 69:7754-7758). Further, a natural dimorphism at the equivalent position of goat PrP is linked with increased resistance of the host to infection with sheep and bovine prions (Goldmann et al. (1996) J. Gen. Virol. 77:2885-2891)

Specific interaction between plasminogen and PrP$^{Sc}$ is dependent upon the presence of detergent that disrupts membrane rafts (Shaked et al. (2002) J. Neurochem. 82:1-5). To determine whether the binding interactions between IgGs 89-112 and 136-158 and PrP$^{Sc}$ and PrP 27-30 were affected by detergent conditions, parallel immunoprecipitation experiments were performed in which prion-infected mouse brain homogenate was prepared using either NP-40 and sodium deoxycholate (DOC) (reagents disrupting membrane rafts) or Triton X-100 (a detergent preserving raft architecture). The results indicate that reactivity of the PrP-grafted antibodies with PrP$^{Sc}$ is unaffected by detergent conditions, and that binding to PrP 27-30 is significantly enhanced in the presence of Triton X-100. Under equivalent conditions, IgG b12 bound to neither PrP$^{Sc}$ nor PrP 27-30. Similarly, IgGs 89-112 and 136-158 did not recognize PrP$^C$ in normal mouse brain extracted in the presence of Triton X-100.

Figure 3:
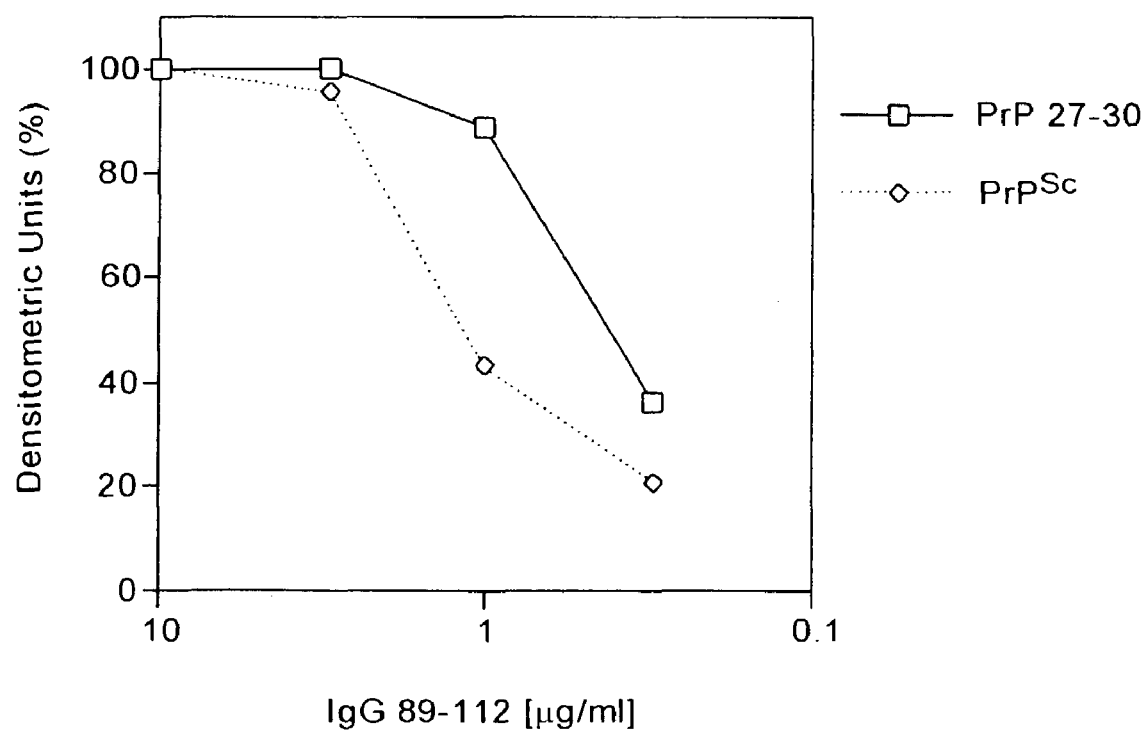

Of these PrP-grafted antibody, IgG 89-112 possesses the greatest affinity for disease-associated PrP conformers. To estimate the affinity of this molecule for PrP$^{Sc}$ and PrP 27-30, a series of immunoprecipitation experiments were performed using decreasing concentrations of antibody. The relative amounts of PrP precipitated at each antibody concentration were visualized by immunoblot and quantitated by densitometric analysis. Plotting densitometry values against antibody concentration yielded a titration curve from which antibody concentrations producing 50% maximum binding signals against PrP$^{Sc}$ and PrP 27-30 could be determined and used to estimate binding constants for these antigens. The results indicate that IgG 89-112 possesses apparent affinities of approximately 2 nM for PrP 27-30 and 7 nM for PrP$^{Sc}$ (see FIG. 3).

These data illustrate that the motif-grafting approach has identified at least two independent regions of PrP sequence that possess remarkably high intrinsic specificity and affinity for epitopes found exclusively on PrP$^{Sc}$ and PrP 27-30. Using similar experiments with additional hybrid polypeptides containing different PrP sequences, the relative importance of individual PrP$^C$ residues in the PrP$^C$-PrP$^{Sc}$ interaction can be assessed. In situ randomization of antibody-grafted PrP sequences (or other evolution protocols) followed by selection against infectious prion particles, can be produce molecules possessing ultra-high affinity for PrP$^{Sc}$.

The hybrid polypeptides provided herein can be used to screen for small molecules that compete with IgGs (or Fabs) 89-112 and 136-158 for binding to PrP$^{Sc}$ to yield candidate drugs capable of potently inhibiting prion replication.

C. Nucleic Acid Molecules, Vectors, Plasmids, Cells and Methods for Preparation of the Hybrid Polypeptides Nucleic acid molecules encoding any of the hybrid polypeptides provided herein are provided. Such molecules can be introduced into plasmids and vectors for expression in suitable host cells.

Plasmids, Vectors and Cells

Plasmids and vectors containing the nucleic acid molecules also are provided. Cells containing the vectors, including cells that express the encoded proteins are provided. The cell can be a bacterial cell, a yeast cell, a fungal cell, a plant cell, an insect cell or an animal cell. Methods for producing a hybrid polypeptide, for example, growing the cell under conditions whereby the encoded polypeptide is expressed by the cell, and recovering the expressed protein, are provided herein. The cells are used for expression of the protein, which can be secreted or expressed in the cytoplasm. The hybrid polypeptides also can be chemically synthesized using standard methods of protein synthesis.

Any methods known to those of skill in the art for the insertion of nucleic acid fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid encoding the hybrid polypeptide can be regulated by a second nucleic acid sequence so that the genes or fragments thereof are expressed in a host transformed with the recombinant DNA molecule(s). For example, expression of the proteins can be controlled by any promoter/enhancer known in the art. Promoters which can be used include but are not limited to the SV40 early promoter (Bernoist and Chambon, *Nature* 290:304-310 (1981)), the promoter contained in the 3' long terminal repeat of Rous sarcoma virus (Yamamoto et al., *Cell* 22:787-797 (1980)), the herpes thymidine kinase promoter (Wagner et al., *Proc. Natl. Acad. Sci. USA* 78:1441-1445 (1981)), the regulatory sequences of the metallothionein gene (Brinster et al., *Nature* 296:39-42 (1982)); prokaryotic expression vectors such as the β-lactamase promoter (Villa-Kamaroff et al., *Proc. Natl. Acad. Sci. USA* 75:3727-3731 1978)) or the tac promoter (DeBoer et al., *Proc. Natl. Acad. Sci. USA* 80:21-25 (1983)); see also "Useful Proteins from Recombinant Bacteria": in Scientific American 242:79-94 (1980)); plant expression vectors containing the nopaline synthetase promoter (Herrar-Estrella et al., *Nature* 303:209-213 (1984)) or the cauliflower mosaic virus 35S RNA promoter (Garder et al., *Nucleic Acids Res.* 9:2871 (1981)), and the promoter of the photosynthetic enzyme ribulose bisphosphate carboxylase (Herrera-Estrella et al., *Nature* 310:115-120 (1984)); promoter elements from yeast and other fungi such as the Gal4 promoter, the alcohol dehydrogenase promoter, the phosphoglycerol kinase promoter, the alkaline phosphatase promoter, and the following animal transcriptional control regions that exhibit tissue specificity and have been used in transgenic animals: elastase I gene control region which is active in pancreatic acinar cells (Swift et al., *Cell* 38:639-646 (1984); Ornitz et al., *Cold Spring Harbor Symp. Quant. Biol.* 50:399-409 (1986); MacDonald, *Hepatology* 7:425-515 (1987)); insulin gene control region which is active in pancreatic beta cells (Hanahan et al., *Nature* 315:115-122 (1985)), immunoglobulin gene control region which is active in lymphoid cells (Grosschedl et al., *Cell* 38:647-658 (1984); Adams et al., *Nature* 318:533-538 (1985); Alexander et al., *Mol. Cell Biol.* 7:1436-1444 (1987)), mouse mammary tumor virus control region which is active in testicular, breast, lymphoid and mast cells (Leder et al., *Cell* 45:485-495 (1986)), albumin gene control region which is active in liver (Pinckert et al., *Genes and Devel.* 1:268-276 (1987)), alpha-fetoprotein gene control region which is active in liver (Krumlauf et al., *Mol. Cell. Biol.* 5:1639-1648 (1985); Hammer et al., *Science* 235:53-58 1987)), alpha-1 antitrypsin gene control region which is active in liver (Kelsey et al., *Genes and Devel.* 1:161-171 (1987)), beta globin gene control region which is active in myeloid cells (Mogram et al., *Nature* 315:338-340 (1985); Kollias et al., *Cell* 46:89-94 (1986)), myelin basic protein gene control region which is active in oligodendrocyte cells of the brain (Readhead et al., *Cell* 48:703-712 (1987)), myosin light chain-2 gene control region which is active in skeletal muscle (Sani, *Nature* 314:283-286 (1985)), and gonadotrophic releasing hormone gene control region which is active in gonadotrophs of the hypothalamus (Mason et al., *Science* 234:1372-1378 (1986)).

In a specific embodiment, a vector is used that contains a promoter operably linked to nucleic acid encoding a hybrid polypeptide, or a domain, fragment, derivative or homolog, thereof, one or more origins of replication, and optionally, one or more selectable markers (e.g., an antibiotic resistance gene). Expression vectors containing the coding sequences, or portions thereof, the hybrid polypeptide, is made, for example, by subcloning the coding portions into the EcoRI restriction site of each of the three pGEX vectors (glutathione S-transferase expression vectors (Smith and Johnson, *Gene* 7:31-40 (1988)). This allows for the expression of products in the correct reading frame. Exemplary vectors and systems for expression of hybrid polypeptides include the well-known Pichia vectors (available, for example, from Invitrogen, San Diego, Calif.), particularly those designed for secretion of the encoded proteins. The protein also can be expressed cytoplasmically, such as in the inclusion bodies.

Plasmids for transformation of *E. coli* cells, include, for example, the pET expression vectors (see, U.S. Pat. No. 4,952,496; available from NOVAGEN, Madison, Wis.; see, also literature published by Novagen describing the system). Such plasmids include pET 11a, which contains the T7lac promoter, T7 terminator, the inducible *E. coli* lac operator, and the lac repressor gene; pET 12a-c, which contains the T7 promoter, T7 terminator, and the *E. coli* ompT secretion signal; and pET 15b and pET19b (NOVAGEN, Madison, Wis.), which contain a His-Tag™ leader sequence for use in purification with a His column and a thrombin cleavage site that permits cleavage following purification over the column; the T7-lac promoter region and the T7 terminator.

The vectors are introduced into host cells, such as Pichia cells and bacterial cells, such as E. col, and the proteins expressed therein. Exemplary Pichia strains, include, for example, GS115. Exemplary bacterial hosts contain chromosomal copies of DNA encoding T7 RNA polymerase operably linked to an inducible promoter, such as the lacUV promoter (see, U.S. Pat. No. 4,952,496). Such hosts include, but are not limited to, the lysogenic *E. coli* strain BL21 (DE3).

D. Peptide Mimetics

Peptide analogs are commonly used in the pharmaceutical industry as non-peptide drugs with properties analogous to those of the template peptide. These types of non-peptide compounds are termed "peptide mimetics" or "peptidomimetics" (Luthman et al., *A Textbook of Drug Design and Development*, 14:386-406, 2nd Ed., Harwood Academic Publishers (1996); Joachim Grante (1994) *Angew. Chem. Int. Ed. Engl.*, 33:1699-1720; Fauchere (1986) *J. Adv. Drug Res.*, 15:29; Veber and Freidinger (1985) *TINS*, p. 392; and Evans et al. (1987) *J. Med. Chem.* 30:1229). Peptide mimetics that are structurally similar to therapeutically useful peptides can be used to produce an equivalent or enhanced therapeutic or prophylactic effect. Preparation of peptidomimetics and structures thereof are known to those of skill in this art. Peptide mimetics of the hybrid polypeptides are provided herein.

Systematic substitution of one or more amino acids of a consensus sequence with a D-amino acid of the same type (e.g., D-lysine in place of L-lysine) can be used to generate more stable peptides. In addition, constrained peptides containing a consensus sequence or a substantially identical consensus sequence variation can be generated by methods known in the art (Rizo et al. (1992) *An. Rev. Biochem.*, 61:387, incorporated herein by reference); for example, by adding internal cysteine residues capable of forming intramolecular disulfide bridges which cyclize the peptide.

Those skilled in the art appreciate that modifications can be made to the peptides and mimetics without deleteriously effecting the biological or functional activity of the peptide. Further, the skilled artisan would know how to design non-peptide structures in three dimensional terms, that mimic the hybrid polypeptides (see, e.g., Eck and Sprang (1989) *J. Biol. Chem.*, 26: 17605-18795).

When used for diagnostic purposes, the peptides and peptide mimetics can be labeled with a detectable label and, accordingly, the peptides and peptide mimetics without such a label can serve as intermediates in the preparation of labeled peptides and peptide mimetics. Detectable labels can be molecules or compounds, which when covalently attached to the peptides and peptide mimetics, permit detection of the peptide and peptide mimetics in vivo, for example, in a patient to whom the peptide or peptide mimetic has been administered, or in vitro, e.g., in a sample or cells. Suitable detectable labels are well known in the art and include, by way of example, radioisotopes, fluorescent labels (e.g., fluorescein), and the like. The particular detectable label employed is not critical and is selected to be detectable at non-toxic levels. Selection of such labels is well within the skill of the art.

Covalent attachment of a detectable label to the peptide or peptide mimetic is accomplished by conventional methods well known in the art. For example, when the $^{125}$I radioisotope is employed as the detectable label, covalent attachment of $^{125}$I to the peptide or the peptide mimetic can be achieved by incorporating the amino acid tyrosine into the peptide or peptide mimetic and then iodinating the peptide (see, e.g., Weaner et al. (1994) *Synthesis and Applications of Isotopically Labelled Compounds*, pp. 137-140). If tyrosine is not present in the peptide or peptide mimetic, incorporation of tyrosine to the N or C terminus of the peptide or peptide mimetic can be achieved by well known chemistry. Likewise, $^{32}$P can be incorporated onto the peptide or peptide mimetic as a phosphate moiety through, for example, a hydroxyl group on the peptide or peptide mimetic using conventional chemistry.

Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivatization (e.g., labeling) of peptidomimetics should not substantially interfere with the desired biological or pharmacological activity of the peptidomimetic.

E. Diagnostics, Therapeutics, Assays and Other Uses of the Hybrid Polypeptides

The hybrid molecules provided herein have a variety of uses. They can be used in assays to detect the presence of one conformer in a sample, such as a body fluid or tissue sample or a food sample or soil sample or other such sample. They can be used as therapeutics for treating diseases; they can be used for screening for candidate drugs and/or in the design of drugs and therapeutics or diagnostic agents.

1. Diagnostics and Therapeutics

By virtue of the specific interaction of the hybrid polypeptides provided herein and a disease-causing (or disease-involved) or infectious form of a polypeptide involved in a disease of protein aggregation (or conformation), such polypeptides can be used to detect the presence of the disease-causing or infectious form of the target polypeptide in a sample, such as in food or body fluid or tissue sample. For example, the hybrid polypeptides that specifically interact with PrP$^{Sc}$ can be used to screen blood and other tissues.

The hybrid polypeptides provided herein can be employed for diagnostic and therapeutic purposes. As diagnostics they can be used to test and protect the blood supply and tissue and transplant recipients; to test animals used for food. The polypeptides also can be used in assays to identify candidate therapeutics.

In particular embodiments, reagents and assays for detecting infectious prions in tissue, organ and body fluid samples of any animal are provided. The reagents can be placed on a substrate or in solution and a sample assayed to determine if the sample contains a pathogenic form of a prion protein. The reagents are prepared to bind to PrP$^{Sc}$ forms of a prion polypeptide without any treatment, such as denaturation, of the prion protein. Species-specific reagents also can be prepared by the methods herein. Homogeneous and heterogenous phase assays are provided.

Methods for detecting an isoform of polypeptide associated with a disease of protein aggregation are provided. The methods include the steps of contacting a sample suspected of containing the isoform with a hybrid polypeptide that specifically binds to the isoform and detecting binding of the polypeptide. Detection can be effected by any method known to those of skill in the art, including radiolabel, color or fluorescence detection, mass spectrometry and other detection methods. For example, the hybrid polypeptide can be detectable labeled or can contain a fluorescent or chromogenic moiety or moieties or can be a fluorescent or chromogenic peptide or other reporter, such as an enzyme, including a luciferase (from Renilla, Aequora and from other deep sea creatures, from bacteria or insects) or other enzymatic label. Alternatively, such label, such as a fluorescent protein or enzyme can serve as a scaffold into which the motif is inserted, such that the enzymatic activity or fluorescence is retained. Also, the hybrid polypeptide can include additional binding sites to capture antibodies or nucleic acids or other detectable moieties.

In one embodiment, a method for identifying the infectious or disease-causing form of a target polypeptide in cells is provided. The hybrid polypeptide specific for the target is detectably labeled, such as fluorescently labeled or inserted into a fluorescent protein or a luciferase, and contacted with a sample, such as a blood sample. Labeled cells are identified, such as by flow cytometry and scanning cytometry. Methods and instruments for identifying very low concentrations of labeled cells among unlabeled cells are available (see, e.g., Bajaj et al. (2000) *Cytometry* 39:285-294, published U.S. application Ser. No. 09/123,564, published as US2002018674, and instrumentation commercialized by Q3DM, LLC, San Diego). In an alternative embodiment, label the hybrid polypeptides that interact with distinct epitopes, such as hybrid polypeptides containing residues from 136-158 and 89-112, with different color dyes. The resulting labeled hybrid polypeptides, such as two polypeptides, are mixed with cells to be tested simultaneously or sequentially. Association of both colors with a single cell, provides a self-confirmatory assay. For example the 136-158 and 89-112 PrP motifs (or portions thereof sufficient to interact with an epitope, such as at least amino acids 100-106 or 136-141) are grafted into different florescent proteins, such as green fluorescent proteins with distinct emission spectra, which will achieve the same double labelling of single cells.

The assays can be performed in solution or in solid phase. The hybrid polypeptides can be provided on a solid support, such as a chip or microwell plate and contacted with a sample. In other embodiments, a plurality of different hybrid polypeptides, each addressable, can be employed to permit identification and/or detection of a plurality of different polypeptides indicative of the presence of a polypeptide associated with a disease of protein aggregation.

The assays can be used for diagnosis of these diseases by detection of the presence of a polypeptide associated with a disease of protein aggregation in a biological sample, or to monitor the supply of body fluids such as blood and organs and tissues for transplantation, or to monitor the food supply to ensure that they are not contaminated with these polypeptides.

In particular embodiments, methods of detecting a $PrP^{Sc}$ or PrP 27-30 form of a prion polypeptide are provided. A sample suspected of containing an infectious isoform of a prion polypeptide is contacted with hybrid polypeptide containing a $PrP^c$ form of a prion polypeptide or a portion thereof or with a prion polypeptide or portion thereof; and complexes of the hybrid polypeptide and any $PrP^{Sc}$ in the sample is detected. The hybrid polypeptide can contain or can be all or at least about 20, 25, 30, 35, 45, 50, 55, 60, 65, 70, 75, 80, 85, 90, 95, 100 or more contiguous amino acid residues up to the full length of a $PrP^c$ form of a prion polypeptide. The prion can be an animal prion such as a prion found in humans and other primates, hamsters, llamas, marsupials, mice, rats, deer, sheep, goats, elk, kudu, horses, dogs, cats, camels, pigs and other domesticated, common or zoo animals.

The samples can be biological samples or any other sample suspected of containing a protein associated with a disease of protein aggregation. Samples include body fluids, tissues and organs. Body fluids include, but are not limited to, blood, urine, sweat, saliva, plasma, serum, cerebrospinal fluid, sperm samples and synovial fluid, foods and other products derived from animal tissues, body fluids and organs, including drugs and bioactive molecules, such as hormones, cytokines and growth factors, antibodies and blood fractions.

Diseases diagnosed or detected include amyloid diseases, such as, Creutzfeldt-Jakob disease, including variant, sporadic and iatrogenic, scrapie and bovine spongiform encephalopathy, Alzheimer's Disease, Type II Diabetes, Huntington's Disease, immunoglobulin amyloidosis, reactive amyloidosis associated with chronic inflammatory disease, e.g., inflammatory arthritis, granulomatous bowel disease, tuberculosis and leprosy, hereditary systemic amyloidosis associated with autosomal dominant inheritance of variant transthyretin gene, ALS, Pick's Disease, Parkinson's disease, Frontotemporal dementia, Diabetes Type II, Multiple myeloma, Plasma cell dyscrasias, Familial amyloidotic polynueuropathy, Medullary carcinoma of thyroid; chronic renal failure, congestive heart failure, senile cardiac and systemic amyloidosis, chronic inflammation, atherosclerosis and familial amyloidosis.

In an exemplary embodiment, an assay is performed by adding a body fluid, such as blood, or tissue sample, such as a brain biopsy or muscle sample with cells optionally removed to a solution containing one or a plurality of hybrid polypeptides. Optionally separate complexes from uncomplexed material, such as by capturing the hybrid polypeptides, which can include a second binding site specific for a selected capture agents, such as an antibody. Complexes can then be identified.

For a solid phase assay surface can be coated with $PrP^c$ or a hybrid polypeptide and then contacted with sample, so that any $PrP^{Sc}$ in the sample binds to the $PrP^c$. Detection can be effected using a different $PrP^{Sc}$-specific reagent that binds to different site complexes; or the captured $PrP^{Sc}$ can be denatured, after which they refold into PrP and use standard reagents to detect it.

2. Drug Screening Assays

A test compound able to prevent or decrease the amount of $PrP^{Sc}$ bound to a hybrid polypeptide is a candidate for use in vivo preventing or treating a $PrP^{Sc}$-mediated disease, such as Creutzfeldt-Jacob Disease (CJD), including variant, sporadic and/or iatrogenic Gerst-mann-Straussler-Scheinker Disease (GSS), fatal familiar insomnia (FFI), kuru, scrapie, bovine spongiform encephalopathy (BSE), and any other disease involving formation of $PrP^{Sc}$. A test compound identified by such method as able to inhibit or decrease the in vitro interaction of a hybrid polypeptide with $PrP^{Sc}$ can be tested in an in vivo model of $PrP^{Sc}$ disease for ability to prevent development of or treat a $PrP^{Sc}$ disease.

Also provided are competitive screens in libraries, such as libraries of small molecules, that inhibit binding of a hybrid polypeptide to its target polypeptide are identified. For example, members of libraries of small molecules that modulate, particular decrease or competitively inhibit, binding of $PrP^{Sc}$-specific hybrid polypeptides to non-denatured $PrP^{Sc}$ or PrP 27-30 are identified. Such identified library members are candidate compounds for further screening.

Similarly, hybrid polypeptides specific for other target polypeptides involved in diseases of protein aggregation, such as other amyloid diseases, can be used to identify candidate therapeutics for such diseases. The libraries can be designed to be based on pharmacophores or other structures that are specific for a particular disease.

3. Immobilization and Supports or Substrates Therefor

In certain embodiments, where the assays are performed on solid supports, such as paramagnetic beads, polypeptides from a sample or, generally, the hybrid polypeptides can be attached by linkage such as ionic or covalent, non-covalent or other chemical interaction, to a surface of a support or matrix material. Immobilization can be effected directly or via a linker. Immobilization can be effected on any suitable support, including, but are not limited to, silicon chips, and other supports described herein and known to those of skill in the art. A plurality of polypeptides can be attached to a support, such as an array (i.e., a pattern of two or more) on the surface of a silicon chip or other chip for use in the assays, including in high throughput protocols and formats.

The matrix material or solid supports contemplated herein are generally any of the insoluble materials known to those of skill in the art to immobilize ligands and other molecules, and are those that are used in many chemical syntheses and separations. Such supports are used, for example, in affinity chromatography, in the immobilization of biologically active materials, and during chemical syntheses of biomolecules, including proteins, amino acids and other organic molecules and polymers. The preparation of and use of supports is well known to those of skill in this art; there are many such materials and preparations thereof known. For example, naturally-occurring support materials, such as agarose and cellulose, can be isolated from their respective sources, and processed according to known protocols, and synthetic materials can be prepared in accord with known protocols.

The supports are typically insoluble materials that are solid, porous, deformable, or hard, and have any required structure and geometry, including, but not limited to: beads, pellets, disks, capillaries, hollow fibers, needles, paramagnetic beads, solid fibers, random shapes, thin films and membranes. Thus, the item can be fabricated from the matrix material or combined with it, such as by coating all or part of the surface or impregnating particles.

Typically, when the matrix is particulate, the particles are at least about 10-2000 µm, but can be smaller or larger, depending upon the selected application. Selection of the matrices is governed, at least in part, by their physical and chemical properties, such as solubility, functional groups, mechanical stability, surface area swelling propensity, hydrophobic or hydrophilic properties and intended use.

If necessary, the support matrix material can be treated to contain an appropriate reactive moiety. In some cases, the support matrix material already containing the reactive moiety can be obtained commercially. The support matrix material containing the reactive moiety can thereby serve as the matrix support upon which molecules are linked. Materials containing reactive surface moieties such as amino silane linkages, hydroxyl linkages or carboxysilane linkages can be produced by well established surface chemistry techniques involving silanization reactions, or the like. Examples of these materials are those having surface silicon oxide moieties, covalently linked to gamma-aminopropyl-silane, and other organic moieties; N-[3-(triethyoxysilyl)propyl]phthelamic acid; and bis-(2-hydroxyethyl)aminopropyltriethoxysilane. Exemplary of readily available materials containing amino group reactive functionalities, include, but are not limited to, para-aminophenyltriethyoxysilane. Also derivatized polystyrenes and other such polymers are well known and readily available to those of skill in this art (e.g., the Tentagel® Resins are available with a multitude of functional groups, and are sold by Rapp Polymere, Tubingen, Germany; see, U.S. Pat. No. 4,908,405 and U.S. Pat. No. 5,292,814; see, also Butz et al., *Peptide Res.*, 7:20-23 (1994); and Kleine et al., *Immunobiol.*, 190:53-66 (1994)).

These matrix materials include any material that can act as a support matrix for attachment of the molecules of interest. Such materials are known to those of skill in this art, and include those that are used as a support matrix. These materials include, but are not limited to, inorganics, natural polymers, and synthetic polymers, including, but are not limited to: cellulose, cellulose derivatives, acrylic resins, glass, silica gels, polystyrene, gelatin, polyvinyl pyrrolidone, co-polymers of vinyl and acrylamide, polystyrene cross-linked with divinylbenzene and others (see, Merrifield, *Biochemistry*, 3:1385-1390 (1964)), polyacrylamides, latex gels, polystyrene, dextran, polyacrylamides, rubber, silicon, plastics, nitrocellulose, celluloses, natural sponges. Of particular interest herein, are highly porous glasses (see, e.g., U.S. Pat. No. 4,244,721) and others prepared by mixing a borosilicate, alcohol and water.

Synthetic supports include, but are not limited to: acrylamides, dextran-derivatives and dextran co-polymers, agarose-polyacrylamide blends, other polymers and co-polymers with various functional groups, methacrylate derivatives and co-polymers, polystyrene and polystyrene copolymers (see, e.g., Merrifield, *Biochemistry*, 3:1385-1390 (1964); Berg et al., in *Innovation Perspect. Solid Phase Synth. Collect. Pap.*, Int. Symp., 1st, Epton, Roger (Ed), pp. 453-459 (1990); Berg et al., *Pept., Proc. Eur. Pept. Symp.*, 20th, Jung, G. et al. (Eds), pp. 196-198 (1989); Berg et al., *J. Am. Chem. Soc.*, 111:8024-8026 (1989); Kent et al., *Isr. J. Chem.*, 17:243-247 (1979); Kent et al., *J. Org. Chem.*, 43:2845-2852 (1978); Mitchell et al., *Tetrahedron Lett.*, 42:3795-3798 (1976); U.S. Pat. No. 4,507,230; U.S. Pat. No. 4,006,117; and U.S. Pat. No. 5,389,449). Such materials include those made from polymers and co-polymers such as polyvinylalcohols, acrylates and acrylic acids such as polyethylene-co-acrylic acid, polyethylene-co-methacrylic acid, polyethylene-co-ethylacrylate, polyethylene-co-methyl acrylate, polypropylene-co-acrylic acid, polypropylene-co-methyl-acrylic acid, polypropylene-co-ethyl-acrylate, polypropylene-co-methyl acrylate, polyethylene-co-vinyl acetate, polypropylene-co-vinyl acetate, and those containing acid anhydride groups such as polyethylene-co-maleic anhydride and polypropylene-co-maleic anhydride. Liposomes also have been used as solid supports for affinity purifications (Powell et al. *Biotechnol. Bioeng.*, 33:173 (1989)).

Numerous methods have been developed for the immobilization of proteins and other biomolecules onto solid or liquid supports (see, e.g., Mosbach, *Methods in Enzymology*, 44 (1976); Weetall, *Immobilized Enzymes, Antigens, Antibodies, and Peptides*, (1975); Kennedy et al., *Solid Phase Biochemistry, Analytical and Synthetic Aspects*, Scouten, ed., pp. 253-391 (1983); see, generally, Affinity Techniques. Enzyme Purification: *Part B. Methods in Enzymology*, Vol. 34, ed. W. B. Jakoby, M. Wilchek, Acad. Press, N.Y. (1974); and Immobilized Biochemicals and Affinity Chromatography, *Advances in Experimental Medicine and Biology*, vol. 42, ed. R. Dunlap, Plenum Press, N.Y. (1974)).

Among the most commonly used methods are absorption and adsorption or covalent binding to the support, either directly or via a linker, such as the numerous disulfide linkages, thioether bonds, hindered disulfide bonds, and covalent bonds between free reactive groups, such as amine and thiol groups, known to those of skill in art (see, e.g., the PIERCE CATALOG, ImmunoTechnology Catalog & Handbook, 1992-1993, which describes the preparation of and use of such reagents and provides a commercial source for such reagents; Wong, *Chemistry of Protein Conjugation and Cross Linking*, CRC Press (1993); see also DeWitt et al., *Proc. Natl. Acad. Sci. U.S.A.*, 90:6909 (1993); Zuckermann et al., *J. Am. Chem. Soc.*, 114:10646 (1992); Kurth et al., *J. Am. Chem. Soc.*, 116:2661 (1994); Ellman et al., *Proc. Natl. Acad. Sci. U.S.A.*, 91:4708 (1994); Sucholeiki, *Tetrahedron Lttrs.*, 35:7307 (1994); Su-Sun Wang, *J. Org. Chem.*, 41:3258 (1976); Padwa et al., *J. Org. Chem.*, 41:3550 (1971); and Vedejs et al., *J. Org. Chem.*, 49:575 (1984), which describe photosensitive linkers).

To effect immobilization, a composition containing the protein or other biomolecule is contacted with a support material such as alumina, carbon, an ion-exchange resin, cellulose, glass or a ceramic. Fluorocarbon polymers have been used as supports to which biomolecules have been attached by adsorption (see, U.S. Pat. No. 3,843,443; Published International PCT Application WO/86 03840).

4. Standardized Prion Preparation

Standardized prion preparations can be produced in order to test assays to thereby improve the reliability of the assay. Details regarding making standardized prion preparations are known (see, e.g., U.S. Pat. No. 5,639,581, U.S. Pat. No. 5,908,969 and U.S. Pat. No. 5,792,901). The preparation can be obtained from any animal, such as a host animal that has brain material containing prions of a test animal. For example, a transgenic mouse containing a human prion protein gene can produce human prions and the brain of such a mouse can be used to create a standardized human prion preparation. Further, in that the preparation is to be a "standard" it is generally obtained from a battery (e.g., 100; 1,000, or more animals) of substantially identical animals. For example, 100 mice all containing a very high copy number of human PrP genes (all polymorphisms and mutations) spontaneously develop disease and the brain tissue from each can be combined to make a standardized prion preparation.

Standardized prion preparations can be produced using any of modified host mammals. For example, standardized prion preparations can be produced using mice, rats, hamsters, or guinea pigs which are genetically modified so that they are susceptible to infection with prions that generally only infect genetically diverse species such as a human, cow, sheep or horse and which modified host mammals will develop clinical signs of CNS dysfunction within a period of time of 350 days or less after inoculation with prions. An exemplary host mammal is a mouse.

Once an appropriate type of host is chosen, such as a mouse, an appropriate type of genetic manipulation to produce a standardized prion formulation is selected. For example, the mice can be genetically modified by the insertion of a chimeric gene. Within this group the mice can be modified by including high copy numbers of the chimeric gene and/or by the inclusion of multiple promoters in order to increase the level of expression of the chimeric gene. Alternatively, hybrid mice that have the endogenous PrP gene ablated are crossed with mice which have a human PrP gene inserted into their genome. There are various subcategories of such hybrid mice. For example, the human PrP gene can be inserted in a high copy number and/or used with multiple promoters to enhance expression. As another alternative the mice can be produced by inserting multiple different PrP genes into the genome so as to create mice which are susceptible to infection with a variety of different prions, i.e., which generally infect two or more types of test animals. For example, a mouse can be created that includes a chimeric gene including part of the sequence of a human, a separate chimeric gene that includes part of the sequence of a cow and another chimeric gene that includes part of the sequence of a sheep. If all three different types of chimeric genes are inserted into the genome of the mouse, the resulting mice are susceptible to infection with prions that generally only infect a human, cow and sheep.

After choosing the appropriate mammal, such as a mouse, and a suitable mode of genetic modification, such as inserting a chimeric PrP gene) a large number of such mammals that have substantially identical genetic material related to prions are produced. Each of the mice produced includes an identical chimeric gene present in the genome in substantially the same copy number. The mice should be sufficiently identical genetically in terms of genetic material related to prions that 95% or more of the mice will develop clinical signs of CNS dysfunction within 350 days or less after inoculation and all of the mice will develop such CNS dysfunction at approximately the same time such as, for example, within 30 days of each other.

Once a large group e.g., 50, 100, 500 or more of such mice are produced, the mice are inoculated with prions that generally only infect a genetically diverse mammal e.g., prions from a human, sheep, cow or horse. The amounts given to different groups of mammals can be varied. After inoculating the mammals with the prions the mammals are observed until the mammals exhibit symptoms of prion infection e.g., clinical signs of CNS dysfunction. After exhibiting the symptoms of prion infection the brain or at least a portion of the brain tissue of each of the mammals is extracted. The extracted brain tissue is homogenized to provide the standardized prion preparation.

As an alternative to inoculating the group of transgenic mice with prions from a genetically diverse animal, it is possible to produce mice that spontaneously develop prion related diseases. This can be done, for example, by including extremely high copy numbers of a human PrP gene into a mouse genome. When the copy number is raised to, for example, 100 or more copies, the mice spontaneously develop clinical signs of CNS dysfunction and have, within the brain tissue, prions that can infect humans. The brains of these animals or portions of the brain tissue of these animals can be extracted and homogenized to produce a standardized prion preparation.

The standardized prion preparations can be used directly or can be diluted and titered in a manner to provide a variety of different positive controls. By using standardized prion preparations, it is possible to create extremely dilute compositions containing the prions. For example, a composition containing one part per million or less or even one part per billion or less can be created. Such a composition can be used to test the sensitivity of the hybrid proteins, assays and methods provided herein. Prion preparations are desirable in that they will include a constant amount of prions and are extracted from an isogenic background. Accordingly, contaminates in the preparations are constant and controllable. Standardized prion preparations will be useful in the carrying out of bioassays in order to determine the presence, if any, of prions in various pharmaceuticals, whole blood, blood fractions, foods, cosmetics, organs and in particular any material which is derived from an animal (living or dead) such as organs, blood and products thereof derived from living or dead humans. Thus, standardized prion preparations are valuable in validating purification protocols where preparations are spiked and reductions in titer measured for a particular process.

F. Combinations and Kits

The hybrid molecules, such as the hybrid polypeptides, and any other reagents and material for performing the assays are provided as combinations, which can be packaged as kits that optionally contain a label with instructions for performing the assay. For example, a hybrid polypeptide can be provided in solution, as a liquid dispersion or as a substantially dry power, e.g., in lyophilized form. A solid support such as the above-described supports plate and one or more buffers also can be included as separately packaged elements in a kit.

The following examples are included for illustrative purposes only and are not intended to limit the scope of the invention.

G. Examples

Example 1

Materials and Methods

Immunoprecipitation. Whole brains from normal or 79A scrapie prion-infected mice (sacrificed 130-150 days post intracerebral inoculation) were homogenized at 10% (w/v) in phosphate buffered saline (PBS), diluted in an equal volume of 200 mM NaCl, 50 mM Tris-HCl (pH 8.0), 1% NP40 (or Triton X-100) and 1% deoxycholate, then rehomogenized and sonicated. Homogenates of normal or prion-infected brain were clarified at 500 g for 15 min, and the supernatants aliquoted and stored at −20° C.

A proportion of prion-infected homogenate was digested with proteinase K (40 µg/ml) for 1 h at 37° C. PMSF was added to these samples to a final concentration of 1 mM, prior to storage at −20° C. For each immunoprecipitation, hybrid polypeptide at a final concentration of 01. µg/ml to 10 µg/ml was incubated with a volume of brain homogenate containing 1 mg or less total protein for 2 h at 4° C. Tosyl-activated paramagnetic beads (Dynal) coupled to either polyclonal goat anti-human IgG F(ab')$_2$ (for detection of human Fabs) or to polyclonal goat anti-mouse IgG F(ab')$_2$ (for detection of antibody 6H4) were washed 3 times in washing buffer (0.05 M Tris, 0.2 M NaCl, containing 2% Nonidet P40 and 2% Tween 20 or TritonX-100) then incubated overnight at 4° C. with the hybrid polypeptide-homogenate mixture. Beads were then washed 3 times in washing buffer and once with TBS, before sedimentation by centrifugation.

Pelleted beads were resuspended in 20 µl loading buffer (150 mM Tris-HCl, pH 6.8, 6% sodium dodecyl sulphate (SDS), 0.3% bromophenol blue, 30% glycerol) and heated to 100° C. for 5 min. Samples were then run on 12% SDS-PAGE gels and transferred onto nitrocellulose membranes. Membranes were blocked with 5% (w/v) nonfat dry milk in TBS containing 0.1% Tween 20 (TBST) for 10 min at RT and blotted PrP was detected with 6H4 antibody or D13 antibody, which recognize normal bovine PrP (Korth et al. (1997) Nature 390:74-77). Blotted PrP protein was detected by incubation for 2 h at RT with a horseradish peroxidase conjugated rabbit anti-mouse IgG (Dako), diluted 1:5000 in blocking buffer. Membranes were then washed 5 times in TBST and developed with enhanced chemiluminescence reagent (Amersham) onto film. For plasminogen binding studies, 80 pg biotinylated human plasminogen (Enzyme Research Laboratories) was incubated with 1 mg brain homogenate, then captured onto streptavidin coated agarose beads. The beads were spun briefly, washed, resuspended in loading buffer, heated, repelleted and the bead eluate collected and examined for the presence of precipitated PrP by western blot.

SMB cells. SMB cells were grown to confluence in 162 cm$^2$ tissue culture flasks, washed twice with PBS, then lysed using 1 ml per flask of cell lysis buffer (10 mM Tris-HCl, pH 8.0, 100 mM NaCl, 10 mM EDTA, 0.5% w/v Nonidet P40, 0.5% w/v sodium deoxycholate). Cell lysate was cleared of debris by spinning at 1000 g for 5 min at 4° C. Immunoprecipitation experiments were performed as described above, using 3 mg of total lysate protein and 10 µg antibody in a final volume of 1 ml.

Example 2

Preparation of Motif-Grafted Hybrid Polypeptides

Mouse PrP sequences corresponding to amino acid residues 119-136, 121-144 and 121-158 (or 136-158 and 89-112, see EXAMPLE 4) were independently grafted to replace the HCDR3 domain of Fab b12 (Burton et al. (1994) Science 266:1024), using a two-step overlap extension PCR (McLane et al. (1995) Proc. Natl. Acad. Sci. U.S.A. 92:5214-5218; see FIG. 1) or IgG b12 (see, EXAMPLE 4).

Oligonucleotide primers were subjected to two-fold polyacrylamide gel electrophoresis purification (Operon Technologies) and contained the following sequences: PelSeq (5'-ACCTATTGCCTACGGCAGCCG-3'; SEQ ID NO:14); CG1d (5'-GCATGTACTAGTTTTGTCACA-AGATTTGG-3'; SEQ ID NO:15); MoPrP121-144 5' (5'-GGTGGCTACAT-GCTGGGGAGCGCCATGAGCAGGCCC-ATGATC-CATTTTGGCAACGACGGCGGTTATATGGACGTCT-GGGGCAAAGGGAC-3'; SEQ ID NO:16); MoPrP121-144 3' (5'-CCTGCTCATGGCGCTCCCCAGCATG-TAGCCACCAA-GGCCCCCCACTACCCCGC-CCACTCTCGCACAATAATAAACAGCCGTGT CTGC-3'; SEQ ID NO:17); MoPrP119-136 5' (5'-GTGGGGGGCCT-TGGTGGCTACATGCTGGGGAGCGCCATGAGCAGG-GGCGGTTATATGGACGTCTGGGGCAAAGGGAC-3'; SEQ ID NO:18); MoPrP119-136 3' (5'-CATGGCGCTC-CCCAGCATGTAGCCACC-AAGGCCCCCCACTACT-GCCCCGCCCACTCTCGCACAATAATAAACAGC-3; SEQ ID NO:19) MoPrP121-158 5' (5'-GACCGCTACTAC-CGTGAAAAC-ATGTACCGCTACCCTGGCGGT-TATATG GACGTCTGGGGCAAAGGG-3'; SEQ ID NO:20); MoPrP121-158 3' (5'-GCGGTACAT-GTTTTCACGGTAGTAGCGGTCCTCCCAGTCGTTGCC AAAATGGATCATGGGCCTG-3'; SEQ ID NO:21). All PCR reactions were performed with Pfu DNA Polymerase (Stratagene) using the following conditions: Step 1, (94° C., 30 sec; 52° C., 1 min; 72° C., 1 min 30 sec; 35 cycles); Step 2, (94° C., 30 sec; 50° C., 1 min; 72° C., 2 min; 10 cycles in the absence of flanking primers PelSeq and CG1d followed by 30 further cycles after addition of flanking primers). The resulting Fab b12 PrP heavy chain fragments were inserted between the XhoI and SpeI sites of pComb3H (Burton et al. (1994) *Science* 266:1024) containing parental b12 Fab light chain DNA. For a description of expression in CHO cells and preparation of IgG hybrid polypeptides see EXAMPLE 4.

Example 3

Test for Specific Binding to Disease Forms of PrP

The tests are designed to identify reagents that specifically bind to PrP$^{Sc}$ and PrP27-30 (which is the infectious protease-resistant core of PrP$^{Sc}$), but not to PrP$^{c}$ or with substantially lower affinity to PrP$^{c}$.

To study the reactivity of the PrP-Fab molecules against PrP$^{c}$, PrP$^{Sc}$ and PrP27-30, immunoprecipitation experiments were performed using brain homogenate prepared from normal mice and from mice infected with the 79A strain of scrapie prions. Immunoprecipitation was performed as described in Example 1. Fab b12 and PrP-Fabs 119-136, 121-144 and 121-158 were incubated with supernatant from a centrifuged homogenate prepared from whole brains of normal mice. Antibodies were precipitated with polyclonal goat anti-human IgG F(ab')$_2$ linked to paramagnetic beads. Precipitates were analyzed on western blot for the presence of PrP. Cross-reaction of the secondary antibody with the precipitating PrP-Fabs produces bands at approximately 50 kDa. PrP$^{c}$ was detected in a sample of normal brain homogenate and is specifically precipitated by the control antibody 6H4. No PrP$^{c}$ was detected following immunoprecipitation with Fab b12, or any of the PrP-Fabs.

PrP27-30 immunoprecipitated from a centrifuged homogenate of pK digested 79A prion-infected mouse brain. PrP 27-30 was present in crude homogenate. Equivalent PrP bands were present following immunoprecipitation with PrP-Fabs 119-136, 121-144 and 121-158. No PrP was evident in homogenates incubated with Fab b12, indicating that PrP 27-30 specificity is dependent upon the grafted PrP sequences. Full-length PrP$^{Sc}$ immunoprecipitated from a centrifuged homogenate of undigested prion-infected mouse brain was detected. PrP$^{Sc}$ was efficiently precipitated by Fab 121-158, but not by Fab b112. PrP$^{Sc}$ precipitated by plasminogen was also observed.

As positive controls, the 6H4 antibody was used to precipitate PrP$^c$ from normal mouse brain homogenates, and plasminogen (Fischer (2000) Nature 408:479) to precipitate PrP$^{Sc}$ from prion-infected brain samples. Reaction of PrP Fabs with PrP$^c$ in normal mouse brain was either absent or extremely weak. Each of these Fabs immunoprecipitated three PrP bands from pK-digested prion-infected brain homogenate. These bands corresponded in size to the di-, mono-, and unglycosylated forms of PrP27-30, the proteinase resistant core of PrP$^{Sc}$ in which the N-terminal portion of the protein between residues 23-90 has been enzymatically degraded. Fab 121-158 (FIG. 1B), which precipitated PrP27-30 with greatest efficiency, was next evaluated for reactivity with full-length PrP$^{Sc}$. Using this Fab, three bands of molecular weight 33-35 kDa, corresponding to full-length PrP$^{Sc}$, were precipitated from undigested homogenate of prion-infected brain tissue. Under identical experimental conditions, the parental b12 Fab did not react with either PrP$^c$, PrP$^{Sc}$ or PrP27-30. Moreover, Fabs containing PrP sequence no longer recognized gp120, the target antigen of the parental b12 antibody, did not bind to any other protein when used to probe western blots of mouse brain homogenate, and were completely unreactive with PrP$^{Sc}$ following its denaturation to a PrP$^c$-like conformation by heating in the presence of SDS. The grafted PrP sequence composed of residues 121-158 endows specific antibody recognition of PrP$^{Sc}$ and this disease-associated epitope is retained in PrP27-30.

Immunoprecipitation experiments in which Fab 121-158 was used to immunoprecipitate PrP from lysates of scrapie prion-infected SMB cells were performed. Fab b12 and Fab 121-158 were incubated with lysates of SMB cells propagating the Chandler mouse prion strain. In the absence of pK treatment neither Fab b12 nor Fab 121-158 recognized either PrP$^c$ or PrP$^{Sc}$. Following removal of PrP$^c$ by pK digestion, Fab 121-158 precipitated two clear bands of below 30 kDa in size and a more diffuse band at around 30 kDa. This banding pattern has been observed previously for pK-treated PrP$^{Sc}$ (PrP27-30) derived from SMB cells. Cross-reaction of the secondary antibody with the precipitating PrP-Fabs produces a band at approximately 50 kDa.

Once again, Fab 121-158 did not bind PrP$^c$ in untreated SMB lysate but was able to recognize PrP27-30 in these samples following pK digestion. Unlike the foregoing experiments in which Fab 121-158 efficiently precipitated PrP$^{Sc}$ from prion-infected brain homogenates, no full-length PrP$^{Sc}$ was immunoprecipitated from SMB cells using this antibody. Since the ratio of PrP$^c$:PrP$^{Sc}$ is approximately 4:1 in SMB cells, but can be considerably less than 1 in the brains of prion-infected mice with advanced disease, these observations can be best explained if, in the SMB lysates, PrP$^{Sc}$ is complexed with PrP$^c$ prior to addition of antibody. Under these circumstances, binding of Fab 121-158, which was originally designed to recognize the PrP$^{Sc}$ epitope bound by PrP$^c$, would be precluded. Conversely, in diseased brain tissues a proportion of PrP$^{Sc}$ molecules would be likely to remain uncomplexed because of the stoichiometric excess of PrP$^{Sc}$ over PrP$^c$ found in these preparations.

Of the three PrP Fab preparations tested in this Example, Fab121-158 possesses the greatest affinity for disease-associated PrP conformers. This hybrid polypeptide was the only one containing sequence composing the first α-helix of PrP$^c$ (residues 145-155). Fab19-136 and to a lesser extent Fab121-144, however, also bound disease-associated forms of PrP, indicating that helix A is not imperative for specific recognition of PrP$^{Sc}$ or PrP27-30. These data are consistent with studies in which transgenic mice lacking PrP sequence between residues 140 and 175 are susceptible to infection with native mouse prions, albeit with significantly prolonged incubation times. In vivo the intrinsic affinity of PrP$^{Sc}$ template for endogenous PrP$^c$ 'substrate' can be a key parameter governing the efficiency of prion replication and by implication, the pathological course of prion disease.

Antibody b12 molecules with the following PrP sequences grafted into the heavy chain CDR3 (methodologies identical to those described for the 121-158 construct in the Example) also have been prepared (residues numbers correspond to Syrian hamster numbers) and shown to specifically recognize PrP$^{Sc}$:

Mouse PrP: 87-112, 87-118, 87-130, 126-158, 131-158, 136-158, 141-158

Human PrP: 121-158 (129 M), 121-158 (129 V)

Bovine PrP: 121-158 (see amino acids 132-169 of SEQ ID NO:13.)

Example 4

Preparation and Testing of IgG Hybrid Polypeptides

Preparation of motif-grafted antibodies. Mouse PrP sequences corresponding to amino acid residues 89-112, 136-158 and 141-158 were independently grafted to replace the HCDR3 domain of antibody b12 using a two-step overlap extension PCR 19. Oligonucleotide primers were subject to two-fold polyacrylamide gel electrophoresis purification (Operon Technologies) and contained the following sequences: PelSeq (5'-ACCTATTGCCTACGGC-AGCCG-3'; SEQ ID NO:14); CG1d (5'-GCATGTACTAGTTTTGT-CACAAGATTTGG-3'; SEQ ID NO:15); MoPrP 89-112 (5'-CATAATCAGTGGAACAAGCCCAGCAAACCAAAAA CCAACCTCAAGCATGTGGGCGGT-TATATGGACGTCTGGGGCAAAGG-3' SEQ ID NO:22); MoPrP 89-112 3' (5'-GGG CTTGTTCCACTGATTATGGGTACCCCCTCCTTGGCC CCATCCACCCAC TCTCGCACAATAATAAACAGC-3', SEQ ID NO:23); MoPrP136-158 5' (5'-GTTTATTATTGT-GCGAGAGTGGGCGGGAGGCCCATGATCCATTTTGG CAACGAC-3', SEQ ID NO:24); MoPrP136-158 3' (5'-GCG-GTACATGTTTTCACGGTAGTAGCGGTC-CTCCCAGTCGTTGCCAA AATGGATCATGGGCCTG-3', SEQ ID NO:25); MoPrP141-158 5' (5'-GTTTATTATTGTGCGAGAGTGGGCGGGTTTGGCAAC GACTGGGAGGACC GCTAC-3', SEQ ID NO:26).

A scrambled MoPrP 136-158 graft was introduced into b12 antibody using the primers MoPrP 136-158 RAN 5' (5'-ATC-TACCAT ATGTTTAACGGCGAAAACCGTGAC-TACTGGTACGAGCGCGACGGCGGT TATATG-GACGTCTGGGGC-3', SEQ ID NO:27) and MoPrP 136-158 RAN 3' (5'-TTCGCCGTTAAACATATGGTAGATGCGCATGTAGGG AGGCCT CCCGCCCACTCTCGCACAATAATAAA-CAGT-3', SEQ ID NO:28).

All PCR reactions were performed with Pfu DNA Polymerase (Stratagene) using the following conditions: Step 1 (94° C., 30 sec; 52° C., 1 min; 72° C., 1 min 30 sec; 35 cycles plus a 10 min incubation at 72° C.); Step 2 (94° C., 30 sec; 50° C., 1 min; 72° C., 2 min; 10 cycles in the absence of flanking primers PelSeq and CG1d followed by 30 further cycles after addition of flanking primers, plus a 10 min incubation at 72° C.). The resulting b12 PrP heavy chain fragments were inserted between the XhoI and SpeI sites of phagemid Fab display vector pComb3H (available from New England Biolabs; see, also, Barbas, III et al (1995) *Methods: Comp. Meth Enzymol* 8:94-103) then subcloned into the pDR12 vector containing the parental b12 light-chain gene, for expression as human IgG1 in CHO cells (Maruyama et al. (1999) *J. Virol.* 73:6024-6030).

Immunoprecipitation

Whole brains from normal or RML or 79A scrapie prion-infected mice (sacrificed 130-150 days post intracerebral inoculation) were homogenized at 10% (w/v) in Tris buffered saline (TBS; 0.05M Tris, 0.2M NaCl, pH 7.4 containing 1% NP-40 and 1% DOC, diluted in an equal volume of TBS, then rehomogenized and sonicated. Homogenates of normal or prion-infected brain were clarified at 500 g for 15 min at 4° C. A proportion of clarified prion-infected homogenate was digested with proteinase K (50 μg/ml) for 1 h at 37° C. PMSF was added to all samples to a final concentration of 2 mM. For each immunoprecipitation, antibody at a final concentration of 0.3 μg/ml to 10 μg/ml was incubated for 2 h at room temperature with an aliquot of brain homogenate containing approximately 1 mg total protein, in a reaction mixture adjusted to a final volume of 500 μl with assay buffer (TBS containing 3% NP-40 and 3% Tween 20). Tosyl-activated paramagnetic beads (Dynal) coupled to either polyclonal goat anti-human IgG F(ab')2 (for detection of human PrP-grafted hybrid polypeptides) or to polyclonal goat anti-mouse IgG F(ab')2 (for detection of Fab D13 and IgG 6H4) were added to the hybrid polypeptide-homogenate mixture and incubated overnight at 4° C. Beads were then washed four times in washing buffer (TBS containing 2% NP-40 and 2% Tween 20) and once with TBS, before separation by magnet. Pelleted beads were resuspended in 20 μl loading buffer (150 mM Tris-HCl, pH 6.8, 6% sodium dodecyl sulphate (SDS), 0.3% bromophenol blue, 30% glycerol) and heated to 100° C. for 5 min. Samples were then run on 12% SDS-PAGE gels and transferred onto nitrocellulose membranes. Membranes were blocked with 5% (w/v) nonfat dry milk in TBS containing 0.1% Tween 20 (TBST) for 1 h at RT and blotted PrP detected with Fab D13 or IgG 6H4 antibodies at 1 μg/ml. After 5 washes in TBST, blotted PrP protein was detected by incubation for 30 min at RT with a horseradish peroxidase conjugated goat anti-mouse IgG (Pierce), diluted 1:10,000 in blocking buffer. Membranes were then washed 5 times in TBST and developed with enhanced chemiluminescence reagent (Amersham) onto film.

For plasminogen binding studies, 100 μg/ml biotinylated human plasminogen (Enzyme Research Laboratories) was incubated with 1 mg brain homogenate, then captured onto streptavidin coated agarose beads. The beads were spun briefly, washed, resuspended in loading buffer, heated, repelleted and the bead eluate examined for the presence of PrP by western blotting as described above. Immunoprecipitation in the presence of Triton X-100 was performed exactly as described above, except that the brain homogenization and reaction buffers contained 1% Triton X-100, rather than NP-40/DOC detergents.

Since modifications will be apparent to those of skill in this art, it is intended that this invention be limited only by the scope of the appended claims.

The invention claimed is:

1. A hybrid immunoglobulin or a Fab fragment of the hybrid immunoglobulin that specifically binds to the infectious form of a prion protein, comprising antibody b12 or a fragment thereof, wherein:
residues 119-131 of antibody b12 whose sequence is set forth in SEQ ID NO:4 or corresponding residues in a fragment thereof are replaced with residues 121-158 of the Syrian hamster prion polypeptide having a sequence set forth in SEQ ID NO: 5 or the corresponding residues of a prion polypeptide from another species or a portion of residues 121-158 or the corresponding residues that binds to the infectious form of a prion protein.

2. The hybrid immunoglobulin or the Fab fragment of claim 1 that comprises the heavy and light chains of antibody b12, wherein the heavy chain comprises the sequence of amino acids set forth in SEQ ID NO: 4, and the light chain comprises the sequence of amino acids set forth in SEQ ID NO: 2.

3. A hybrid immunoglobulin or a Fab fragment of the hybrid immunoglobulin that specifically binds to the infectious form of a prion protein, comprising antibody b12 or a fragment thereof, wherein:
residues 119-131 of antibody b12 whose sequence is set forth in SEQ ID NO:4 or corresponding residues in a fragment thereof are replaced with residues 87-112 of the Syrian hamster prion polypeptide having a sequence set forth in SEQ ID NO: 5 or the corresponding residues from prion polypeptides of another species or a portion of residues 87-112 or the corresponding residues that binds to the infectious form of a prion protein.

4. A hybrid immunoglobulin polypeptide or a fragment of the hybrid immunoglobulin, wherein:
a polypeptide motif is inserted within a complementarity-determining region (CDR) of the immunoglobulin molecule or fragment thereof, said polypeptide motif consisting of a sufficient number of contiguous amino acid residues from residues 136-158, 89 105, 89-112 or 95-112 of the Syrian hamster prion polypeptide having a sequence set forth in SEQ ID NO:5 or the corresponding residues of a prion polypeptide from another species so that the resulting fragment or hybrid immunoglobulin preferentially binds to the infectious $PrP^{Sc}$ form of the prion compared to the $PrP^c$ form; and
the fragment is a Fab, an F(ab)2 or single chain Fv.

5. The hybrid immunoglobulin or the fragment of claim 4 that is a Fab, an F(ab)2 or single chain Fv fragment.

6. A hybrid immunoglobulin or a Fab fragment of the hybrid immunoglobulin, wherein:
a polypeptide motif is inserted within the third complementarity-determining region (CDR) of an immunoglobulin molecule or a Fab fragment of the immunoglobulin molecule, said polypeptide motif consisting of a sufficient number of contiguous amino acid residues from residues 87-169 of the Syrian hamster prion polypeptide having a sequence set forth in SEQ ID NO: 5 or the corresponding residues of a prion polypeptide from another species so that the resulting Fab fragment or hybrid immunoglobulin preferentially binds to the infectious $PrP^{Sc}$ form of the prion compared to the $PrP^{c}$ form.

7. The hybrid immunoglobulin or the Fab fragment of claim 6, wherein the polypeptide motif consists of at least 5, 10, 15, 20, 25, 30, 35, 40, 45, 50, 55, 60, 65, 70, 75 or 80 residues or up to all of residues 87-169 of the Syrian hamster prion polypeptide having a sequence set forth in SEQ ID NO: 5 or the corresponding residues of a prion polypeptide from another species presented in its native non-infectious conformation.

8. The hybrid immunoglobulin or the Fab fragment of claim 6, wherein the polypeptide motif consists of residues from a portion of a PrP that corresponds to residues 87-169 of the Syrian hamster prion polypeptide having a sequence set forth in SEQ ID NO: 5 or the corresponding residues of a prion polypeptide from another species.

9. The hybrid immunoglobulin or the Fab fragment of claim 6, wherein the polypeptide motif consists of 10, 15, 20, 25, 30 or 35 contiguous residues that include residues 121-131, 121-141, 121-136, 121-144, 121-158, 87-112, 87-118, 87-130, 126-158, 131-158, 136-158 or 141-158 of the Syrian hamster prion polypeptide having a sequence set forth in SEQ ID NO: 5 or the corresponding residues of a prion polypeptide from another species.

10. The hybrid immunoglobulin or the Fab fragment of claim 6, wherein the prion from which the polypeptide motif is derived is an animal prion selected from among prions of humans, hamster, mice, rats, deer, sheep, goats, elk, kudu, horses, dogs, cats, camels and pigs.

11. The hybrid immunoglobulin or the Fab fragment of claim 6, wherein the polypeptide motif includes at least residues 136-158, 89-105, 89-112 or 95-112 of the Syrian hamster prion polypeptide having a sequence set forth in SEQ ID NO: 5 or the corresponding residues of a prion polypeptide from another species.

12. The hybrid immunoglobulin or the Fab fragment of claim 6, wherein the polypeptide motif contains only residues 136-158, 89-105, 89-112 or 95-112 of the Syrian hamster prion polypeptide having a sequence set forth in SEQ ID NO: 5 or the corresponding residues of a prion polypeptide from another species.

13. The hybrid immunoglobulin or the Fab fragment of claim 6, wherein the polypeptide motif includes at least residues 145-155 from the PrPc form of the Syrian hamster prion polypeptide having a sequence set forth in SEQ ID NO: 5 or the corresponding residues of a prion polypeptide from another species.

14. The hybrid immunoglobulin polypeptide or the Fab fragment of claim 6, wherein the motif contains at least 5, 10, 15, 20, 25, 30 or 35 contiguous residues from the region of residues 119-158 of the prion polypeptide, wherein:
residues from the region are the only prion-derived residues in the polypeptide; and
the residues correspond upon alignment of the prion sequence with the Syrian hamster prion sequence to residues 119-158 of the prion polypeptide whose sequence is set forth in SEQ ID NO: 5 or the corresponding residues from prion polypeptides of other species.

15. The hybrid immunoglobulin polypeptide or the Fab fragment of claim 14, wherein the prion is an animal prion selected from the group consisting of humans, hamsters, mice, rats, deer, sheep, goats, elk, kudu, horses, dogs, cats, camels and pigs.

16. A solid support comprising a plurality of the hybrid immunoglobulins or the Fab fragments of claim 1 or claim 6.

17. The hybrid immunoglobulin or the Fab fragment of claim 6, wherein the hybrid immunoglobulin or the Fab fragment is antibody b12 or a Fab fragment of antibody b12.

18. The hybrid immunoglobulin polypeptide or the Fab fragment of claim 6 that is a Fab fragment.

19. The hybrid immunoglobulin molecule or the Fab fragment of claim 17 that is a Fab fragment.

20. The hybrid immunoglobulin or the Fab fragment of claim 6, wherein:
the polypeptide motif consists of at least residues 101-106 or at least residues 136-150 of the Syrian hamster prion polypeptide having a sequence set forth in SEQ ID NO: 5 or the corresponding residues of a prion polypeptide from another species.

21. The hybrid immunoglobulin or the Fab fragment of claim 20, wherein the other species are selected from among sheep, human and cows.

22. The hybrid immunoglobulin or the Fab fragment of claim 20, wherein the hybrid immunoglobulin polypeptide or the Fab fragment is antibody b12 or a Fab fragment of antibody b12.

23. The hybrid immunoglobulin or the Fab fragment of claim 17 that is the Fab fragment, wherein the polypeptide motif consists of at least 5, 10, 15, 20, 25, 30, 35, 40, 45, 50, 55, 60, 65, 70, 75 or 80 residues or up to all of residues 87-169 of the Syrian hamster prion polypeptide having a sequence set forth in SEQ ID NO: 5 or the corresponding residues of a prion polypeptide from another species presented in its native non-infectious conformation.

24. The hybrid immunoglobulin or the Fab fragment of claim 23 that is the Fab fragment, consisting of at least residues 121-131, 121-141, 121-136, 121-144, 121-158, 87-112, 87-118, 87-130, 126-158, 131-158, 136-158 or 141-158 of the Syrian hamster prion polypeptide having a sequence set forth in SEQ ID NO: 5 or the corresponding residues of a prion polypeptide from another species.

25. The hybrid immunoglobulin or the Fab fragment of claim 23 that is the Fab fragment, wherein the polypeptide motif contains only residues 121-131, 121-141, 121-136, 121-144, 121-158, 87-112, 87-118, 87-130, 126-158, 131-158, 136-158 or 141-158 of the Syrian hamster prion polypeptide having a sequence set forth in SEQ ID NO: 5 or the corresponding residues of a prion polypeptide from another species.

26. The hybrid immunoglobulin or the Fab fragment of claim 23 that is the Fab fragment and contains at least residues 136-158, 89-105, 89-112 or 95-112 of the Syrian hamster prion polypeptide having a sequence set forth in SEQ ID NO: 5 or the corresponding residues of a prion polypeptide from another species.

27. The hybrid immunoglobulin or the Fab fragment of claim 23 that is the Fab fragment, wherein the polypeptide motif contains only residues 136-158, 89-105, 89-112 or 95-112 of the Syrian hamster prion polypeptide having a sequence set forth in SEQ ID NO: 5 or the corresponding residues of a prion polypeptide from another species.

28. The hybrid immunoglobulin or the Fab fragment of claim 23 that is the Fab fragment and contains residues that include at least one α-helix from the PrPc form of the prion.

29. The hybrid immunoglobulin or the Fab fragment of claim 23 that is the Fab fragment, wherein:

the polypeptide motif consists of at least 5, 10, 15, 20, 25, 30 or 35 contiguous residues from the region of residues 119-158 of the Syrian hamster prion polypeptide having a sequence set forth in SEQ ID NO: 5 or the corresponding residues of a prion polypeptide from another species; and residues from the region are the only prion-derived residues in the polypeptide.

30. The hybrid immunoglobulin or the Fab fragment of claim 29 that is the Fab fragment, wherein the prion is an animal prion selected from the group consisting of humans, hamsters, mice, rats, deer, sheep, goats, elk, kudu, horses, dogs, cats, camels and pigs.

31. The hybrid immunoglobulin polypeptide or the Fab fragment of any of claims 7, 8 and 10 that is a Fab fragment of the hybrid immunoglobulin.

32. The hybrid immunoglobulin or the Fab fragment of claim 6, wherein the polypeptide motif contains one or more of at least residues 89-112, 100-106 or 136-141 of the Syrian hamster prion set forth in SEQ ID NO:5 or corresponding residues from a prion polypeptide of another species.

33. The hybrid immunoglobulin polypeptide or the Fab fragment of claim 31, wherein;

the Fab fragment is an antibody b12 Fab fragment.

34. The hybrid immunoglobulin of claim 1 or claim 3 that is the Fab fragment.

35. The hybrid immunoglobulin or the Fab fragment of claim 14 that is the Fab fragment.

36. The hybrid immunoglobulin or the Fab fragment of claim 20 that is the Fab fragment.

37. The hybrid immunoglobulin or the Fab fragment of claim 15 that is the Fab fragment.

* * * * *

UNITED STATES PATENT AND TRADEMARK OFFICE
CERTIFICATE OF CORRECTION

PATENT NO. : 7,939,641 B2  
APPLICATION NO. : 10/410907  
DATED : May 10, 2011  
INVENTOR(S) : Burton et al.

Page 1 of 1

It is certified that error appears in the above-identified patent and that said Letters Patent is hereby corrected as shown below:

IN THE SPECIFICATION:
At column 1, line 24, please replace "grant Nos. HL63817, AG021312 and NS14069" with --Contract Nos. HL063817, AG0021312 and NS014069--.

Signed and Sealed this
Twenty-ninth Day of November, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,939,641 B2 | |
| APPLICATION NO. | : 10/410907 | |
| DATED | : May 10, 2011 | |
| INVENTOR(S) | : Burton et al. | |

It is certified that error appears in the above-identified patent and that said Letters Patent is hereby corrected as shown below:

IN THE CLAIMS:

Column 84, line 52 to line 65 should read:
4. A hybrid immunoglobulin polypeptide or a fragment of the hybrid immunoglobulin, wherein:
a polypeptide motif is inserted within a complementarity-determining region (CDR) of the immunoglobulin molecule or fragment thereof, said polypeptide motif consisting of a sufficient number of contiguous amino acid residues from residues 136-158, 89-105, 89-112 or 95-112 of the Syrian hamster prion polypeptide having a sequence set forth in SEQ ID NO:5 or the corresponding residues of a prion polypeptide from another species so that the resulting fragment or hybrid immunoglobulin preferentially binds to the infectious PrPsc form of the prion compared to the PrPc form; and
the fragment is a Fab, an F(ab)2 or single chain Fv.

Signed and Sealed this
Twenty-eighth Day of February, 2012

David J. Kappos
*Director of the United States Patent and Trademark Office*

SEQUENCE LISTING

```
<160> NUMBER OF SEQ ID NOS: 36

<210> SEQ ID NO 1
<211> LENGTH: 729
<212> TYPE: DNA
<213> ORGANISM: Homo sapiens
<220> FEATURE:
<221> NAME/KEY: CDS
<222> LOCATION: (9)...(715)
<223> OTHER INFORMATION: IgG Fab b12- Light Chain

<400> SEQUENCE: 1 agcttacc atg ggt gtg ccc act cag gtc ctg ggg ttg ctg ctg ctg tgg        50
         Met Gly Val Pro Thr Gln Val Leu Gly Leu Leu Leu Leu Trp
          1               5                  10 ctt aca gat gcc aga tgt gag atc gtt ctc acg cag tct cca ggc acc         98
Leu Thr Asp Ala Arg Cys Glu Ile Val Leu Thr Gln Ser Pro Gly Thr
 15                  20                  25                  30 ctg tct ctg tct cca ggg gaa aga gcc acc ttc tcc tgt agg tcc agt        146
Leu Ser Leu Ser Pro Gly Glu Arg Ala Thr Phe Ser Cys Arg Ser Ser
                 35                  40                  45 cac agc att cgc agc cgc cgc gta gcc tgg tac cag cac aaa cct ggc        194
His Ser Ile Arg Ser Arg Arg Val Ala Trp Tyr Gln His Lys Pro Gly
             50                  55                  60 cag gct cca agg ctg gtc ata cat ggt gtt tcc aat agg gcc tct ggc        242
Gln Ala Pro Arg Leu Val Ile His Gly Val Ser Asn Arg Ala Ser Gly
         65                  70                  75 atc tca gac agg ttc agc ggc agt ggg tct ggg aca gac ttc act ctc        290
```

```
Ile Ser Asp Arg Phe Ser Gly Ser Gly Ser Gly Thr Asp Phe Thr Leu
     80                  85                  90 acc atc acc aga gtg gag cct gaa gac ttt gca ctg tac tac tgt cag      338
Thr Ile Thr Arg Val Glu Pro Glu Asp Phe Ala Leu Tyr Tyr Cys Gln
 95                 100                 105                 110 gtc tat ggt gcc tcc tcg tac act ttt ggc cag ggg acc aaa ctg gag      386
Val Tyr Gly Ala Ser Ser Tyr Thr Phe Gly Gln Gly Thr Lys Leu Glu
                115                 120                 125 agg aaa cga act gtg cct gca cca tct gtc ttc atc ttc ccg cca tct      434
Arg Lys Arg Thr Val Pro Ala Pro Ser Val Phe Ile Phe Pro Pro Ser
            130                 135                 140 gat gag cag ttg aaa tct ggg act gcc tct gtt gtg tgc ctg ctg aat      482
Asp Glu Gln Leu Lys Ser Gly Thr Ala Ser Val Val Cys Leu Leu Asn
            145                 150                 155 aac ttc tat ccc aga gag gcc aaa gta cag tgg aag gtg gat aac gcc      530
Asn Phe Tyr Pro Arg Glu Ala Lys Val Gln Trp Lys Val Asp Asn Ala
        160                 165                 170 ctc caa tcg ggt aac tcc cag gag agt gtc aca gag cag gac agc aag      578
Leu Gln Ser Gly Asn Ser Gln Glu Ser Val Thr Glu Gln Asp Ser Lys
175                 180                 185                 190 gac agc acc tac agc ctc agc agc acc ctg acg ctg agc aaa gca gac      626
Asp Ser Thr Tyr Ser Leu Ser Ser Thr Leu Thr Leu Ser Lys Ala Asp
                195                 200                 205 tac gag aaa cac aaa gtc tac gcc tgc gaa gtc acc cat cag ggc ctg      674
Tyr Glu Lys His Lys Val Tyr Ala Cys Glu Val Thr His Gln Gly Leu
            210                 215                 220 agt tcg ccc gtc aca aag agc ttc aac agg gga gag tgt ta attctagaga    725
Ser Ser Pro Val Thr Lys Ser Phe Asn Arg Gly Glu Cys
        225                 230                 235 attc                                                                  729

<210> SEQ ID NO 2
<211> LENGTH: 235
<212> TYPE: PRT
<213> ORGANISM: Homo sapiens

<400> SEQUENCE: 2

Met Gly Val Pro Thr Gln Val Leu Gly Leu Leu Leu Leu Trp Leu Thr
 1               5                  10                  15

Asp Ala Arg Cys Glu Ile Val Leu Thr Gln Ser Pro Gly Thr Leu Ser
            20                  25                  30

Leu Ser Pro Gly Glu Arg Ala Thr Phe Ser Cys Arg Ser Ser His Ser
        35                  40                  45

Ile Arg Ser Arg Arg Val Ala Trp Tyr Gln His Lys Pro Gly Gln Ala
 50                  55                  60

Pro Arg Leu Val Ile His Gly Val Ser Asn Arg Ala Ser Gly Ile Ser
65                  70                  75                  80

Asp Arg Phe Ser Gly Ser Gly Ser Gly Thr Asp Phe Thr Leu Thr Ile
                85                  90                  95

Thr Arg Val Glu Pro Glu Asp Phe Ala Leu Tyr Tyr Cys Gln Val Tyr
            100                 105                 110

Gly Ala Ser Ser Tyr Thr Phe Gly Gln Gly Thr Lys Leu Glu Arg Lys
        115                 120                 125

Arg Thr Val Pro Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
```

```
                165                 170                 175
Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 3
<211> LENGTH: 3282
<212> TYPE: DNA
<213> ORGANISM: Homo sapiens
<220> FEATURE:
<221> NAME/KEY: CDS
<222> LOCATION: (15)...(452)
<223> OTHER INFORMATION: IGg Fab b12- Heavy Chain

<400> SEQUENCE: 3
aattcgccgc cacc atg gaa tgg agc tgg gtc ttt ctc ttc ttc ctg tca          50
                Met Glu Trp Ser Trp Val Phe Leu Phe Phe Leu Ser
                1               5                   10 gta act aca ggt gtc cac tcc cag gtt cag ctg gtt cag tcc ggg gct          98
Val Thr Thr Gly Val His Ser Gln Val Gln Leu Val Gln Ser Gly Ala
            15                  20                  25 gag gtg aag aag cct ggg gcc tca gtg aag gtt tct tgt cag gct tct         146
Glu Val Lys Lys Pro Gly Ala Ser Val Lys Val Ser Cys Gln Ala Ser
        30                  35                  40 gga tac aga ttc agt aac ttt gtt att cat tgg gtg cgc cag gcc ccc         194
Gly Tyr Arg Phe Ser Asn Phe Val Ile His Trp Val Arg Gln Ala Pro
45                  50                  55                  60 gga cag agg ttt gag tgg atg gga tgg atc aat cct tac aac gga aac         242
Gly Gln Arg Phe Glu Trp Met Gly Trp Ile Asn Pro Tyr Asn Gly Asn
                65                  70                  75 aaa gaa ttt tca gcg aag ttc cag gac aga gtc acc ttt acc gcg gac         290
Lys Glu Phe Ser Ala Lys Phe Gln Asp Arg Val Thr Phe Thr Ala Asp
            80                  85                  90 aca tcc gcg aac aca gcc tac atg gag ttg agg agc ctc agg tct gca         338
Thr Ser Ala Asn Thr Ala Tyr Met Glu Leu Arg Ser Leu Arg Ser Ala
        95                  100                 105 gac acg gct gtt tat tat tgt gcg aga gtg ggg cca tat agt tgg gat         386
Asp Thr Ala Val Tyr Tyr Cys Ala Arg Val Gly Pro Tyr Ser Trp Asp
    110                 115                 120 gat tct ccc cag gac aat tat tat atg gac gtc tgg ggc aaa gga acc         434
Asp Ser Pro Gln Asp Asn Tyr Tyr Met Asp Val Trp Gly Lys Gly Thr
125                 130                 135                 140 acg gtc atc gtg agc tca gcttccacca agggcccatc ggtcttcccc                482
Thr Val Ile Val Ser Ser
                145 ctggcaccct cctccaagag cacctctggg ggcacagcgg ccctgggctg cctggtcaag       542 gactacttcc ccgaaccggt gacggtgtcg tggaactcag gcgccctgac cagcggcgtg       602 cacaccttcc cggctgtcct acagtcctca ggactctact ccctcagcag cgtggtgacc       662 gtgccctcca gcagcttggg cacccagacc tacatctgca acgtaatca caagcccagc       722 aacaccaagg tggacaagaa agttggtgag aggccagcac agggagggag ggtgtctgct       782 ggaagccagg ctcagcgctc ctgcctggac gcatccggc tatgcagccc cagtccaggg       842 cagcaaggca ggccccgtct gcctcttcac ccggaggcct ctgcccgccc cactcatgct       902
```

```
cagggagagg gtcttctggc ttttteeeca ggctctgggc aggcacaggc taggtgcccc      962
taacccaggc cctgcacaca aagggcagg tgctgggctc agacctgcca agagccatat      1022
ccgggaggac cctgcccctg acctaagccc accccaaagg ccaaactctc cactccctca      1082
gctcggacac cttctctcct cccagattcg agtaactccc aatcttctct ctgcagagcc      1142
caaatcttgt gacaaaactc acacatgccc accgtgccca ggtaagccag cccaggcctc      1202
gccctccagc tcaaggcggg acaggtgccc tagagtagcc tgcatccagg acaggcccc      1262 agccgggtgc tgacacgtcc acctccatct ctccctcagc acctgaggcc gcgggaggac      1322
catcagtctt cctcttcccc ccaaaaccca aggacaccct catgatctcc cggacccctg      1382
aggtcacatg cgtggtggtg gacgtgagcc acgaagaccc tgaggtcaag ttcaactggt      1442
acgtggacgg cgtggaggtg cataatgcca agacaaagcc gcgggaggag cagtacaaca      1502
gcacgtaccg tgtggtcagc gtcctcaccg tcctgcacca ggactggctg aatggcaagg      1562
agtacaagtg caaggtctcc aacaaagccc tcccagcccc catcgagaaa accatctcca      1622
aagccaaagg tgggacccgt ggggtgcgag ggccacatgg acagaggccg gctcggccca      1682
ccctctgccc tgagagtgac cgctgtacca acctctgtcc ctacagggca gccccgagaa      1742
ccacaggtgt acaccctgcc cccatcccgg gatgagctga ccaagaacca ggtcagcctg      1802
acctgcctgg tcaaaggctt ctatcccagc gacatcgccg tggagtggga gagcaatggg      1862
cagccggaga caactacaa gaccacgcct cccgtgctgg actccgacgg ctccttcttc      1922
ctctacagca agctcaccgt ggacaagagc aggtggcagc aggggaacgt cttctcatgc      1982
tccgtgatgc atgaggctct gcacaaccac tacacgcaga agagcctctc cctgtctccg      2042
ggtaaatgag tgcgacggcc ggcaagcccc cgctccccgg gctctcgcgg tcgcacgagg      2102
atgcttggca cgtacccct gtacatactt cccgggcgcc cagcatggaa ataaagcacc      2162
cagcgctgcc ctgggcccct gcgagactgt gatggttctt ccacgggtc aggccgagtc      2222 tgaggcctga gtggcatgag ggaggcagag cgggtcccac tgtccccaca ctggcccagg      2282
ctgtgcaggt gtgcctgggc cgcctagggt ggggctcagc caggggctgc cctcggcagg      2342
gtgggggatt tgccagcgtt gccctccctc agcagcacc tgccctgggc tgggccacgg      2402
gaagccctag gagcccctgg ggacagacac acagcccctg cctctgtagg agactgtcct      2462
gttctgtgag cgccctgtcc tccgacctcc atgcccactc gggggcatgc ctagtccatg      2522
tgcgtaggga caggccctcc ctcacccatc taccccacg gcactaaccc ctggctgtcc      2582
tgcccagcct cgcacccgca tggggacaca accgactccg gggacatgca ctctcgggcc      2642
ctgtggaggg actggtgcag atgcccacac acacactcag tccagacccg ttcaacaaaa      2702
cccccgcact gaggttggcc ggccacacgg ccaccacaca cacacgtgca cgcctcacac      2762
acggagcctc acccgggcga actgcacagc acccagacca gagcaaggtc ctcgcacacg      2822
tgaacactcc tcggacacag gccccacga gccccacgcg gcacctcaag gcccacgagc      2882
ctctcggcag cttctccaca tgctgacctg ctcagacaaa cccagccctc ctctcacaag      2942
ggtgcccctg cagccgccac acacacacag gggatcacac accacgtcac gtccctggcc      3002
ctggcccact tcccagtgcc gcccttccct gcagggcgga tcataatcag ccataccaca      3062
tttgtagagg ttttacttgc tttaaaaaac ctcccacacc tccccctgaa cctgaaacat      3122
aaaatgaatg caattgttgt tgttaacttg tttattgcag cttataatgg ttacaaataa      3182
agcaatagca tcacaaattt cacaaataaa gcatttttt cactgcattc tagttgtggt      3242
ttgtccaaac tcatcaatgt atcttatcat gtctagatcc                           3282
```

<210> SEQ ID NO 4
<211> LENGTH: 146
<212> TYPE: PRT
<213> ORGANISM: Homo sapiens

<400> SEQUENCE: 4

Met Glu Trp Ser Trp Val Phe Leu Phe Phe Leu Ser Val Thr Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Gln Ala Ser Gly Tyr Arg Phe
        35                  40                  45

Ser Asn Phe Val Ile His Trp Val Arg Gln Ala Pro Gly Gln Arg Phe
    50                  55                  60

Glu Trp Met Gly Trp Ile Asn Pro Tyr Asn Gly Asn Lys Glu Phe Ser
65                  70                  75                  80

Ala Lys Phe Gln Asp Arg Val Thr Phe Thr Ala Asp Thr Ser Ala Asn
                85                  90                  95

Thr Ala Tyr Met Glu Leu Arg Ser Leu Arg Ser Ala Asp Thr Ala Val
            100                 105                 110

Tyr Tyr Cys Ala Arg Val Gly Pro Tyr Ser Trp Asp Ser Pro Gln
        115                 120                 125

Asp Asn Tyr Tyr Met Asp Val Trp Gly Lys Gly Thr Thr Val Ile Val
    130                 135                 140

Ser Ser
145

<210> SEQ ID NO 5
<211> LENGTH: 254
<212> TYPE: PRT
<213> ORGANISM: Mesocricetus auratus (Syrian hamster)

<400> SEQUENCE: 5

Met Ala Asn Leu Ser Tyr Trp Leu Leu Ala Leu Phe Val Ala Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly
    50                  55                  60

Trp Gly Gln Pro His Gly Gly Trp Gly Gln Pro His Gly Gly
65                  70                  75                  80

Trp Gly Gln Pro His Gly Gly Gly Trp Gly Gln Gly Gly Gly Thr His
                85                  90                  95

Asn Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Met Met His Phe Gly Asn Asp
    130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Phe Val
                165                 170                 175

His Asp Cys Val Asn Ile Thr Ile Lys Gln His Thr Val Thr Thr Thr

```
                    180                 185                 190
Thr Lys Gly Glu Asn Phe Thr Glu Thr Asp Ile Lys Ile Met Glu Arg
            195                 200                 205

Val Val Glu Gln Met Cys Thr Thr Gln Tyr Gln Lys Glu Ser Gln Ala
        210                 215                 220

Tyr Tyr Asp Gly Arg Arg Ser Ser Ala Val Leu Phe Ser Pro Pro
225                 230                 235                 240

Val Ile Leu Leu Ile Ser Phe Leu Ile Phe Leu Met Val Gly
            245                 250

<210> SEQ ID NO 6
<211> LENGTH: 254
<212> TYPE: PRT
<213> ORGANISM: Mesocricetus auratus (Armenian hamster)

<400> SEQUENCE: 6

Met Ala Asn Leu Ser Tyr Trp Leu Leu Ala Leu Phe Val Ala Thr Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Asn Gln Trp Asn Lys Pro Asn Lys Pro Lys Thr Ser Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Met Leu His Phe Gly Asn Asp
    130                 135                 140

Trp Glu Asp Arg Tyr Tyr Arg Glu Asn Met Asn Arg Tyr Pro Asn Gln
145                 150                 155                 160

Val Tyr Tyr Arg Pro Val Asp Gln Tyr Asn Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Val Thr Gln Tyr Gln Lys Glu Ser Gln Ala
    210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 7
<211> LENGTH: 254
<212> TYPE: PRT
<213> ORGANISM: Cricetulus griseus (Chinese hamster)

<400> SEQUENCE: 7

Met Ala Asn Leu Ser Tyr Trp Leu Leu Ala Leu Phe Val Ala Thr Trp
1               5                   10                  15
```

```
Thr Asp Val Gly Leu Cys Lys Lys Arg Pro Lys Pro Gly Gly Trp Asn
             20                   25                  30
Thr Gly Gly Ser Arg Tyr Pro Gly Gln Gly Ser Pro Gly Gly Asn Arg
         35                   40                  45
Tyr Pro Pro Gln Gly Gly Gly Thr Trp Gly Gln Pro His Gly Gly Gly
 50                   55                  60
Trp Gly Gln Pro His Gly Gly Gly Trp Gly Gln Pro His Gly Gly Gly
 65                  70                  75                  80
Trp Gly Gln Pro His Gly Gly Gly Trp Gly Gln Gly Gly Gly Thr His
                 85                  90                  95
Asn Gln Trp Asn Lys Pro Ser Lys Pro Lys Thr Asn Met Lys His Val
             100                 105                 110
Ala Gly Ala Ala Ala Ala Gly Ala Val Val Gly Gly Leu Gly Gly Tyr
         115                 120                 125
Met Leu Gly Ser Ala Met Ser Arg Pro Met Leu His Phe Gly Asn Asp
130                 135                 140
Trp Glu Asp Arg Tyr Tyr Arg Glu Asn Met Asn Arg Tyr Pro Asn Gln
145                 150                 155                 160
Val Tyr Tyr Arg Pro Val Asp Gln Tyr Asn Asn Gln Asn Asn Phe Val
                165                 170                 175
His Asp Cys Val Asn Ile Thr Ile Lys Gln His Thr Val Thr Thr Thr
            180                 185                 190
Thr Lys Gly Glu Asn Phe Thr Glu Thr Asp Val Lys Met Met Glu Arg
        195                 200                 205
Val Val Glu Gln Met Cys Val Thr Gln Tyr Gln Lys Glu Ser Gln Ala
210                 215                 220
Tyr Tyr Asp Gly Arg Arg Ser Ser Ala Val Leu Phe Ser Ser Pro Pro
225                 230                 235                 240
Val Ile Leu Leu Ile Ser Phe Leu Ile Phe Leu Ile Val Gly
                245                 250

<210> SEQ ID NO 8
<211> LENGTH: 253
<212> TYPE: PRT
<213> ORGANISM: Homo sapiens

<400> SEQUENCE: 8

Met Ala Asn Leu Gly Cys Trp Met Leu Val Leu Phe Val Ala Thr Trp
 1               5                  10                  15
Ser Asp Leu Gly Leu Cys Lys Lys Arg Pro Lys Pro Gly Gly Trp Asn
             20                  25                  30
Thr Gly Gly Ser Arg Tyr Pro Gly Gln Gly Ser Pro Gly Gly Asn Arg
         35                  40                  45
Tyr Pro Pro Gln Gly Gly Gly Gly Trp Gly Gln Pro His Gly Gly Gly
 50                  55                  60
Trp Gly Gln Pro His Gly Gly Gly Trp Gly Gln Pro His Gly Gly Gly
 65                  70                  75                  80
Trp Gly Gln Pro His Gly Gly Gly Trp Gly Gln Gly Gly Gly Thr His
                 85                  90                  95
Ser Gln Trp Asn Lys Pro Ser Lys Pro Lys Thr Asn Met Lys His Met
             100                 105                 110
Ala Gly Ala Ala Ala Ala Gly Ala Val Val Gly Gly Leu Gly Gly Tyr
         115                 120                 125
Met Leu Gly Ser Ala Met Ser Arg Pro Ile Ile His Phe Gly Ser Asp
130                 135                 140
```

```
Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
            165                 170                 175

His Asp Cys Val Asn Ile Thr Ile Lys Gln His Thr Val Thr Thr Thr
        180                 185                 190

Thr Lys Gly Glu Asn Phe Thr Glu Thr Asp Val Lys Met Met Glu Arg
    195                 200                 205

Val Val Glu Gln Met Cys Ile Thr Gln Tyr Glu Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
            245                 250
```

<210> SEQ ID NO 9
<211> LENGTH: 254
<212> TYPE: PRT
<213> ORGANISM: Mus Musculus (type A)

<400> SEQUENCE: 9

```
Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Thr His Asn
                85                  90                  95

Gln Trp Asn Lys Pro Ser Lys Pro Lys Thr Asn Leu Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
            165                 170                 175

Asp Cys Val Asn Ile Thr Ile Lys Gln His Thr Val Thr Thr Thr Thr
        180                 185                 190

Lys Gly Glu Asn Phe Thr Glu Thr Asp Val Lys Met Met Glu Arg Val
    195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
            245                 250
```

<210> SEQ ID NO 10

```
<211> LENGTH: 254
<212> TYPE: PRT
<213> ORGANISM: Mus musculus  (type B)

<400> SEQUENCE: 10

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Thr His Asn
                85                  90                  95

Gln Trp Asn Lys Pro Ser Lys Pro Lys Thr Asn Phe Lys His Val Ala
            100                 105                 110

Gly Ala Ala Ala Ala Gly Ala Val Val Gly Gly Leu Gly Gly Tyr Met
        115                 120                 125

Leu Gly Ser Ala Met Ser Arg Pro Met Ile His Phe Gly Asn Asp Trp
    130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr
            180                 185                 190

Lys Gly Glu Asn Phe Thr Glu Thr Asp Val Lys Met Met Glu Arg Val
        195                 200                 205

Val Glu Gln Met Cys Val Thr Gln Tyr Gln Lys Glu Ser Gln Ala Tyr
    210                 215                 220

Tyr Asp Gly Arg Arg Ser Ser Ser Thr Val Leu Phe Ser Ser Pro Pro
225                 230                 235                 240

Val Ile Leu Leu Ile Ser Phe Leu Ile Phe Leu Ile Val Gly
                245                 250

<210> SEQ ID NO 11
<211> LENGTH: 256
<212> TYPE: PRT
<213> ORGANISM: Ovis aries  (Sheep)

<400> SEQUENCE: 11

Met Val Lys Ser His Ile Gly Ser Trp Ile Leu Val Leu Phe Val Ala
1               5                   10                  15

Met Trp Ser Asp Val Gly Leu Cys Lys Lys Arg Pro Lys Pro Gly Gly
            20                  25                  30

Gly Trp Asn Thr Gly Gly Ser Arg Tyr Pro Gly Gln Gly Ser Pro Gly
        35                  40                  45

Gly Asn Arg Tyr Pro Pro Gln Gly Gly Gly Trp Gly Gln Pro His
    50                  55                  60

Gly Gly Gly Trp Gly Gln Pro His Gly Gly Trp Gly Gln Pro His
65                  70                  75                  80

Gly Gly Gly Trp Gly Gln Pro His Gly Gly Gly Trp Gly Gln Gly
                85                  90                  95
```

```
Gly Ser His Ser Gln Trp Asn Lys Pro Ser Lys Pro Lys Thr Asn Met
                100                 105                 110
Lys His Val Ala Gly Ala Ala Ala Gly Ala Val Val Gly Gly Leu
        115                 120                 125
Gly Gly Tyr Met Leu Gly Ser Ala Met Ser Arg Pro Leu Ile His Phe
        130                 135                 140
Gly Asn Asp Tyr Glu Asp Arg Tyr Tyr Arg Glu Asn Met Tyr Arg Tyr
145                 150                 155                 160
Pro Asn Gln Val Tyr Tyr Arg Pro Val Asp Arg Tyr Ser Asn Gln Asn
                165                 170                 175
Asn Phe Val His Asp Cys Val Asn Ile Thr Val Lys Gln His Thr Val
                180                 185                 190
Thr Thr Thr Thr Lys Gly Glu Asn Phe Thr Glu Thr Asp Ile Lys Ile
        195                 200                 205
Met Glu Arg Val Val Glu Gln Met Cys Ile Thr Gln Tyr Gln Arg Glu
        210                 215                 220
Ser Gln Ala Tyr Tyr Gln Arg Gly Ala Ser Val Ile Leu Phe Ser Ser
225                 230                 235                 240
Pro Pro Val Ile Leu Leu Ile Ser Phe Leu Ile Phe Leu Ile Val Gly
                245                 250                 255

<210> SEQ ID NO 12
<211> LENGTH: 256
<212> TYPE: PRT
<213> ORGANISM: Ovis aries (Sheep)
<220> FEATURE:
<221> NAME/KEY: VARIANT
<222> LOCATION: 171
<223> OTHER INFORMATION: R to Q

<400> SEQUENCE: 12

Met Val Lys Ser His Ile Gly Ser Trp Ile Leu Val Leu Phe Val Ala
1               5                   10                  15
Met Trp Ser Asp Val Gly Leu Cys Lys Lys Arg Pro Lys Pro Gly Gly
            20                  25                  30
Gly Trp Asn Thr Gly Gly Ser Arg Tyr Pro Gly Gln Gly Ser Pro Gly
        35                  40                  45
Gly Asn Arg Tyr Pro Pro Gln Gly Gly Gly Trp Gly Gln Pro His
50                  55                  60
Gly Gly Gly Trp Gly Gln Pro His Gly Gly Gly Trp Gly Gln Pro His
65                  70                  75                  80
Gly Gly Gly Trp Gly Gln Pro His Gly Gly Gly Trp Gly Gln Gly
            85                  90                  95
Gly Ser His Ser Gln Trp Asn Lys Pro Ser Lys Pro Lys Thr Asn Met
                100                 105                 110
Lys His Val Ala Gly Ala Ala Ala Gly Ala Val Val Gly Gly Leu
        115                 120                 125
Gly Gly Tyr Met Leu Gly Ser Ala Met Ser Arg Pro Leu Ile His Phe
        130                 135                 140
Gly Asn Asp Tyr Glu Asp Arg Tyr Tyr Arg Glu Asn Met Tyr Arg Tyr
145                 150                 155                 160
Pro Asn Gln Val Tyr Tyr Arg Pro Val Asp Gln Tyr Ser Asn Gln Asn
                165                 170                 175
Asn Phe Val His Asp Cys Val Asn Ile Thr Val Lys Gln His Thr Val
                180                 185                 190
Thr Thr Thr Thr Lys Gly Glu Asn Phe Thr Glu Thr Asp Ile Lys Ile
        195                 200                 205
```

```
Met Glu Arg Val Val Glu Gln Met Cys Ile Thr Gln Tyr Gln Arg Glu
    210                 215                 220

Ser Gln Ala Tyr Tyr Gln Arg Gly Ala Ser Val Ile Leu Phe Ser Ser
225                 230                 235                 240

Pro Pro Val Ile Leu Leu Ile Ser Phe Leu Ile Phe Leu Ile Val Gly
                245                 250                 255

<210> SEQ ID NO 13
<211> LENGTH: 264
<212> TYPE: PRT
<213> ORGANISM: Bos taurus (bovine)

<400> SEQUENCE: 13

Met Val Lys Ser His Ile Gly Ser Trp Ile Leu Val Leu Phe Val Ala
  1               5                  10                  15

Met Trp Ser Asp Val Gly Leu Cys Lys Lys Arg Pro Lys Pro Gly Gly
             20                  25                  30

Gly Trp Asn Thr Gly Gly Ser Arg Tyr Pro Gly Gln Gly Ser Pro Gly
             35                  40                  45

Gly Asn Arg Tyr Pro Pro Gln Gly Gly Gly Trp Gly Gln Pro His
 50                  55                  60

Gly Gly Gly Trp Gly Gln Pro His Gly Gly Gly Trp Gly Gln Pro His
65                  70                  75                  80

Gly Gly Gly Trp Gly Gln Pro His Gly Gly Gly Trp Gly Gln Pro His
                85                  90                  95

Gly Gly Gly Gly Trp Gly Gln Gly Thr His Gly Gln Trp Asn Lys
                100                 105                 110

Pro Ser Lys Pro Lys Thr Asn Met Lys His Val Ala Gly Ala Ala Ala
            115                 120                 125

Ala Gly Ala Val Val Gly Gly Leu Gly Gly Tyr Met Leu Gly Ser Ala
    130                 135                 140

Met Ser Arg Pro Leu Ile His Phe Gly Ser Asp Tyr Glu Asp Arg Tyr
145                 150                 155                 160

Tyr Arg Glu Asn Met His Arg Tyr Pro Asn Gln Val Tyr Tyr Arg Pro
                165                 170                 175

Val Asp Gln Tyr Ser Asn Gln Asn Asn Phe Val His Asp Cys Val Asn
            180                 185                 190

Ile Thr Val Lys Glu His Thr Val Thr Thr Thr Lys Gly Glu Asn
    195                 200                 205

Phe Thr Glu Thr Asp Ile Lys Met Met Glu Arg Val Val Glu Gln Met
    210                 215                 220

Cys Ile Thr Gln Tyr Gln Arg Glu Ser Gln Ala Tyr Tyr Gln Arg Gly
225                 230                 235                 240

Ala Ser Val Ile Leu Phe Ser Ser Pro Pro Val Ile Leu Leu Ile Ser
                245                 250                 255

Phe Leu Ile Phe Leu Ile Val Gly
            260

<210> SEQ ID NO 14
<211> LENGTH: 21
<212> TYPE: DNA
<213> ORGANISM: Artificial Sequence
<220> FEATURE:
<223> OTHER INFORMATION: Primer pelseq

<400> SEQUENCE: 14
acctattgcc tacggcagcc g                                           21
```

<210> SEQ ID NO 15
<211> LENGTH: 29
<212> TYPE: DNA
<213> ORGANISM: Artificial Sequence
<220> FEATURE:
<223> OTHER INFORMATION: Primer Cg1d

<400> SEQUENCE: 15
gcatgtacta gttttgtcac aagatttgg                                29

<210> SEQ ID NO 16
<211> LENGTH: 89
<212> TYPE: DNA
<213> ORGANISM: Artificial Sequence
<220> FEATURE:
<223> OTHER INFORMATION: Primer Moprp121-144 5_

<400> SEQUENCE: 16
ggtggctaca tgctggggag cgccatgagc aggcccatga tccatttttgg caacgacggc    60 ggttatatgg acgtctgggg caaagggac                                      89

<210> SEQ ID NO 17
<211> LENGTH: 87
<212> TYPE: DNA
<213> ORGANISM: Artificial Sequence
<220> FEATURE:
<223> OTHER INFORMATION: Primer Moprp121-144 3_

<400> SEQUENCE: 17
cctgctcatg gcgctcccca gcatgtagcc accaaggccc cccactaccc cgcccactct    60
cgcacaataa taaacagccg tgtctgc                                        87

<210> SEQ ID NO 18
<211> LENGTH: 77
<212> TYPE: DNA
<213> ORGANISM: Artificial Sequence
<220> FEATURE:
<223> OTHER INFORMATION: Primer Moprp119-136 5_

<400> SEQUENCE: 18
gtggggggcc ttggtggcta catgctgggg agcgccatga gcaggggcgg ttatatggac    60
gtctggggca aagggac                                                   77

<210> SEQ ID NO 19
<211> LENGTH: 75
<212> TYPE: DNA
<213> ORGANISM: Artificial Sequence
<220> FEATURE:
<223> OTHER INFORMATION: Primer
<400> SEQUENCE: 19 Moprp119-136 3_ catggcgctc cccagcatgt agccaccaag gccccccact actgcccccgc ccactctcgc    60 acaataataa acagc                                                     75

<210> SEQ ID NO 20
<211> LENGTH: 66
<212> TYPE: DNA
<213> ORGANISM: Artificial Sequence
<220> FEATURE:
<223> OTHER INFORMATION: Primer Moprp121-158 5_

<400> SEQUENCE: 20
gaccgctact accgtgaaaa catgtaccgc taccctggcg gttatatgga cgtctggggc    60
aaaggg                                                              66

<210> SEQ ID NO 21
<211> LENGTH: 64
<212> TYPE: DNA
<213> ORGANISM: Artificial Sequence
<220> FEATURE:
<223> OTHER INFORMATION: Primer Moprp121-158 3_

<400> SEQUENCE: 21
gcggtacatg ttttcacggt agtagcggtc ctcccagtcg ttgccaaaat ggatcatggg    60
cctg                                                                64

<210> SEQ ID NO 22
<211> LENGTH: 80
<212> TYPE: DNA
<213> ORGANISM: Artificial Sequence
<220> FEATURE:
<223> OTHER INFORMATION: Primer MoPrP 89-112 5'

<400> SEQUENCE: 22
cataatcagt ggaacaagcc cagcaaacca aaaaccaacc tcaagcatgt gggcggttat    60
atggacgtct ggggcaaagg                                               80

<210> SEQ ID NO 23
<211> LENGTH: 72
<212> TYPE: DNA
<213> ORGANISM: Artificial Sequence
<220> FEATURE:
<223> OTHER INFORMATION: Primer MoPrP 89-112 3'

<400> SEQUENCE: 23
gggcttgttc cactgattat gggtaccccc tccttggccc catccaccca ctctcgcaca    60
ataataaaca gc                                                       72

<210> SEQ ID NO 24
<211> LENGTH: 54
<212> TYPE: DNA
<213> ORGANISM: Artificial Sequence
<220> FEATURE:
<223> OTHER INFORMATION: Primer MoPrP136-158 5'

<400> SEQUENCE: 24
gtttattatt gtgcgagagt gggcgggagg cccatgatcc attttggcaa cgac          54

<210> SEQ ID NO 25
<211> LENGTH: 64
<212> TYPE: DNA
<213> ORGANISM: Artificial Sequence
<220> FEATURE:
<223> OTHER INFORMATION: Primer MoPrP136-158 3'

<400> SEQUENCE: 25
gcggtacatg ttttcacggt agtagcggtc ctcccagtcg ttgccaaaat ggatcatggg    60
cctg                                                                64

<210> SEQ ID NO 26
<211> LENGTH: 54
<212> TYPE: DNA
<213> ORGANISM: Artificial Sequence
<220> FEATURE:
<223> OTHER INFORMATION: MoPrP141-158 5'

<400> SEQUENCE: 26

```
gtttattatt gtgcgagagt gggcgggttt ggcaacgact gggaggaccg ctac              54

<210> SEQ ID NO 27
<211> LENGTH: 75
<212> TYPE: DNA
<213> ORGANISM: Artificial Sequence
<220> FEATURE:
<223> OTHER INFORMATION: Primer MoPrP 136-158 RAN 5'

<400> SEQUENCE: 27
atctaccata tgtttaacgg cgaaaaccgt gactactggt acgagcgcga cggcggttat      60
atggacgtct ggggc                                                       75

<210> SEQ ID NO 28
<211> LENGTH: 72
<212> TYPE: DNA
<213> ORGANISM: Artificial Sequence
<220> FEATURE:
<223> OTHER INFORMATION: Primer MoPrP 136-158 RAN 3'

<400> SEQUENCE: 28
ttcgccgtta acatatggt agatgcgcat gtagggaggc ctcccgccca ctctcgcaca       60
ataataaaca gt                                                          72

<210> SEQ ID NO 29
<211> LENGTH: 486
<212> TYPE: DNA
<213> ORGANISM: Artificial Sequence
<220> FEATURE:
<223> OTHER INFORMATION: D13 Light Chain
<220> FEATURE:
<221> NAME/KEY: CDS
<222> LOCATION: (1)...(486)

<400> SEQUENCE: 29
```

| atg | gcc | gag | ctc | cag | atg | acc | cag | tct | cca | ctc | act | ttg | tcg | gtt | gcc | 48 |
|---|---|---|---|---|---|---|---|---|---|---|---|---|---|---|---|---|
| Met | Ala | Glu | Leu | Gln | Met | Thr | Gln | Ser | Pro | Leu | Thr | Leu | Ser | Val | Ala | |
| 1 | | | | 5 | | | | | 10 | | | | | 15 | | |

| att | gga | caa | cca | gcc | tcc | atc | tct | tgc | aag | tca | agt | cag | agc | ctc | tta | 96 |
|---|---|---|---|---|---|---|---|---|---|---|---|---|---|---|---|---|
| Ile | Gly | Gln | Pro | Ala | Ser | Ile | Ser | Cys | Lys | Ser | Ser | Gln | Ser | Leu | Leu | |
| | | | 20 | | | | | 25 | | | | | 30 | | | |

| gtt | agt | gat | gga | aag | aca | tat | ttg | aat | tgg | ttg | tta | cag | agg | cca | ggc | 144 |
|---|---|---|---|---|---|---|---|---|---|---|---|---|---|---|---|---|
| Val | Ser | Asp | Gly | Lys | Thr | Tyr | Leu | Asn | Trp | Leu | Leu | Gln | Arg | Pro | Gly | |
| | | 35 | | | | | 40 | | | | | 45 | | | | |

| cag | tct | cca | aag | cgc | cta | atc | tat | ctg | gtg | tct | aaa | ctg | gac | tct | gga | 192 |
|---|---|---|---|---|---|---|---|---|---|---|---|---|---|---|---|---|
| Gln | Ser | Pro | Lys | Arg | Leu | Ile | Tyr | Leu | Val | Ser | Lys | Leu | Asp | Ser | Gly | |
| | 50 | | | | | 55 | | | | | 60 | | | | | |

| gtc | cct | gac | agg | ttc | act | ggc | agt | gga | tca | ggg | aca | gat | ttc | aca | ctg | 240 |
|---|---|---|---|---|---|---|---|---|---|---|---|---|---|---|---|---|
| Val | Pro | Asp | Arg | Phe | Thr | Gly | Ser | Gly | Ser | Gly | Thr | Asp | Phe | Thr | Leu | |
| 65 | | | | 70 | | | | | 75 | | | | | 80 | | |

| aaa | atc | agc | aga | gtg | gag | gct | gag | gat | ttg | gga | gtt | tat | tat | tgc | tgg | 288 |
|---|---|---|---|---|---|---|---|---|---|---|---|---|---|---|---|---|
| Lys | Ile | Ser | Arg | Val | Glu | Ala | Glu | Asp | Leu | Gly | Val | Tyr | Tyr | Cys | Trp | |
| | | | 85 | | | | | 90 | | | | | 95 | | | |

| caa | ggt | aca | cat | ttt | cct | cag | acg | ttc | ggt | gga | ggc | acc | aag | ctg | gaa | 336 |
|---|---|---|---|---|---|---|---|---|---|---|---|---|---|---|---|---|
| Gln | Gly | Thr | His | Phe | Pro | Gln | Thr | Phe | Gly | Gly | Gly | Thr | Lys | Leu | Glu | |
| | | | 100 | | | | | 105 | | | | | 110 | | | |

| atc | aaa | cgg | gct | gat | gct | gca | cca | act | gta | tcc | atc | ttc | cca | cca | tcc | 384 |
|---|---|---|---|---|---|---|---|---|---|---|---|---|---|---|---|---|
| Ile | Lys | Arg | Ala | Asp | Ala | Ala | Pro | Thr | Val | Ser | Ile | Phe | Pro | Pro | Ser | |
| | | 115 | | | | | 120 | | | | | 125 | | | | |

| agt | gag | cag | tta | aca | tct | gga | ggt | gcc | tca | gtc | gtg | tgc | ttc | ttg | aac | 432 |
|---|---|---|---|---|---|---|---|---|---|---|---|---|---|---|---|---|
| Ser | Glu | Gln | Leu | Thr | Ser | Gly | Gly | Ala | Ser | Val | Val | Cys | Phe | Leu | Asn | |
| | 130 | | | | | 135 | | | | | 140 | | | | | |

```
aac ttc tac ccc aaa gac atc aat gtc aag tgg aag att gat ggc agt     480
Asn Phe Tyr Pro Lys Asp Ile Asn Val Lys Trp Lys Ile Asp Gly Ser
145                 150                 155                 160 gaa cga                                                             486
Glu Arg

<210> SEQ ID NO 30
<211> LENGTH: 162
<212> TYPE: PRT
<213> ORGANISM: Artificial Sequence
<220> FEATURE:
<223> OTHER INFORMATION: D13 Light Chain

<400> SEQUENCE: 30

Met Ala Glu Leu Gln Met Thr Gln Ser Pro Leu Thr Leu Ser Val Ala
1               5                   10                  15

Ile Gly Gln Pro Ala Ser Ile Ser Cys Lys Ser Ser Gln Ser Leu Leu
            20                  25                  30

Val Ser Asp Gly Lys Thr Tyr Leu Asn Trp Leu Leu Gln Arg Pro Gly
        35                  40                  45

Gln Ser Pro Lys Arg Leu Ile Tyr Leu Val Ser Lys Leu Asp Ser Gly
    50                  55                  60

Val Pro Asp Arg Phe Thr Gly Ser Gly Ser Gly Thr Asp Phe Thr Leu
65                  70                  75                  80

Lys Ile Ser Arg Val Glu Ala Glu Asp Leu Gly Val Tyr Tyr Cys Trp
                85                  90                  95

Gln Gly Thr His Phe Pro Gln Thr Phe Gly Gly Gly Thr Lys Leu Glu
            100                 105                 110

Ile Lys Arg Ala Asp Ala Ala Pro Thr Val Ser Ile Phe Pro Pro Ser
        115                 120                 125

Ser Glu Gln Leu Thr Ser Gly Gly Ala Ser Val Val Cys Phe Leu Asn
    130                 135                 140

Asn Phe Tyr Pro Lys Asp Ile Asn Val Lys Trp Lys Ile Asp Gly Ser
145                 150                 155                 160

Glu Arg

<210> SEQ ID NO 31
<211> LENGTH: 372
<212> TYPE: DNA
<213> ORGANISM: Artificial Sequence
<220> FEATURE:
<223> OTHER INFORMATION: D13 Heavy Chain
<220> FEATURE:
<221> NAME/KEY: CDS
<222> LOCATION: (1)...(372)

<400> SEQUENCE: 31 atg gcc gag gtg cag ctg ctc gag cag tct ggg gca gag ctt gtg aag     48
Met Ala Glu Val Gln Leu Leu Glu Gln Ser Gly Ala Glu Leu Val Lys
1               5                   10                  15 cca ggg gcc tca gtc aaa ttg tcc tgc aca acc tca ggc tta aac att     96
Pro Gly Ala Ser Val Lys Leu Ser Cys Thr Thr Ser Gly Leu Asn Ile
            20                  25                  30 gaa gac tac tat att cac tgg gtg aag cag agg cct gaa cag ggc ctg    144
Glu Asp Tyr Tyr Ile His Trp Val Lys Gln Arg Pro Glu Gln Gly Leu
        35                  40                  45 gag tgg att gga agg att gat cct gag aat ggt gaa act tta tat gcc    192
Glu Trp Ile Gly Arg Ile Asp Pro Glu Asn Gly Glu Thr Leu Tyr Ala
    50                  55                  60 ccg gaa ttc cag ggc aag gcc act ata aca gca gac aca tca tcc aac    240
Pro Glu Phe Gln Gly Lys Ala Thr Ile Thr Ala Asp Thr Ser Ser Asn
```

```
                    65                  70                  75                  80
aca gtc tac cta cag ctc aga agc ctg aca tct gag gac act gcc atc        288
Thr Val Tyr Leu Gln Leu Arg Ser Leu Thr Ser Glu Asp Thr Ala Ile
                85                  90                  95 tat tac tgt ggg aga ttt gat ggc aac ggc tgg tac ctc gat gtc tgg        336
Tyr Tyr Cys Gly Arg Phe Asp Gly Asn Gly Trp Tyr Leu Asp Val Trp
            100                 105                 110 ggc gca ggg acc acg gtc acc gtc tcc tca gcc aaa                        372
Gly Ala Gly Thr Thr Val Thr Val Ser Ser Ala Lys
        115                 120

<210> SEQ ID NO 32
<211> LENGTH: 124
<212> TYPE: PRT
<213> ORGANISM: Artificial Sequence
<220> FEATURE:
<223> OTHER INFORMATION: D13 Heavy Chain

<400> SEQUENCE: 32

Met Ala Glu Val Gln Leu Leu Glu Gln Ser Gly Ala Glu Leu Val Lys
  1               5                  10                  15

Pro Gly Ala Ser Val Lys Leu Ser Cys Thr Thr Ser Gly Leu Asn Ile
                 20                  25                  30

Glu Asp Tyr Tyr Ile His Trp Val Lys Gln Arg Pro Glu Gln Gly Leu
             35                  40                  45

Glu Trp Ile Gly Arg Ile Asp Pro Glu Asn Gly Glu Thr Leu Tyr Ala
         50                  55                  60

Pro Glu Phe Gln Gly Lys Ala Thr Ile Thr Ala Asp Thr Ser Ser Asn
 65                  70                  75                  80

Thr Val Tyr Leu Gln Leu Arg Ser Leu Thr Ser Glu Asp Thr Ala Ile
                 85                  90                  95

Tyr Tyr Cys Gly Arg Phe Asp Gly Asn Gly Trp Tyr Leu Asp Val Trp
            100                 105                 110

Gly Ala Gly Thr Thr Val Thr Val Ser Ser Ala Lys
        115                 120

<210> SEQ ID NO 33
<211> LENGTH: 648
<212> TYPE: DNA
<213> ORGANISM: Artificial Sequence
<220> FEATURE:
<223> OTHER INFORMATION: D18 Light Chain
<220> FEATURE:
<221> NAME/KEY: CDS
<222> LOCATION: (1)...(648)

<400> SEQUENCE: 33 atg gcc gag ctc gtg ctc acc cag tct cca gca ttc atg tct gca tct        48
Met Ala Glu Leu Val Leu Thr Gln Ser Pro Ala Phe Met Ser Ala Ser
  1               5                  10                  15 cca ggg gag aag gtc acc atg acc tgc agt gcc agc tca agt gta aat        96
Pro Gly Glu Lys Val Thr Met Thr Cys Ser Ala Ser Ser Ser Val Asn
                 20                  25                  30 tac atg cac tgg tac cag cag aag tca ggc acc tcc ccc aaa aga tgg       144
Tyr Met His Trp Tyr Gln Gln Lys Ser Gly Thr Ser Pro Lys Arg Trp
             35                  40                  45 att tat gac aca tcc aaa ctg gct tct gga gtc cct gct cgc ttc agt       192
Ile Tyr Asp Thr Ser Lys Leu Ala Ser Gly Val Pro Ala Arg Phe Ser
         50                  55                  60 ggc agt ggg tct ggg acc tct tac tct ctc aca atc agc agc atg gag       240
Gly Ser Gly Ser Gly Thr Ser Tyr Ser Leu Thr Ile Ser Ser Met Glu
 65                  70                  75                  80
```

```
gct gaa gat gct gcc act tat tac tgc cag cag tgg agt agt aac ccg      288
Ala Glu Asp Ala Ala Thr Tyr Tyr Cys Gln Gln Trp Ser Ser Asn Pro
                85                  90                  95 tac acg ttc gga ggg ggg acc aag ctg gaa ata aaa cgg gct gat gct      336
Tyr Thr Phe Gly Gly Gly Thr Lys Leu Glu Ile Lys Arg Ala Asp Ala
            100                 105                 110 gca cca act gta tcc atc ttc cca cca tcc agt gag cag tta aca tct      384
Ala Pro Thr Val Ser Ile Phe Pro Pro Ser Ser Glu Gln Leu Thr Ser
        115                 120                 125 gga ggt gcc tca gtc gtg tgc ttc ttg aac aac ttc tac ccc aaa gac      432
Gly Gly Ala Ser Val Val Cys Phe Leu Asn Asn Phe Tyr Pro Lys Asp
    130                 135                 140 atc aat gtc aag tgg aag att gat ggc agg gaa cga caa aat ggc gtc      480
Ile Asn Val Lys Trp Lys Ile Asp Gly Arg Glu Arg Gln Asn Gly Val
145                 150                 155                 160 ctg aac agt tgg act gat cag gac agc aaa gac agc acc tac agc atg      528
Leu Asn Ser Trp Thr Asp Gln Asp Ser Lys Asp Ser Thr Tyr Ser Met
                165                 170                 175 agc agc acc ctc acg ttg acc gag gac gag tat gaa cga cat aac agc      576
Ser Ser Thr Leu Thr Leu Thr Glu Asp Glu Tyr Glu Arg His Asn Ser
            180                 185                 190 tat acc tgt gag gcc act cac aag aca tca act tca ccc att gtc aag      624
Tyr Thr Cys Glu Ala Thr His Lys Thr Ser Thr Ser Pro Ile Val Lys
        195                 200                 205 agc ttc aac agg aat gag tgt taa                                       648
Ser Phe Asn Arg Asn Glu Cys *
    210                 215

<210> SEQ ID NO 34
<211> LENGTH: 215
<212> TYPE: PRT
<213> ORGANISM: Artificial Sequence
<220> FEATURE:
<223> OTHER INFORMATION: D18 Light Chain

<400> SEQUENCE: 34

Met Ala Glu Leu Val Leu Thr Gln Ser Pro Ala Phe Met Ser Ala Ser
 1               5                  10                  15

Pro Gly Glu Lys Val Thr Met Thr Cys Ser Ala Ser Ser Ser Val Asn
            20                  25                  30

Tyr Met His Trp Tyr Gln Gln Lys Ser Gly Thr Ser Pro Lys Arg Trp
        35                  40                  45

Ile Tyr Asp Thr Ser Lys Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Asn Pro
                85                  90                  95

Tyr Thr Phe Gly Gly Gly Thr Lys Leu Glu Ile Lys Arg Ala Asp Ala
            100                 105                 110

Ala Pro Thr Val Ser Ile Phe Pro Pro Ser Ser Glu Gln Leu Thr Ser
        115                 120                 125

Gly Gly Ala Ser Val Val Cys Phe Leu Asn Asn Phe Tyr Pro Lys Asp
    130                 135                 140

Ile Asn Val Lys Trp Lys Ile Asp Gly Arg Glu Arg Gln Asn Gly Val
145                 150                 155                 160

Leu Asn Ser Trp Thr Asp Gln Asp Ser Lys Asp Ser Thr Tyr Ser Met
                165                 170                 175
```

```
Ser Ser Thr Leu Thr Leu Thr Glu Asp Glu Tyr Glu Arg His Asn Ser
        180                 185                 190
Tyr Thr Cys Glu Ala Thr His Lys Thr Ser Thr Ser Pro Ile Val Lys
        195                 200                 205
Ser Phe Asn Arg Asn Glu Cys
        210             215

<210> SEQ ID NO 35
<211> LENGTH: 672
<212> TYPE: DNA
<213> ORGANISM: Artificial Sequence
<220> FEATURE:
<223> OTHER INFORMATION: D18 Heavy Chain
<220> FEATURE:
<221> NAME/KEY: CDS
<222> LOCATION: (1)...(672)

<400> SEQUENCE: 35 atg gcc gag gtg cag ctg ctc gag cag tca gga cct gag ctg gtg aag      48
Met Ala Glu Val Gln Leu Leu Glu Gln Ser Gly Pro Glu Leu Val Lys
  1               5                  10                  15 cct ggg tct tca gtg aag ata tcc tgc aag gct tct aga tac aca ttc      96
Pro Gly Ser Ser Val Lys Ile Ser Cys Lys Ala Ser Arg Tyr Thr Phe
                 20                  25                  30 act gac tac aac atg gac tgg gtg aag cag agc cat gga aag aga ctt     144
Thr Asp Tyr Asn Met Asp Trp Val Lys Gln Ser His Gly Lys Arg Leu
             35                  40                  45 gag tgg att gga tat att tat cct aac act ggt gtt act ggc tac aac     192
Glu Trp Ile Gly Tyr Ile Tyr Pro Asn Thr Gly Val Thr Gly Tyr Asn
     50                  55                  60 cag agg ttc aag ggc aag gcc aca ttg act gta gac aag tcc tcc agc     240
Gln Arg Phe Lys Gly Lys Ala Thr Leu Thr Val Asp Lys Ser Ser Ser
 65                  70                  75                  80 aca gcc tac atg gaa ctc cgc agc ctg aca tct gag gac tct gca gtc     288
Thr Ala Tyr Met Glu Leu Arg Ser Leu Thr Ser Glu Asp Ser Ala Val
                 85                  90                  95 tat tac tgt gca gga ttt tac tac ggt atg gac tat tgg ggt caa gga     336
Tyr Tyr Cys Ala Gly Phe Tyr Tyr Gly Met Asp Tyr Trp Gly Gln Gly
            100                 105                 110 acc tca gtc acc gtc tcc tca gcc aaa acg aca ccc cca tct gtc tat     384
Thr Ser Val Thr Val Ser Ser Ala Lys Thr Thr Pro Pro Ser Val Tyr
        115                 120                 125 cca ctg gcc cct gga tct gct gcc caa act aac tcc atg gtg acc ctg     432
Pro Leu Ala Pro Gly Ser Ala Ala Gln Thr Asn Ser Met Val Thr Leu
    130                 135                 140 gga tgc ctg gtc aag ggc tat ttc cct gag cca gtg aca gtg acc tgg     480
Gly Cys Leu Val Lys Gly Tyr Phe Pro Glu Pro Val Thr Val Thr Trp
145                 150                 155                 160 aac tct gga tcc ctg tcc agc ggt gtg cac acc ttc cca gct gtc ctg     528
Asn Ser Gly Ser Leu Ser Ser Gly Val His Thr Phe Pro Ala Val Leu
                165                 170                 175 cag tat gac ctc tac act atg agc agc tca gtg act gtc ccc tcc agc     576
Gln Tyr Asp Leu Tyr Thr Met Ser Ser Ser Val Thr Val Pro Ser Ser
            180                 185                 190 acc tgg ccc agc gag acc gtc acc tgc aac gtt gcc cac ccg gcc agc     624
Thr Trp Pro Ser Glu Thr Val Thr Cys Asn Val Ala His Pro Ala Ser
        195                 200                 205 agc acc aag gtg gac aag aaa att gtg ccc agg gat tgt act agc taa     672
Ser Thr Lys Val Asp Lys Lys Ile Val Pro Arg Asp Cys Thr Ser *
    210                 215                 220

<210> SEQ ID NO 36
```

```
-continued

<211> LENGTH: 223
<212> TYPE: PRT
<213> ORGANISM: Artificial Sequence
<220> FEATURE:
<223> OTHER INFORMATION: D18 Heavy Chain

<400> SEQUENCE: 36

Met Ala Glu Val Gln Leu Leu Glu Gln Ser Gly Pro Glu Leu Val Lys
  1               5                  10                  15

Pro Gly Ser Ser Val Lys Ile Ser Cys Lys Ala Ser Arg Tyr Thr Phe
             20                  25                  30

Thr Asp Tyr Asn Met Asp Trp Val Lys Gln Ser His Gly Lys Arg Leu
         35                  40                  45

Glu Trp Ile Gly Tyr Ile Tyr Pro Asn Thr Gly Val Thr Gly Tyr Asn
 50                  55                  60

Gln Arg Phe Lys Gly Lys Ala Thr Leu Thr Val Asp Lys Ser Ser Ser
 65                  70                  75                  80

Thr Ala Tyr Met Glu Leu Arg Ser Leu Thr Ser Glu Asp Ser Ala Val
                 85                  90                  95

Tyr Tyr Cys Ala Gly Phe Tyr Tyr Gly Met Asp Tyr Trp Gly Gln Gly
            100                 105                 110

Thr Ser Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
            130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Tyr Asp Leu Tyr Thr Met Ser Ser Ser Val Thr Val Pro Ser Ser
            180                 185                 190

Thr Trp Pro Ser Glu Thr Val Thr Cys Asn Val Ala His Pro Ala Ser
            195                 200                 205

Ser Thr Lys Val Asp Lys Lys Ile Val Pro Arg Asp Cys Thr Ser
        210                 215                 220
```